(12) United States Patent
Flanagan et al.

(10) Patent No.: US 8,920,491 B2
(45) Date of Patent: Dec. 30, 2014

(54) MEDICAL DEVICES HAVING A COATING OF INORGANIC MATERIAL

(75) Inventors: Aiden Flanagan, Galway (IE); John Kilcooley, Galway (IE); Tim O'Connor, Galway (IE); Barry O'Brien, Galway (IE); Dominique Seidel, Munich (DE); Michael Kuehling, Munich (DE); Torsten Scheuermann, Munich (DE); Jan Weber, Maastricht (NL)

(73) Assignee: Boston Scientific SciMed, Inc., Maple Grove, MN (US)

( * ) Notice: Subject to any disclaimer, the term of this patent is extended or adjusted under 35 U.S.C. 154(b) by 514 days.

(21) Appl. No.: 12/425,791

(22) Filed: Apr. 17, 2009

(65) Prior Publication Data

US 2009/0264975 A1 Oct. 22, 2009

Related U.S. Application Data

(60) Provisional application No. 61/047,002, filed on Apr. 22, 2008.

(51) Int. Cl.
*A61F 2/06* (2013.01)
*A61L 29/10* (2006.01)
*A61L 29/16* (2006.01)
*A61L 31/08* (2006.01)
*A61L 31/16* (2006.01)

(52) U.S. Cl.
CPC .......... *A61L 29/10* (2013.01); *A61L 29/16* (2013.01); *A61L 31/082* (2013.01); *A61L 31/16* (2013.01); *A61L 2300/602* (2013.01); *A61L 2300/61* (2013.01)
USPC .......... 623/1.44; 623/1.46; 623/1.45

(58) Field of Classification Search
CPC .......... A61F 2013/00676; A61F 13/51403; A61F 2002/30075; A61F 2013/00523
USPC .............. 623/1.42, 1.46; 604/892.1
See application file for complete search history.

(56) References Cited

U.S. PATENT DOCUMENTS

| | | |
|---|---|---|
| 3,480,523 A | 11/1969 | Tyrrell |
| 3,751,283 A | 8/1973 | Dawson |

(Continued)

FOREIGN PATENT DOCUMENTS

| | | |
|---|---|---|
| AT | 232704 | 3/2003 |
| AT | 288234 | 2/2005 |

(Continued)

OTHER PUBLICATIONS

US 6,533,715, 03/2003, Hossainy et al (withdrawn).

(Continued)

*Primary Examiner* — Thomas J Sweet
*Assistant Examiner* — Seema Mathew
(74) *Attorney, Agent, or Firm* — Fish & Richardson P.C.

(57) ABSTRACT

In one aspect, a medical device has a first configuration and a second configuration, a reservoir containing a therapeutic agent, and a barrier layer disposed over the reservoir, wherein the barrier layer comprises an inorganic material. In another aspect, a medical device has a reservoir containing a therapeutic agent, a barrier layer disposed over the reservoir, wherein the barrier layer comprises an inorganic material, and a swellable material disposed between the barrier layer and a surface of the medical device, wherein the swellable material is a material that swells upon exposure to an aqueous environment. In yet another aspect, a medical device has a multi-layered coating having alternating reservoir layers and barrier layers, and a plurality of excavated regions penetrating through at least a partial thickness of the multi-layered coating. In yet another aspect, a medical device has a polymer layer comprising a block co-polymer, wherein the polymer layer contains a therapeutic agent, and a barrier layer disposed over the polymer layer, wherein the barrier layer comprises an inorganic material, and wherein the barrier layer has a plurality of discontinuities. Methods of forming coatings on medical devices and methods of delivering therapeutic agents to body sites are also disclosed.

40 Claims, 13 Drawing Sheets

(56) References Cited

U.S. PATENT DOCUMENTS

| | | | |
|---|---|---|---|
| 3,758,396 A | 9/1973 | Vieth et al. | |
| 3,910,819 A | 10/1975 | Rembaum et al. | |
| 3,948,254 A | 4/1976 | Zaffaroni | |
| 3,952,334 A | 4/1976 | Bokros et al. | |
| 3,970,445 A | 7/1976 | Gale et al. | |
| 3,993,072 A | 11/1976 | Zaffaroni | |
| 4,044,404 A | 8/1977 | Martin et al. | |
| 4,101,984 A | 7/1978 | MacGregor | |
| 4,143,661 A | 3/1979 | LaForge et al. | |
| 4,202,055 A | 5/1980 | Reiner et al. | |
| 4,237,559 A | 12/1980 | Borom | |
| 4,286,341 A * | 9/1981 | Greer et al. | 623/1.4 |
| 4,308,868 A | 1/1982 | Jhabvala | |
| 4,309,996 A * | 1/1982 | Theeuwes | 604/892.1 |
| 4,321,311 A | 3/1982 | Strangman | |
| 4,330,891 A | 5/1982 | Branemark et al. | |
| 4,334,327 A | 6/1982 | Lyman et al. | |
| 4,401,546 A | 8/1983 | Nakamura et al. | |
| 4,407,695 A | 10/1983 | Deckman et al. | |
| 4,475,972 A | 10/1984 | Wong | |
| 4,565,744 A | 1/1986 | Walter et al. | |
| 4,585,652 A | 4/1986 | Miller et al. | |
| 4,627,851 A * | 12/1986 | Wong et al. | 424/467 |
| 4,655,771 A | 4/1987 | Wallsten | |
| 4,657,544 A | 4/1987 | Pinchuk | |
| 4,665,896 A | 5/1987 | LaForge et al. | |
| 4,705,502 A | 11/1987 | Patel | |
| 4,733,665 A | 3/1988 | Palmaz | |
| 4,738,740 A | 4/1988 | Pinchuk et al. | |
| 4,743,252 A | 5/1988 | Martin et al. | |
| 4,784,659 A | 11/1988 | Fleckenstein et al. | |
| 4,800,882 A | 1/1989 | Gianturco | |
| 4,842,505 A | 6/1989 | Annis et al. | |
| 4,886,062 A | 12/1989 | Wiktor | |
| 4,902,290 A | 2/1990 | Fleckenstein et al. | |
| 4,954,126 A | 9/1990 | Wallsten | |
| 4,976,692 A | 12/1990 | Atad | |
| 4,994,071 A | 2/1991 | MacGregor | |
| 5,061,275 A | 10/1991 | Wallsten et al. | |
| 5,061,914 A | 10/1991 | Busch et al. | |
| 5,073,365 A | 12/1991 | Katz et al. | |
| 5,091,205 A | 2/1992 | Fan | |
| 5,102,403 A | 4/1992 | Alt | |
| 5,120,322 A | 6/1992 | Davis et al. | |
| 5,125,971 A | 6/1992 | Nonami et al. | |
| 5,147,370 A | 9/1992 | McNamara et al. | |
| 5,163,958 A | 11/1992 | Pinchuk | |
| 5,171,607 A | 12/1992 | Cumbo | |
| 5,195,969 A | 3/1993 | Wang et al. | |
| 5,205,921 A | 4/1993 | Shirkanzadeh | |
| 5,219,611 A | 6/1993 | Giannelis et al. | |
| 5,232,444 A | 8/1993 | Just et al. | |
| 5,236,413 A | 8/1993 | Feiring | |
| 5,242,706 A | 9/1993 | Cotell et al. | |
| 5,250,242 A | 10/1993 | Nishio et al. | |
| 5,270,086 A | 12/1993 | Hamlin | |
| 5,279,292 A | 1/1994 | Baumann et al. | |
| 5,290,585 A | 3/1994 | Elton | |
| 5,302,414 A | 4/1994 | Alkhimov et al. | |
| 5,304,121 A | 4/1994 | Sahatjian | |
| 5,314,453 A | 5/1994 | Jeutter | |
| 5,322,520 A | 6/1994 | Milder | |
| 5,326,354 A | 7/1994 | Kwarteng | |
| 5,348,553 A | 9/1994 | Whitney | |
| 5,366,504 A | 11/1994 | Andersen et al. | |
| 5,368,881 A | 11/1994 | Kelman et al. | |
| 5,378,146 A | 1/1995 | Sterrett | |
| 5,380,298 A | 1/1995 | Zabetakis et al. | |
| 5,383,935 A | 1/1995 | Shirkhanzadeh | |
| 5,397,307 A | 3/1995 | Goodin | |
| 5,405,367 A | 4/1995 | Schulman et al. | |
| 5,439,446 A | 8/1995 | Barry | |
| 5,443,496 A | 8/1995 | Schwartz et al. | |
| 5,447,724 A | 9/1995 | Helmus et al. | |
| 5,449,373 A | 9/1995 | Pinchasik et al. | |
| 5,449,382 A | 9/1995 | Dayton | |
| 5,464,450 A | 11/1995 | Buscemi et al. | |
| 5,464,650 A | 11/1995 | Berg et al. | |
| 5,474,797 A | 12/1995 | Sioshansi et al. | |
| 5,500,013 A | 3/1996 | Buscemi et al. | |
| 5,527,337 A | 6/1996 | Stack et al. | |
| 5,545,208 A | 8/1996 | Wolff et al. | |
| 5,551,954 A | 9/1996 | Buscemi et al. | |
| 5,567,489 A * | 10/1996 | Allen et al. | 428/34.1 |
| 5,569,463 A | 10/1996 | Helmus et al. | |
| 5,578,075 A | 11/1996 | Dayton | |
| 5,587,507 A | 12/1996 | Kohn et al. | |
| 5,591,224 A | 1/1997 | Schwartz et al. | |
| 5,603,556 A | 2/1997 | Klink | |
| 5,605,696 A | 2/1997 | Eury et al. | |
| 5,607,463 A | 3/1997 | Schwartz et al. | |
| 5,607,467 A | 3/1997 | Froix | |
| 5,609,629 A | 3/1997 | Fearnot et al. | |
| 5,614,549 A | 3/1997 | Greenwald et al. | |
| 5,624,411 A | 4/1997 | Tuch | |
| 5,649,951 A | 7/1997 | Davidson | |
| 5,649,977 A | 7/1997 | Campbell | |
| 5,672,242 A | 9/1997 | Jen | |
| 5,674,192 A | 10/1997 | Sahatjian et al. | |
| 5,674,242 A | 10/1997 | Phan et al. | |
| 5,679,440 A | 10/1997 | Kubota | |
| 5,681,196 A | 10/1997 | Jin et al. | |
| 5,681,579 A * | 10/1997 | Freeman | 424/448 |
| 5,690,670 A | 11/1997 | Davidson | |
| 5,693,085 A | 12/1997 | Buirge et al. | |
| 5,693,928 A | 12/1997 | Egitto et al. | |
| 5,711,866 A | 1/1998 | Lashmore et al. | |
| 5,733,924 A | 3/1998 | Kanda et al. | |
| 5,733,925 A | 3/1998 | Kunz et al. | |
| 5,741,331 A | 4/1998 | Pinchuk | |
| 5,744,515 A | 4/1998 | Clapper | |
| 5,749,809 A | 5/1998 | Lin | |
| 5,758,562 A | 6/1998 | Thompson | |
| 5,761,775 A | 6/1998 | Legome et al. | |
| 5,769,883 A | 6/1998 | Buscemi et al. | |
| 5,772,864 A | 6/1998 | Moller et al. | |
| 5,776,184 A | 7/1998 | Tuch | |
| 5,780,807 A | 7/1998 | Saunders | |
| 5,788,687 A | 8/1998 | Batich et al. | |
| 5,788,979 A | 8/1998 | Alt et al. | |
| 5,795,626 A | 8/1998 | Gabel et al. | |
| 5,797,898 A | 8/1998 | Santini, Jr. et al. | |
| 5,807,407 A | 9/1998 | England et al. | |
| 5,817,046 A | 10/1998 | Glickman | |
| 5,824,045 A | 10/1998 | Alt | |
| 5,824,048 A | 10/1998 | Tuch | |
| 5,824,049 A | 10/1998 | Ragheb et al. | |
| 5,824,077 A | 10/1998 | Mayer | |
| 5,830,480 A | 11/1998 | Ducheyne et al. | |
| 5,837,313 A | 11/1998 | Ding et al. | |
| 5,843,089 A | 12/1998 | Sahatjian et al. | |
| 5,843,172 A | 12/1998 | Yan | |
| 5,852,088 A | 12/1998 | Dismukes et al. | |
| 5,858,556 A | 1/1999 | Eckert et al. | |
| 5,873,904 A | 2/1999 | Ragheb et al. | |
| 5,874,134 A | 2/1999 | Rao et al. | |
| 5,879,697 A | 3/1999 | Ding et al. | |
| 5,882,335 A | 3/1999 | Leone et al. | |
| 5,888,591 A | 3/1999 | Gleason et al. | |
| 5,891,108 A | 4/1999 | Leone et al. | |
| 5,891,192 A | 4/1999 | Murayama et al. | |
| 5,902,266 A | 5/1999 | Leone et al. | |
| 5,922,021 A | 7/1999 | Jang | |
| 5,928,247 A | 7/1999 | Barry et al. | |
| 5,951,881 A | 9/1999 | Rogers et al. | |
| 5,954,706 A | 9/1999 | Sahatjian | |
| 5,962,136 A | 10/1999 | Dewez et al. | |
| 5,968,091 A | 10/1999 | Pinchuk et al. | |
| 5,968,092 A | 10/1999 | Buscemi et al. | |
| 5,968,640 A | 10/1999 | Lubowitz et al. | |
| 5,972,027 A | 10/1999 | Johnson | |
| 5,977,204 A | 11/1999 | Boyan et al. | |
| 5,980,551 A | 11/1999 | Summers et al. | |
| 5,980,564 A | 11/1999 | Stinson | |

| | | | |
|---|---|---|---|
| 5,980,566 | A | 11/1999 | Alt et al. |
| 6,007,837 | A * | 12/1999 | Enscore et al. ............... 424/449 |
| 6,013,591 | A | 1/2000 | Ying et al. |
| 6,017,577 | A | 1/2000 | Hostettler et al. |
| 6,022,812 | A | 2/2000 | Smith et al. |
| 6,025,036 | A | 2/2000 | McGill et al. |
| 6,034,295 | A | 3/2000 | Rehberg et al. |
| 6,045,877 | A | 4/2000 | Gleason et al. |
| 6,063,101 | A | 5/2000 | Jacobsen et al. |
| 6,071,305 | A | 6/2000 | Brown et al. |
| 6,074,135 | A | 6/2000 | Tapphorn et al. |
| 6,096,070 | A | 8/2000 | Ragheb et al. |
| 6,099,561 | A | 8/2000 | Alt |
| 6,099,562 | A | 8/2000 | Ding et al. |
| 6,106,473 | A | 8/2000 | Violante et al. |
| 6,110,204 | A | 8/2000 | Lazarov et al. |
| 6,110,479 | A * | 8/2000 | Blaney et al. ............... 424/402 |
| 6,120,536 | A | 9/2000 | Ding et al. |
| 6,120,660 | A | 9/2000 | Chu et al. |
| 6,122,564 | A | 9/2000 | Koch et al. |
| 6,139,573 | A | 10/2000 | Sogard et al. |
| 6,139,913 | A | 10/2000 | Van Steenkiste et al. |
| 6,153,252 | A | 11/2000 | Hossainy et al. |
| 6,156,435 | A | 12/2000 | Gleason et al. |
| 6,159,142 | A | 12/2000 | Alt |
| 6,171,609 | B1 | 1/2001 | Kunz |
| 6,174,329 | B1 | 1/2001 | Callol et al. |
| 6,174,330 | B1 | 1/2001 | Stinson |
| 6,180,184 | B1 | 1/2001 | Gray et al. |
| 6,187,037 | B1 | 2/2001 | Satz |
| 6,190,404 | B1 | 2/2001 | Palmaz et al. |
| 6,193,761 | B1 | 2/2001 | Treacy |
| 6,200,685 | B1 | 3/2001 | Davidson |
| 6,203,536 | B1 | 3/2001 | Berg et al. |
| 6,206,915 | B1 | 3/2001 | Fagan et al. |
| 6,206,916 | B1 | 3/2001 | Furst |
| 6,210,715 | B1 | 4/2001 | Starling et al. |
| 6,212,434 | B1 | 4/2001 | Scheiner et al. |
| 6,214,042 | B1 | 4/2001 | Jacobsen et al. |
| 6,217,607 | B1 | 4/2001 | Alt |
| 6,231,600 | B1 | 5/2001 | Zhong |
| 6,240,616 | B1 | 6/2001 | Yan |
| 6,241,762 | B1 | 6/2001 | Shanley |
| 6,245,104 | B1 | 6/2001 | Alt |
| 6,249,952 | B1 | 6/2001 | Ding |
| 6,251,136 | B1 | 6/2001 | Guruwaiya et al. |
| 6,253,443 | B1 | 7/2001 | Johnson |
| 6,254,632 | B1 | 7/2001 | Wu et al. |
| 6,270,831 | B2 | 8/2001 | Kumar et al. |
| 6,273,908 | B1 | 8/2001 | Ndondo-Lay |
| 6,273,913 | B1 | 8/2001 | Wright et al. |
| 6,280,411 | B1 | 8/2001 | Lennox |
| 6,283,386 | B1 | 9/2001 | Van Steenkiste et al. |
| 6,284,305 | B1 | 9/2001 | Ding et al. |
| 6,287,331 | B1 | 9/2001 | Heath |
| 6,287,332 | B1 | 9/2001 | Bolz et al. |
| 6,287,628 | B1 | 9/2001 | Hossainy et al. |
| 6,290,721 | B1 | 9/2001 | Heath |
| 6,299,604 | B1 | 10/2001 | Ragheb et al. |
| 6,306,144 | B1 | 10/2001 | Sydney et al. |
| 6,315,708 | B1 | 11/2001 | Salmon et al. |
| 6,315,794 | B1 | 11/2001 | Richter |
| 6,323,146 | B1 | 11/2001 | Pugh et al. |
| 6,325,825 | B1 | 12/2001 | Kula et al. |
| 6,327,504 | B1 | 12/2001 | Dolgin et al. |
| 6,331,330 | B1 | 12/2001 | Choy et al. |
| 6,334,856 | B1 | 1/2002 | Allen et al. |
| 6,335,029 | B1 | 1/2002 | Kamath et al. |
| 6,337,076 | B1 | 1/2002 | Studin |
| 6,342,507 | B1 | 1/2002 | Naicker et al. |
| 6,348,960 | B1 | 2/2002 | Etori et al. |
| 6,358,532 | B2 | 3/2002 | Starling et al. |
| 6,358,556 | B1 | 3/2002 | Ding et al. |
| 6,361,780 | B1 | 3/2002 | Ley et al. |
| 6,364,856 | B1 | 4/2002 | Ding et al. |
| 6,365,222 | B1 | 4/2002 | Wagner et al. |
| 6,367,412 | B1 | 4/2002 | Ramaswamy et al. |
| 6,368,658 | B1 | 4/2002 | Schwarz et al. |
| 6,379,381 | B1 | 4/2002 | Hossainy et al. |
| 6,379,383 | B1 | 4/2002 | Palmaz et al. |
| 6,387,121 | B1 | 5/2002 | Alt |
| 6,387,124 | B1 | 5/2002 | Buscemi et al. |
| 6,390,967 | B1 | 5/2002 | Forman et al. |
| 6,391,052 | B2 | 5/2002 | Bulrge et al. |
| 6,395,325 | B1 | 5/2002 | Hedge et al. |
| 6,395,326 | B1 | 5/2002 | Castro et al. |
| 6,398,806 | B1 | 6/2002 | You |
| 6,413,271 | B1 | 7/2002 | Hafeli et al. |
| 6,416,820 | B1 | 7/2002 | Yamada et al. |
| 6,419,692 | B1 | 7/2002 | Yang et al. |
| 6,436,133 | B1 | 8/2002 | Furst et al. |
| 6,440,503 | B1 | 8/2002 | Merdan et al. |
| 6,458,153 | B1 | 10/2002 | Bailey et al. |
| 6,465,052 | B1 | 10/2002 | Wu |
| 6,468,304 | B1 | 10/2002 | Dubois-Rande et al. |
| 6,471,721 | B1 | 10/2002 | Dang |
| 6,471,980 | B2 | 10/2002 | Sirhan et al. |
| 6,475,477 | B1 | 11/2002 | Kohn et al. |
| 6,478,815 | B1 | 11/2002 | Alt |
| 6,479,418 | B2 | 11/2002 | Li et al. |
| 6,488,715 | B1 | 12/2002 | Pope et al. |
| 6,491,666 | B1 | 12/2002 | Santini, Jr. et al. |
| 6,491,720 | B1 | 12/2002 | Vallana et al. |
| 6,503,921 | B2 | 1/2003 | Naicker et al. |
| 6,504,292 | B1 | 1/2003 | Choi et al. |
| 6,506,437 | B1 | 1/2003 | Harish et al. |
| 6,506,972 | B1 | 1/2003 | Wang |
| 6,514,283 | B2 | 2/2003 | DiMatteo et al. |
| 6,514,289 | B1 | 2/2003 | Pope et al. |
| 6,517,888 | B1 | 2/2003 | Weber |
| 6,524,274 | B1 | 2/2003 | Rosenthal et al. |
| 6,527,801 | B1 | 3/2003 | Dutta |
| 6,527,938 | B2 | 3/2003 | Bales et al. |
| 6,530,951 | B1 | 3/2003 | Bates et al. |
| 6,537,310 | B1 | 3/2003 | Palmaz et al. |
| 6,544,582 | B1 | 4/2003 | Yoe |
| 6,545,097 | B2 | 4/2003 | Pinchuk et al. |
| 6,551,353 | B1 | 4/2003 | Baker et al. |
| 6,558,422 | B1 | 5/2003 | Baker et al. |
| 6,558,733 | B1 | 5/2003 | Hossainy et al. |
| 6,565,602 | B2 | 5/2003 | Rolando et al. |
| 6,569,489 | B1 | 5/2003 | Li |
| 6,585,765 | B1 | 7/2003 | Hossainy et al. |
| 6,599,558 | B1 | 7/2003 | Al-Lamee et al. |
| 6,607,598 | B2 | 8/2003 | Schwarz et al. |
| 6,613,083 | B2 | 9/2003 | Alt |
| 6,613,432 | B2 | 9/2003 | Zamora et al. |
| 6,616,765 | B1 | 9/2003 | Castro et al. |
| 6,620,194 | B2 | 9/2003 | Ding et al. |
| 6,635,082 | B1 | 10/2003 | Hossainy et al. |
| 6,638,302 | B1 | 10/2003 | Curcio et al. |
| 6,641,607 | B1 | 11/2003 | Hossainy et al. |
| 6,652,575 | B2 | 11/2003 | Wang |
| 6,652,578 | B2 | 11/2003 | Bailey et al. |
| 6,652,581 | B1 | 11/2003 | Ding |
| 6,652,582 | B1 | 11/2003 | Stinson |
| 6,656,506 | B1 | 12/2003 | Wu et al. |
| 6,660,034 | B1 | 12/2003 | Mandrusov et al. |
| 6,660,343 | B2 | 12/2003 | McGill et al. |
| 6,663,662 | B2 | 12/2003 | Pacetti et al. |
| 6,663,664 | B1 | 12/2003 | Pacetti |
| 6,669,980 | B2 | 12/2003 | Hansen |
| 6,673,105 | B1 | 1/2004 | Chen |
| 6,673,999 | B1 | 1/2004 | Wang et al. |
| 6,676,987 | B2 | 1/2004 | Zhong et al. |
| 6,676,989 | B2 | 1/2004 | Kirkpatrick et al. |
| 6,689,803 | B2 | 2/2004 | Hunter |
| 6,695,865 | B2 | 2/2004 | Boyle et al. |
| 6,699,281 | B2 | 3/2004 | Vallana et al. |
| 6,699,282 | B2 | 3/2004 | Sceusa |
| 6,709,379 | B1 | 3/2004 | Brandau et al. |
| 6,709,397 | B2 | 3/2004 | Taylor |
| 6,709,451 | B1 | 3/2004 | Noble et al. |
| 6,710,053 | B2 | 3/2004 | Naicker et al. |
| 6,712,844 | B2 | 3/2004 | Pacetti |
| 6,712,845 | B2 | 3/2004 | Hossainy |
| 6,713,671 | B1 | 3/2004 | Wang et al. |

| | | |
|---|---|---|
| 6,716,444 B1 | 4/2004 | Castro et al. |
| 6,723,120 B2 | 4/2004 | Yan |
| 6,725,901 B1 | 4/2004 | Kramer et al. |
| 6,726,712 B1 | 4/2004 | Raeder-Devens et al. |
| 6,730,120 B2 | 5/2004 | Berg et al. |
| 6,730,699 B2 | 5/2004 | Li et al. |
| 6,733,513 B2 | 5/2004 | Boyle et al. |
| 6,736,849 B2 | 5/2004 | Li et al. |
| 6,740,077 B1 | 5/2004 | Brandau et al. |
| 6,752,826 B2 | 6/2004 | Holloway et al. |
| 6,752,829 B2 | 6/2004 | Kocur et al. |
| 6,753,071 B1 | 6/2004 | Pacetti |
| 6,758,859 B1 | 7/2004 | Dang et al. |
| 6,761,736 B1 | 7/2004 | Woo et al. |
| 6,764,505 B1 | 7/2004 | Hossainy et al. |
| 6,764,579 B2 | 7/2004 | Veerasamy et al. |
| 6,764,709 B2 | 7/2004 | Flanagan |
| 6,765,144 B1 | 7/2004 | Wang et al. |
| 6,767,360 B1 | 7/2004 | Alt et al. |
| 6,774,278 B1 | 8/2004 | Ragheb et al. |
| 6,776,022 B2 | 8/2004 | Kula et al. |
| 6,776,094 B1 | 8/2004 | Whitesides et al. |
| 6,780,424 B2 | 8/2004 | Claude |
| 6,780,491 B1 | 8/2004 | Cathey et al. |
| 6,783,543 B2 | 8/2004 | Jang |
| 6,790,228 B2 * | 9/2004 | Hossainy et al. ............ 623/1.46 |
| 6,803,070 B2 | 10/2004 | Weber |
| 6,805,709 B1 | 10/2004 | Schaldach et al. |
| 6,805,898 B1 | 10/2004 | Wu et al. |
| 6,807,440 B2 | 10/2004 | Weber |
| 6,815,609 B1 | 11/2004 | Wang et al. |
| 6,820,676 B2 | 11/2004 | Palmaz et al. |
| 6,827,737 B2 | 12/2004 | Hill et al. |
| 6,830,598 B1 | 12/2004 | Sung |
| 6,833,004 B2 | 12/2004 | Ishii et al. |
| 6,846,323 B2 | 1/2005 | Yip et al. |
| 6,846,841 B2 | 1/2005 | Hunter et al. |
| 6,849,085 B2 | 2/2005 | Marton |
| 6,849,089 B2 | 2/2005 | Stoll |
| 6,852,122 B2 | 2/2005 | Rush |
| 6,858,221 B2 | 2/2005 | Sirhan et al. |
| 6,861,088 B2 | 3/2005 | Weber et al. |
| 6,861,729 B2 | 3/2005 | Kozaki et al. |
| 6,866,805 B2 | 3/2005 | Hong et al. |
| 6,869,443 B2 | 3/2005 | Buscemi et al. |
| 6,869,701 B1 | 3/2005 | Aita et al. |
| 6,875,227 B2 | 4/2005 | Yoon |
| 6,878,249 B2 | 4/2005 | Kouyama et al. |
| 6,884,429 B2 | 4/2005 | Koziak et al. |
| 6,896,697 B1 | 5/2005 | Yip et al. |
| 6,899,914 B2 | 5/2005 | Schaldach et al. |
| 6,904,658 B2 | 6/2005 | Hines |
| 6,908,622 B2 | 6/2005 | Barry et al. |
| 6,908,624 B2 | 6/2005 | Hossainy et al. |
| 6,913,617 B1 | 7/2005 | Reiss |
| 6,915,796 B2 | 7/2005 | Sung |
| 6,918,927 B2 | 7/2005 | Bates et al. |
| 6,918,929 B2 | 7/2005 | Udipi et al. |
| 6,923,829 B2 | 8/2005 | Boyle et al. |
| 6,924,004 B2 | 8/2005 | Rao et al. |
| 6,932,930 B2 | 8/2005 | DeSimone et al. |
| 6,936,066 B2 | 8/2005 | Palmaz et al. |
| 6,939,320 B2 | 9/2005 | Lennox |
| 6,951,053 B2 | 10/2005 | Padilla et al. |
| 6,953,560 B1 * | 10/2005 | Castro et al. ................ 423/423 |
| 6,955,661 B1 | 10/2005 | Herweck et al. |
| 6,955,685 B2 | 10/2005 | Escamilla et al. |
| 6,962,822 B2 | 11/2005 | Hart et al. |
| 6,971,813 B2 | 12/2005 | Shekalim et al. |
| 6,973,718 B2 | 12/2005 | Sheppard, Jr. et al. |
| 6,979,346 B1 | 12/2005 | Hossainy et al. |
| 6,979,348 B2 | 12/2005 | Sundar |
| 6,984,404 B1 | 1/2006 | Talton et al. |
| 6,991,804 B2 | 1/2006 | Helmus et al. |
| 7,001,421 B2 | 2/2006 | Cheng et al. |
| 7,011,680 B2 | 3/2006 | Alt |
| 7,014,654 B2 | 3/2006 | Welsh et al. |
| 7,018,408 B2 | 3/2006 | Bailey et al. |
| 7,041,130 B2 | 5/2006 | Santini, Jr. et al. |
| 7,048,939 B2 | 5/2006 | Elkins et al. |
| 7,052,488 B2 | 5/2006 | Uhland |
| 7,056,338 B2 | 6/2006 | Shanley et al. |
| 7,056,339 B2 | 6/2006 | Elkins et al. |
| 7,056,591 B1 | 6/2006 | Pacetti et al. |
| 7,060,051 B2 | 6/2006 | Palasis |
| 7,063,748 B2 | 6/2006 | Talton |
| 7,066,234 B2 | 6/2006 | Sawitowski |
| 7,077,859 B2 | 7/2006 | Sirhan et al. |
| 7,078,108 B2 | 7/2006 | Zhang et al. |
| 7,083,642 B2 | 8/2006 | Sirhan et al. |
| 7,087,661 B1 | 8/2006 | Alberte et al. |
| 7,099,091 B2 | 8/2006 | Taniguchi et al. |
| 7,101,391 B2 | 9/2006 | Scheuermann et al. |
| 7,101,394 B2 | 9/2006 | Hamm et al. |
| 7,105,018 B1 | 9/2006 | Yip et al. |
| 7,105,199 B2 | 9/2006 | Blinn et al. |
| 7,144,840 B2 | 12/2006 | Yeung et al. |
| 7,153,411 B2 | 12/2006 | Larson et al. |
| 7,160,592 B2 | 1/2007 | Rypacek et al. |
| 7,163,715 B1 | 1/2007 | Kramer |
| 7,169,177 B2 | 1/2007 | Obara |
| 7,169,178 B1 | 1/2007 | Santos et al. |
| 7,195,640 B2 | 3/2007 | Falotico et al. |
| 7,195,641 B2 | 3/2007 | Palmaz et al. |
| 7,198,675 B2 | 4/2007 | Fox et al. |
| 7,208,010 B2 | 4/2007 | Shanley et al. |
| 7,208,011 B2 | 4/2007 | Shanley et al. |
| 7,208,172 B2 | 4/2007 | Birdsall et al. |
| 7,208,190 B2 | 4/2007 | Verlee et al. |
| 7,229,471 B2 | 6/2007 | Gale et al. |
| 7,235,096 B1 | 6/2007 | Van Tassel et al. |
| 7,235,098 B2 | 6/2007 | Palmaz |
| 7,238,199 B2 | 7/2007 | Feldman et al. |
| 7,244,272 B2 | 7/2007 | Dubson et al. |
| 7,247,166 B2 | 7/2007 | Pienknagura |
| 7,247,338 B2 | 7/2007 | Pui et al. |
| 7,261,735 B2 | 8/2007 | Llanos et al. |
| 7,261,752 B2 | 8/2007 | Sung |
| 7,273,493 B2 | 9/2007 | Ledergerber |
| 7,294,409 B2 | 11/2007 | Lye et al. |
| 7,311,727 B2 | 12/2007 | Mazumder et al. |
| 7,329,431 B2 | 2/2008 | Ishii |
| 7,344,563 B2 | 3/2008 | Vallana et al. |
| 7,368,065 B2 | 5/2008 | Yang et al. |
| 7,393,589 B2 | 7/2008 | Aharonov et al. |
| 7,396,538 B2 | 7/2008 | Granada et al. |
| 7,402,173 B2 | 7/2008 | Scheuermann et al. |
| 7,416,558 B2 | 8/2008 | Yip et al. |
| 7,419,709 B2 * | 9/2008 | Rypacek et al. ............ 428/36.9 |
| 7,435,256 B2 | 10/2008 | Stenzel |
| 7,482,034 B2 | 1/2009 | Boulais |
| 7,494,950 B2 | 2/2009 | Armitage et al. |
| 7,497,876 B2 | 3/2009 | Tuke et al. |
| 7,547,445 B2 | 6/2009 | Chudzik et al. |
| 7,563,324 B1 | 7/2009 | Chen et al. |
| 7,575,593 B2 | 8/2009 | Rea et al. |
| 7,575,632 B2 | 8/2009 | Sundar |
| 7,601,382 B2 | 10/2009 | Weber et al. |
| 7,622,146 B2 * | 11/2009 | Roorda et al. ................ 427/2.1 |
| 7,635,515 B1 | 12/2009 | Sherman |
| 7,638,156 B1 | 12/2009 | Hossainy et al. |
| 7,643,885 B2 | 1/2010 | Maschke |
| 7,691,461 B1 | 4/2010 | Prabhu |
| 7,713,297 B2 | 5/2010 | Alt |
| 7,727,275 B2 | 6/2010 | Betts et al. |
| 7,749,264 B2 | 7/2010 | Gregorich et al. |
| 7,758,636 B2 | 7/2010 | Shanley et al. |
| 7,771,773 B2 | 8/2010 | Namavar |
| 7,785,653 B2 | 8/2010 | Shanley et al. |
| 7,837,726 B2 | 11/2010 | Von Oepen et al. |
| 7,901,452 B2 | 3/2011 | Gale et al. |
| 7,914,809 B2 | 3/2011 | Atanasoska et al. |
| 7,922,756 B2 | 4/2011 | Lenz et al. |
| 7,981,150 B2 * | 7/2011 | Scheuermann et al. ..... 623/1.39 |
| 7,981,441 B2 | 7/2011 | Pantelidis et al. |
| 7,989,018 B2 * | 8/2011 | McNiven et al. ............ 427/2.1 |
| 8,002,823 B2 * | 8/2011 | Kuehling ................ 623/1.46 |

| | | |
|---|---|---|
| 8,029,554 B2 * | 10/2011 | Holman et al. ............... 623/1.1 |
| 8,029,816 B2 | 10/2011 | Hossainy et al. |
| 8,066,763 B2 * | 11/2011 | Alt ............................ 623/1.45 |
| 8,353,949 B2 * | 1/2013 | Weber et al. ................ 623/1.15 |
| 8,431,149 B2 * | 4/2013 | McMorrow et al. .......... 424/426 |
| 8,449,603 B2 * | 5/2013 | Weber et al. ................ 623/1.48 |
| 8,460,367 B2 * | 6/2013 | Cottone et al. .............. 623/1.48 |
| 8,574,615 B2 * | 11/2013 | Tenney et al. ................ 424/423 |
| 2001/0001834 A1 | 5/2001 | Palmaz et al. |
| 2001/0002000 A1 | 5/2001 | Kumar et al. |
| 2001/0002435 A1 | 5/2001 | Berg et al. |
| 2001/0013166 A1 | 8/2001 | Yan |
| 2001/0014717 A1 | 8/2001 | Hossainy et al. |
| 2001/0014821 A1 | 8/2001 | Juman et al. |
| 2001/0027299 A1 | 10/2001 | Yang et al. |
| 2001/0029660 A1 | 10/2001 | Johnson |
| 2001/0032011 A1 | 10/2001 | Stanford |
| 2001/0032013 A1 | 10/2001 | Marton |
| 2001/0044651 A1 | 11/2001 | Steinke et al. |
| 2002/0000175 A1 | 1/2002 | Hintermaier et al. |
| 2002/0004060 A1 | 1/2002 | Heublein et al. |
| 2002/0007102 A1 | 1/2002 | Salmon et al. |
| 2002/0007209 A1 | 1/2002 | Schearder et al. |
| 2002/0009604 A1 | 1/2002 | Zamora et al. |
| 2002/0010505 A1 | 1/2002 | Richter |
| 2002/0016623 A1 | 2/2002 | Kula et al. |
| 2002/0016624 A1 | 2/2002 | Patterson et al. |
| 2002/0028827 A1 | 3/2002 | Naicker et al. |
| 2002/0032477 A1 | 3/2002 | Helmus et al. |
| 2002/0038146 A1 | 3/2002 | Harry |
| 2002/0042039 A1 | 4/2002 | Kim et al. |
| 2002/0051730 A1 | 5/2002 | Bodnar et al. |
| 2002/0051846 A1 | 5/2002 | Kirkpatrick et al. |
| 2002/0052288 A1 | 5/2002 | Krell et al. |
| 2002/0065553 A1 * | 5/2002 | Weber ........................ 623/1.46 |
| 2002/0072734 A1 | 6/2002 | Liedtke et al. |
| 2002/0077520 A1 | 6/2002 | Segal et al. |
| 2002/0077693 A1 | 6/2002 | Barclay et al. |
| 2002/0087123 A1 | 7/2002 | Hossainy et al. |
| 2002/0091375 A1 | 7/2002 | Sahatjian et al. |
| 2002/0095871 A1 | 7/2002 | McArdle et al. |
| 2002/0098278 A1 | 7/2002 | Bates et al. |
| 2002/0099359 A1 | 7/2002 | Santini, Jr. et al. |
| 2002/0099438 A1 | 7/2002 | Furst |
| 2002/0103527 A1 | 8/2002 | Kocur et al. |
| 2002/0103528 A1 | 8/2002 | Schaldach et al. |
| 2002/0104599 A1 | 8/2002 | Tillotson et al. |
| 2002/0121497 A1 | 9/2002 | Tomonto |
| 2002/0123801 A1 | 9/2002 | Pacetti et al. |
| 2002/0133222 A1 | 9/2002 | Das |
| 2002/0133225 A1 | 9/2002 | Gordon |
| 2002/0138100 A1 | 9/2002 | Stoll et al. |
| 2002/0138136 A1 | 9/2002 | Chandresekaran et al. |
| 2002/0138154 A1 * | 9/2002 | Li et al. ........................ 623/66.1 |
| 2002/0140137 A1 | 10/2002 | Sapieszko et al. |
| 2002/0142579 A1 | 10/2002 | Vincent et al. |
| 2002/0144757 A1 | 10/2002 | Craig et al. |
| 2002/0155212 A1 | 10/2002 | Hossainy |
| 2002/0165265 A1 | 11/2002 | Hunter et al. |
| 2002/0165600 A1 | 11/2002 | Banas et al. |
| 2002/0165607 A1 | 11/2002 | Alt |
| 2002/0167118 A1 | 11/2002 | Billiet et al. |
| 2002/0168466 A1 | 11/2002 | Tapphorn et al. |
| 2002/0169493 A1 | 11/2002 | Widenhouse et al. |
| 2002/0178570 A1 | 12/2002 | Sogard et al. |
| 2002/0182241 A1 | 12/2002 | Borenstein et al. |
| 2002/0183581 A1 | 12/2002 | Yoe et al. |
| 2002/0183682 A1 | 12/2002 | Darvish et al. |
| 2002/0187260 A1 | 12/2002 | Sheppard, Jr. et al. |
| 2002/0193336 A1 | 12/2002 | Elkins et al. |
| 2002/0193869 A1 | 12/2002 | Dang |
| 2002/0197178 A1 | 12/2002 | Yan |
| 2002/0198601 A1 | 12/2002 | Bales et al. |
| 2003/0003160 A1 | 1/2003 | Pugh et al. |
| 2003/0003220 A1 | 1/2003 | Zhong et al. |
| 2003/0004563 A1 | 1/2003 | Jackson et al. |
| 2003/0004564 A1 | 1/2003 | Elkins et al. |
| 2003/0006250 A1 | 1/2003 | Tapphorn et al. |
| 2003/0009214 A1 | 1/2003 | Shanley |
| 2003/0009233 A1 | 1/2003 | Blinn et al. |
| 2003/0018380 A1 | 1/2003 | Craig et al. |
| 2003/0018381 A1 | 1/2003 | Whitcher et al. |
| 2003/0021820 A1 | 1/2003 | Ahola et al. |
| 2003/0023300 A1 | 1/2003 | Bailey et al. |
| 2003/0028242 A1 | 2/2003 | Vallana et al. |
| 2003/0028243 A1 | 2/2003 | Bates et al. |
| 2003/0032892 A1 | 2/2003 | Erlach et al. |
| 2003/0033007 A1 | 2/2003 | Sirhan et al. |
| 2003/0044446 A1 | 3/2003 | Moro et al. |
| 2003/0047028 A1 | 3/2003 | Kunitake et al. |
| 2003/0047505 A1 | 3/2003 | Grimes et al. |
| 2003/0050687 A1 | 3/2003 | Schwade et al. |
| 2003/0059640 A1 | 3/2003 | Marton et al. |
| 2003/0060871 A1 | 3/2003 | Hill et al. |
| 2003/0060873 A1 | 3/2003 | Gertner et al. |
| 2003/0060877 A1 | 3/2003 | Falotico et al. |
| 2003/0064095 A1 | 4/2003 | Martin et al. |
| 2003/0069631 A1 | 4/2003 | Stoll |
| 2003/0074053 A1 | 4/2003 | Palmaz et al. |
| 2003/0074075 A1 | 4/2003 | Thomas et al. |
| 2003/0074081 A1 | 4/2003 | Ayers |
| 2003/0077200 A1 | 4/2003 | Craig et al. |
| 2003/0083614 A1 | 5/2003 | Eisert |
| 2003/0083646 A1 | 5/2003 | Sirhan et al. |
| 2003/0083731 A1 | 5/2003 | Kramer et al. |
| 2003/0087024 A1 | 5/2003 | Flanagan |
| 2003/0088307 A1 | 5/2003 | Shulze et al. |
| 2003/0088312 A1 | 5/2003 | Kopia et al. |
| 2003/0100865 A1 | 5/2003 | Santini, Jr. et al. |
| 2003/0104028 A1 | 6/2003 | Hossainy et al. |
| 2003/0105511 A1 | 6/2003 | Welsh et al. |
| 2003/0108659 A1 | 6/2003 | Bales et al. |
| 2003/0114917 A1 | 6/2003 | Holloway et al. |
| 2003/0114921 A1 | 6/2003 | Yoon |
| 2003/0118649 A1 | 6/2003 | Gao et al. |
| 2003/0125803 A1 | 7/2003 | Vallana et al. |
| 2003/0130206 A1 | 7/2003 | Koziak et al. |
| 2003/0130718 A1 | 7/2003 | Palmas et al. |
| 2003/0138645 A1 | 7/2003 | Gleason et al. |
| 2003/0139799 A1 | 7/2003 | Ley et al. |
| 2003/0144728 A1 | 7/2003 | Scheuermann et al. |
| 2003/0150380 A1 | 8/2003 | Yoe |
| 2003/0153901 A1 | 8/2003 | Herweck et al. |
| 2003/0153971 A1 | 8/2003 | Chandresekaran |
| 2003/0158598 A1 | 8/2003 | Ashton et al. |
| 2003/0167878 A1 | 9/2003 | Al-Salim et al. |
| 2003/0170605 A1 | 9/2003 | Long et al. |
| 2003/0181975 A1 | 9/2003 | Ishii et al. |
| 2003/0185895 A1 | 10/2003 | Lanphere et al. |
| 2003/0185964 A1 | 10/2003 | Weber et al. |
| 2003/0190406 A1 | 10/2003 | Hossainy et al. |
| 2003/0195613 A1 | 10/2003 | Curcio et al. |
| 2003/0203991 A1 | 10/2003 | Schottman et al. |
| 2003/0204168 A1 | 10/2003 | Bosma et al. |
| 2003/0208256 A1 | 11/2003 | DiMatteo et al. |
| 2003/0211135 A1 | 11/2003 | Greenhalgh et al. |
| 2003/0216803 A1 | 11/2003 | Ledergerber |
| 2003/0216806 A1 | 11/2003 | Togawa et al. |
| 2003/0219562 A1 | 11/2003 | Rypacek et al. |
| 2003/0225450 A1 | 12/2003 | Shulze et al. |
| 2003/0236323 A1 | 12/2003 | Ratner et al. |
| 2003/0236514 A1 | 12/2003 | Schwarz |
| 2004/0000540 A1 | 1/2004 | Soboyejo et al. |
| 2004/0002755 A1 | 1/2004 | Fischell et al. |
| 2004/0006382 A1 | 1/2004 | Sohier |
| 2004/0013873 A1 | 1/2004 | Wendorff et al. |
| 2004/0016651 A1 | 1/2004 | Windler |
| 2004/0018296 A1 | 1/2004 | Castro et al. |
| 2004/0019376 A1 | 1/2004 | Alt |
| 2004/0022824 A1 | 2/2004 | Li et al. |
| 2004/0026811 A1 | 2/2004 | Murphy et al. |
| 2004/0028875 A1 | 2/2004 | Van Rijn et al. |
| 2004/0029303 A1 | 2/2004 | Hart et al. |
| 2004/0029706 A1 | 2/2004 | Barrera et al. |
| 2004/0030218 A1 | 2/2004 | Kocur et al. |
| 2004/0030377 A1 | 2/2004 | Dubson et al. |
| 2004/0039438 A1 | 2/2004 | Alt |

| | | | |
|---|---|---|---|
| 2004/0039441 A1 | 2/2004 | Rowland et al. | |
| 2004/0044397 A1 | 3/2004 | Stinson | |
| 2004/0047980 A1 | 3/2004 | Pacetti et al. | |
| 2004/0052861 A1 | 3/2004 | Hatcher et al. | |
| 2004/0058858 A1 | 3/2004 | Hu | |
| 2004/0059290 A1 | 3/2004 | Palasis | |
| 2004/0059407 A1 | 3/2004 | Escamilla et al. | |
| 2004/0059409 A1 | 3/2004 | Stenzel | |
| 2004/0067301 A1 | 4/2004 | Ding | |
| 2004/0071861 A1 | 4/2004 | Mandrusov et al. | |
| 2004/0073284 A1 | 4/2004 | Bates et al. | |
| 2004/0073298 A1 | 4/2004 | Hossainy | |
| 2004/0078071 A1 | 4/2004 | Escamilla et al. | |
| 2004/0086674 A1 | 5/2004 | Holman | |
| 2004/0088038 A1 | 5/2004 | Dehnad et al. | |
| 2004/0088041 A1 | 5/2004 | Stanford | |
| 2004/0092653 A1 | 5/2004 | Ruberti et al. | |
| 2004/0093071 A1 | 5/2004 | Jang | |
| 2004/0093076 A1 | 5/2004 | White et al. | |
| 2004/0093089 A1 | 5/2004 | Weber | |
| 2004/0098119 A1 | 5/2004 | Wang | |
| 2004/0102758 A1 | 5/2004 | Davila et al. | |
| 2004/0106984 A1 | 6/2004 | Stinson | |
| 2004/0106985 A1 | 6/2004 | Jang | |
| 2004/0106987 A1 | 6/2004 | Palasis et al. | |
| 2004/0106994 A1 | 6/2004 | De Maeztus Martinez et al. | |
| 2004/0111150 A1 | 6/2004 | Berg et al. | |
| 2004/0116999 A1 | 6/2004 | Ledergerber | |
| 2004/0117005 A1 | 6/2004 | Nagarada Gadde et al. | |
| 2004/0117008 A1 | 6/2004 | Wnendt et al. | |
| 2004/0122504 A1 | 6/2004 | Hogendijk | |
| 2004/0126566 A1 | 7/2004 | Axen et al. | |
| 2004/0133270 A1 | 7/2004 | Grandt | |
| 2004/0134886 A1 | 7/2004 | Wagner et al. | |
| 2004/0142014 A1 | 7/2004 | Litvack et al. | |
| 2004/0143317 A1 | 7/2004 | Stinson et al. | |
| 2004/0143321 A1 | 7/2004 | Litvack et al. | |
| 2004/0148010 A1 | 7/2004 | Rush | |
| 2004/0148015 A1 | 7/2004 | Lye et al. | |
| 2004/0158308 A1 | 8/2004 | Hogendijk et al. | |
| 2004/0167572 A1 | 8/2004 | Roth et al. | |
| 2004/0167612 A1 | 8/2004 | Grignani et al. | |
| 2004/0171978 A1 | 9/2004 | Shalaby | |
| 2004/0172124 A1 | 9/2004 | Vallana et al. | |
| 2004/0178523 A1 | 9/2004 | Kim et al. | |
| 2004/0181252 A1 | 9/2004 | Boyle et al. | |
| 2004/0181275 A1 | 9/2004 | Noble et al. | |
| 2004/0181276 A1 | 9/2004 | Brown et al. | |
| 2004/0185168 A1 | 9/2004 | Weber et al. | |
| 2004/0191293 A1 | 9/2004 | Claude | |
| 2004/0191404 A1 | 9/2004 | Hossainy et al. | |
| 2004/0202692 A1 | 10/2004 | Shanley et al. | |
| 2004/0204750 A1 | 10/2004 | Dinh | |
| 2004/0211362 A1 | 10/2004 | Castro et al. | |
| 2004/0215169 A1 | 10/2004 | Li | |
| 2004/0215313 A1 * | 10/2004 | Cheng | 623/1.11 |
| 2004/0219214 A1 | 11/2004 | Gravett et al. | |
| 2004/0220510 A1 | 11/2004 | Koullick et al. | |
| 2004/0220662 A1 | 11/2004 | Dang et al. | |
| 2004/0224001 A1 | 11/2004 | Pacetti et al. | |
| 2004/0225346 A1 | 11/2004 | Mazumder et al. | |
| 2004/0225347 A1 | 11/2004 | Lang | |
| 2004/0228905 A1 | 11/2004 | Greenspan et al. | |
| 2004/0230176 A1 | 11/2004 | Shanahan et al. | |
| 2004/0230290 A1 | 11/2004 | Weber et al. | |
| 2004/0232047 A1 | 11/2004 | Yip et al. | |
| 2004/0234737 A1 | 11/2004 | Pacetti | |
| 2004/0234748 A1 | 11/2004 | Stenzel | |
| 2004/0236399 A1 | 11/2004 | Sundar | |
| 2004/0236415 A1 | 11/2004 | Thomas | |
| 2004/0236416 A1 | 11/2004 | Falotico | |
| 2004/0237282 A1 | 12/2004 | Hines | |
| 2004/0242106 A1 | 12/2004 | Rabasco et al. | |
| 2004/0243217 A1 | 12/2004 | Andersen et al. | |
| 2004/0243241 A1 | 12/2004 | Istephanous | |
| 2004/0247671 A1 | 12/2004 | Prescott et al. | |
| 2004/0249444 A1 | 12/2004 | Reiss | |
| 2004/0249449 A1 | 12/2004 | Shanley et al. | |
| 2004/0254635 A1 | 12/2004 | Shanley et al. | |
| 2004/0261702 A1 | 12/2004 | Grabowy et al. | |
| 2005/0002865 A1 | 1/2005 | Klaveness et al. | |
| 2005/0004663 A1 | 1/2005 | Llanos et al. | |
| 2005/0010275 A1 | 1/2005 | Sahatjian et al. | |
| 2005/0015142 A1 | 1/2005 | Austin et al. | |
| 2005/0019265 A1 | 1/2005 | Hammer et al. | |
| 2005/0019371 A1 | 1/2005 | Anderson et al. | |
| 2005/0020614 A1 | 1/2005 | Prescott et al. | |
| 2005/0021127 A1 | 1/2005 | Kawula | |
| 2005/0021128 A1 | 1/2005 | Nakahama et al. | |
| 2005/0027350 A1 | 2/2005 | Momma et al. | |
| 2005/0033411 A1 | 2/2005 | Wu et al. | |
| 2005/0033412 A1 | 2/2005 | Wu et al. | |
| 2005/0033417 A1 | 2/2005 | Borges et al. | |
| 2005/0037047 A1 | 2/2005 | Song | |
| 2005/0038498 A1 | 2/2005 | Dubrow et al. | |
| 2005/0042288 A1 | 2/2005 | Koblish et al. | |
| 2005/0055078 A1 * | 3/2005 | Campbell | 623/1.11 |
| 2005/0055080 A1 | 3/2005 | Istephanous et al. | |
| 2005/0055085 A1 | 3/2005 | Rivron et al. | |
| 2005/0060020 A1 | 3/2005 | Jenson | |
| 2005/0060021 A1 | 3/2005 | O'Brien et al. | |
| 2005/0069630 A1 | 3/2005 | Fox et al. | |
| 2005/0070989 A1 | 3/2005 | Lye et al. | |
| 2005/0070990 A1 | 3/2005 | Stinson | |
| 2005/0070996 A1 | 3/2005 | Dinh et al. | |
| 2005/0072544 A1 | 4/2005 | Palmaz et al. | |
| 2005/0074479 A1 | 4/2005 | Weber et al. | |
| 2005/0074545 A1 | 4/2005 | Thomas | |
| 2005/0077305 A1 | 4/2005 | Guevara | |
| 2005/0079199 A1 | 4/2005 | Heruth et al. | |
| 2005/0079201 A1 | 4/2005 | Rathenow et al. | |
| 2005/0079356 A1 | 4/2005 | Rathenow et al. | |
| 2005/0087520 A1 | 4/2005 | Wang et al. | |
| 2005/0092615 A1 | 5/2005 | Birdsall et al. | |
| 2005/0096731 A1 | 5/2005 | Looi et al. | |
| 2005/0100577 A1 | 5/2005 | Parker et al. | |
| 2005/0100609 A1 | 5/2005 | Claude | |
| 2005/0102025 A1 | 5/2005 | Laroche et al. | |
| 2005/0106212 A1 | 5/2005 | Gertner et al. | |
| 2005/0107869 A1 | 5/2005 | Sirhan et al. | |
| 2005/0107870 A1 | 5/2005 | Wang et al. | |
| 2005/0110214 A1 | 5/2005 | Shank et al. | |
| 2005/0113798 A1 | 5/2005 | Slater et al. | |
| 2005/0113936 A1 | 5/2005 | Brustad et al. | |
| 2005/0118229 A1 | 6/2005 | Boiarski | |
| 2005/0119723 A1 | 6/2005 | Peacock | |
| 2005/0129727 A1 | 6/2005 | Weber et al. | |
| 2005/0131509 A1 | 6/2005 | Atanasoska et al. | |
| 2005/0131521 A1 | 6/2005 | Marton | |
| 2005/0131522 A1 | 6/2005 | Stinson et al. | |
| 2005/0131532 A1 | 6/2005 | Sirhan et al. | |
| 2005/0136090 A1 | 6/2005 | Falotico et al. | |
| 2005/0137677 A1 | 6/2005 | Rush | |
| 2005/0137679 A1 | 6/2005 | Changelian et al. | |
| 2005/0137684 A1 | 6/2005 | Changelian et al. | |
| 2005/0149102 A1 | 7/2005 | Radisch et al. | |
| 2005/0149170 A1 | 7/2005 | Tassel et al. | |
| 2005/0159804 A1 | 7/2005 | Lad et al. | |
| 2005/0159805 A1 | 7/2005 | Weber et al. | |
| 2005/0160600 A1 | 7/2005 | Bien et al. | |
| 2005/0163954 A1 | 7/2005 | Shaw | |
| 2005/0165467 A1 | 7/2005 | Hunter et al. | |
| 2005/0165468 A1 | 7/2005 | Marton | |
| 2005/0165476 A1 | 7/2005 | Furst et al. | |
| 2005/0171595 A1 | 8/2005 | Feldman et al. | |
| 2005/0171596 A1 * | 8/2005 | Furst et al. | 623/1.15 |
| 2005/0171611 A1 * | 8/2005 | Stoy et al. | 623/17.16 |
| 2005/0180919 A1 | 8/2005 | Tedeschi | |
| 2005/0182478 A1 | 8/2005 | Holman et al. | |
| 2005/0186250 A1 | 8/2005 | Gertner et al. | |
| 2005/0187608 A1 | 8/2005 | O'Hara | |
| 2005/0192657 A1 | 9/2005 | Colen et al. | |
| 2005/0192664 A1 | 9/2005 | Eisert | |
| 2005/0196424 A1 | 9/2005 | Chappa | |
| 2005/0196518 A1 | 9/2005 | Stenzel | |
| 2005/0197687 A1 | 9/2005 | Molaei et al. | |
| 2005/0197689 A1 | 9/2005 | Molaei | |

| | | |
|---|---|---|
| 2005/0203606 A1 | 9/2005 | Vancamp |
| 2005/0208098 A1 | 9/2005 | Castro et al. |
| 2005/0208100 A1 | 9/2005 | Weber et al. |
| 2005/0209681 A1 | 9/2005 | Curcio et al. |
| 2005/0211680 A1 | 9/2005 | Li et al. |
| 2005/0214951 A1 | 9/2005 | Nahm et al. |
| 2005/0216074 A1 | 9/2005 | Sahatjian et al. |
| 2005/0216075 A1 | 9/2005 | Wang et al. |
| 2005/0220853 A1 | 10/2005 | Dao et al. |
| 2005/0221072 A1 | 10/2005 | Dubrow et al. |
| 2005/0228477 A1* | 10/2005 | Grainger et al. ............ 623/1.11 |
| 2005/0228491 A1 | 10/2005 | Snyder et al. |
| 2005/0232968 A1 | 10/2005 | Palmaz et al. |
| 2005/0233965 A1 | 10/2005 | Schwartz et al. |
| 2005/0244459 A1 | 11/2005 | DeWitt et al. |
| 2005/0251245 A1 | 11/2005 | Sieradzki et al. |
| 2005/0251249 A1 | 11/2005 | Sahatjian et al. |
| 2005/0255707 A1 | 11/2005 | Hart et al. |
| 2005/0261760 A1 | 11/2005 | Weber |
| 2005/0266039 A1 | 12/2005 | Weber |
| 2005/0266040 A1 | 12/2005 | Gerberding |
| 2005/0267561 A1 | 12/2005 | Jones et al. |
| 2005/0271703 A1 | 12/2005 | Anderson et al. |
| 2005/0271706 A1 | 12/2005 | Anderson et al. |
| 2005/0276837 A1 | 12/2005 | Anderson et al. |
| 2005/0278016 A1 | 12/2005 | Welsh et al. |
| 2005/0278021 A1 | 12/2005 | Bates et al. |
| 2005/0281863 A1 | 12/2005 | Anderson et al. |
| 2005/0285073 A1 | 12/2005 | Singh et al. |
| 2005/0287188 A1 | 12/2005 | Anderson et al. |
| 2006/0013850 A1 | 1/2006 | Domb |
| 2006/0015175 A1 | 1/2006 | Palmaz et al. |
| 2006/0015361 A1 | 1/2006 | Sattler et al. |
| 2006/0020742 A1 | 1/2006 | Au et al. |
| 2006/0025848 A1 | 2/2006 | Weber et al. |
| 2006/0034884 A1 | 2/2006 | Stenzel |
| 2006/0035026 A1 | 2/2006 | Atanasoska et al. |
| 2006/0038027 A1 | 2/2006 | O'Connor et al. |
| 2006/0051397 A1 | 3/2006 | Maier et al. |
| 2006/0052744 A1 | 3/2006 | Weber |
| 2006/0052863 A1 | 3/2006 | Harder et al. |
| 2006/0052864 A1 | 3/2006 | Harder et al. |
| 2006/0062820 A1 | 3/2006 | Gertner et al. |
| 2006/0069427 A1 | 3/2006 | Savage et al. |
| 2006/0075044 A1 | 4/2006 | Fox et al. |
| 2006/0075092 A1 | 4/2006 | Kidokoro |
| 2006/0079863 A1 | 4/2006 | Burgmeier et al. |
| 2006/0085062 A1 | 4/2006 | Lee et al. |
| 2006/0085065 A1 | 4/2006 | Krause et al. |
| 2006/0088561 A1 | 4/2006 | Eini et al. |
| 2006/0088566 A1 | 4/2006 | Parsonage et al. |
| 2006/0088567 A1 | 4/2006 | Warner et al. |
| 2006/0088666 A1 | 4/2006 | Kobrin et al. |
| 2006/0093643 A1 | 5/2006 | Stenzel |
| 2006/0093646 A1 | 5/2006 | Cima et al. |
| 2006/0095123 A1 | 5/2006 | Flanagan |
| 2006/0100696 A1 | 5/2006 | Atanasoska et al. |
| 2006/0115512 A1 | 6/2006 | Peacock et al. |
| 2006/0121080 A1 | 6/2006 | Lye et al. |
| 2006/0122694 A1 | 6/2006 | Stinson et al. |
| 2006/0125144 A1 | 6/2006 | Weber et al. |
| 2006/0127442 A1 | 6/2006 | Helmus |
| 2006/0127443 A1 | 6/2006 | Helmus |
| 2006/0129215 A1 | 6/2006 | Helmus et al. |
| 2006/0129225 A1 | 6/2006 | Kopia et al. |
| 2006/0136048 A1 | 6/2006 | Pacetti et al. |
| 2006/0140867 A1 | 6/2006 | Helfer et al. |
| 2006/0141156 A1 | 6/2006 | Viel et al. |
| 2006/0142853 A1 | 6/2006 | Wang et al. |
| 2006/0149365 A1 | 7/2006 | Fifer et al. |
| 2006/0153729 A1 | 7/2006 | Stinson et al. |
| 2006/0155361 A1 | 7/2006 | Schomig et al. |
| 2006/0167543 A1 | 7/2006 | Bailey et al. |
| 2006/0171985 A1 | 8/2006 | Richard et al. |
| 2006/0171990 A1 | 8/2006 | Asgari |
| 2006/0178727 A1 | 8/2006 | Richter |
| 2006/0184235 A1 | 8/2006 | Rivron et al. |
| 2006/0193886 A1 | 8/2006 | Owens et al. |
| 2006/0193887 A1 | 8/2006 | Owens et al. |
| 2006/0193888 A1 | 8/2006 | Lye et al. |
| 2006/0193889 A1 | 8/2006 | Spradlin et al. |
| 2006/0193890 A1 | 8/2006 | Owens et al. |
| 2006/0199876 A1 | 9/2006 | Troczynski et al. |
| 2006/0200229 A1 | 9/2006 | Burgermeister et al. |
| 2006/0200231 A1 | 9/2006 | O'Brien et al. |
| 2006/0210595 A1 | 9/2006 | Singhvi et al. |
| 2006/0212109 A1 | 9/2006 | Sirhan et al. |
| 2006/0222679 A1 | 10/2006 | Shanley et al. |
| 2006/0222844 A1 | 10/2006 | Stinson |
| 2006/0224234 A1 | 10/2006 | Jayaraman |
| 2006/0229711 A1 | 10/2006 | Yan et al. |
| 2006/0229713 A1 | 10/2006 | Shanley et al. |
| 2006/0229715 A1 | 10/2006 | Istephanous et al. |
| 2006/0230476 A1 | 10/2006 | Atanasoska et al. |
| 2006/0233941 A1 | 10/2006 | Olson |
| 2006/0251701 A1 | 11/2006 | Lynn et al. |
| 2006/0263512 A1 | 11/2006 | Glocker |
| 2006/0263515 A1 | 11/2006 | Rieck et al. |
| 2006/0264138 A1 | 11/2006 | Sowinski et al. |
| 2006/0271169 A1 | 11/2006 | Lye et al. |
| 2006/0275554 A1 | 12/2006 | Zhao et al. |
| 2006/0276877 A1 | 12/2006 | Owens et al. |
| 2006/0276878 A1 | 12/2006 | Owens et al. |
| 2006/0276879 A1 | 12/2006 | Lye et al. |
| 2006/0276884 A1 | 12/2006 | Lye et al. |
| 2006/0276885 A1 | 12/2006 | Lye et al. |
| 2006/0276910 A1 | 12/2006 | Weber |
| 2006/0280770 A1 | 12/2006 | Hossainy et al. |
| 2006/0292388 A1 | 12/2006 | Palumbo et al. |
| 2007/0003589 A1 | 1/2007 | Astafieva et al. |
| 2007/0003817 A1 | 1/2007 | Umeda et al. |
| 2007/0032858 A1 | 2/2007 | Santos et al. |
| 2007/0032864 A1 | 2/2007 | Furst et al. |
| 2007/0036905 A1 | 2/2007 | Kramer |
| 2007/0038176 A1 | 2/2007 | Weber et al. |
| 2007/0038289 A1 | 2/2007 | Nishide et al. |
| 2007/0048452 A1 | 3/2007 | Feng et al. |
| 2007/0052497 A1 | 3/2007 | Tada |
| 2007/0055349 A1 | 3/2007 | Santos et al. |
| 2007/0055354 A1 | 3/2007 | Santos et al. |
| 2007/0059435 A1 | 3/2007 | Santos et al. |
| 2007/0065418 A1 | 3/2007 | Vallana et al. |
| 2007/0071789 A1 | 3/2007 | Pantelidis et al. |
| 2007/0072978 A1 | 3/2007 | Zoromski et al. |
| 2007/0073385 A1 | 3/2007 | Schaeffer et al. |
| 2007/0073390 A1* | 3/2007 | Lee ............... 623/1.46 |
| 2007/0106347 A1 | 5/2007 | Lin |
| 2007/0110888 A1 | 5/2007 | Radhakrishnan et al. |
| 2007/0112421 A1 | 5/2007 | O'Brien |
| 2007/0123973 A1 | 5/2007 | Roth et al. |
| 2007/0128245 A1 | 6/2007 | Rosenberg et al. |
| 2007/0129789 A1 | 6/2007 | Cottone et al. |
| 2007/0134288 A1 | 6/2007 | Parsonage et al. |
| 2007/0135908 A1 | 6/2007 | Zhao |
| 2007/0141106 A1* | 6/2007 | Kutryk et al. ............... 424/423 |
| 2007/0148251 A1 | 6/2007 | Hossainy et al. |
| 2007/0151093 A1 | 7/2007 | Curcio et al. |
| 2007/0154513 A1 | 7/2007 | Atanasoska et al. |
| 2007/0156231 A1 | 7/2007 | Weber |
| 2007/0173923 A1 | 7/2007 | Savage et al. |
| 2007/0181433 A1 | 8/2007 | Birdsall et al. |
| 2007/0190104 A1 | 8/2007 | Kamath et al. |
| 2007/0191923 A1 | 8/2007 | Weber et al. |
| 2007/0191928 A1 | 8/2007 | Rolando et al. |
| 2007/0191931 A1 | 8/2007 | Weber et al. |
| 2007/0191943 A1 | 8/2007 | Shrivastava et al. |
| 2007/0198081 A1* | 8/2007 | Castro et al. ............... 623/1.42 |
| 2007/0202466 A1 | 8/2007 | Schwarz et al. |
| 2007/0207186 A1 | 9/2007 | Scanlon et al. |
| 2007/0208412 A1 | 9/2007 | Elmaleh |
| 2007/0212547 A1 | 9/2007 | Fredrickson et al. |
| 2007/0213827 A1 | 9/2007 | Arramon |
| 2007/0219626 A1 | 9/2007 | Rolando et al. |
| 2007/0219642 A1 | 9/2007 | Richter |
| 2007/0224116 A1 | 9/2007 | Chandrasekaran et al. |
| 2007/0224224 A1 | 9/2007 | Cordeira Da Silva et al. |
| 2007/0224235 A1 | 9/2007 | Tenney et al. |

| | | |
|---|---|---|
| 2007/0224244 A1 | 9/2007 | Weber et al. |
| 2007/0244569 A1 | 10/2007 | Weber et al. |
| 2007/0254091 A1 | 11/2007 | Fredrickson et al. |
| 2007/0255392 A1 | 11/2007 | Johnson |
| 2007/0264303 A1 | 11/2007 | Atanasoska et al. |
| 2007/0269480 A1 | 11/2007 | Richard et al. |
| 2007/0299509 A1 | 12/2007 | Ding |
| 2008/0003251 A1 | 1/2008 | Zhou |
| 2008/0004691 A1 | 1/2008 | Weber et al. |
| 2008/0008654 A1 | 1/2008 | Clarke et al. |
| 2008/0038146 A1 | 2/2008 | Wachter et al. |
| 2008/0050413 A1 | 2/2008 | Horvers et al. |
| 2008/0050415 A1 | 2/2008 | Atanasoska et al. |
| 2008/0051881 A1 | 2/2008 | Feng et al. |
| 2008/0057103 A1 | 3/2008 | Roorda |
| 2008/0058921 A1 | 3/2008 | Lindquist |
| 2008/0069854 A1 | 3/2008 | Xiao et al. |
| 2008/0071348 A1 | 3/2008 | Boismier et al. |
| 2008/0071349 A1 | 3/2008 | Atanasoska et al. |
| 2008/0071350 A1 | 3/2008 | Stinson |
| 2008/0071351 A1 | 3/2008 | Flanagan et al. |
| 2008/0071352 A1 | 3/2008 | Weber et al. |
| 2008/0071353 A1 | 3/2008 | Weber et al. |
| 2008/0071355 A1 | 3/2008 | Weber et al. |
| 2008/0071358 A1 | 3/2008 | Weber et al. |
| 2008/0086198 A1 | 4/2008 | Owens et al. |
| 2008/0086199 A1 | 4/2008 | Dave et al. |
| 2008/0086201 A1 | 4/2008 | Weber et al. |
| 2008/0097577 A1 | 4/2008 | Atanasoska et al. |
| 2008/0107890 A1 | 5/2008 | Bureau et al. |
| 2008/0124373 A1 | 5/2008 | Xiao et al. |
| 2008/0140186 A1 | 6/2008 | Grignani et al. |
| 2008/0145400 A1 | 6/2008 | Weber et al. |
| 2008/0147177 A1 | 6/2008 | Scheuermann et al. |
| 2008/0152929 A1 | 6/2008 | Zhao |
| 2008/0160259 A1 | 7/2008 | Nielson et al. |
| 2008/0171929 A1 | 7/2008 | Katims |
| 2008/0183278 A1 | 7/2008 | Atanasoska et al. |
| 2008/0188836 A1 | 8/2008 | Weber et al. |
| 2008/0241218 A1 | 10/2008 | McMorrow et al. |
| 2008/0243231 A1 | 10/2008 | Flanagan et al. |
| 2008/0243240 A1 | 10/2008 | Doty et al. |
| 2008/0249600 A1 | 10/2008 | Atanasoska et al. |
| 2008/0249615 A1 | 10/2008 | Weber |
| 2008/0255508 A1 | 10/2008 | Wang |
| 2008/0255657 A1 | 10/2008 | Gregorich et al. |
| 2008/0262607 A1 | 10/2008 | Fricke |
| 2008/0275543 A1 | 11/2008 | Lenz et al. |
| 2008/0288048 A1 | 11/2008 | Rolando et al. |
| 2008/0290467 A1 | 11/2008 | Shue et al. |
| 2008/0294236 A1 | 11/2008 | Anand et al. |
| 2008/0294246 A1 | 11/2008 | Scheuermann et al. |
| 2008/0306584 A1 | 12/2008 | Kramer-Brown |
| 2009/0012603 A1* | 1/2009 | Xu et al. ..................... 623/1.42 |
| 2009/0018639 A1 | 1/2009 | Kuehling |
| 2009/0018642 A1 | 1/2009 | Benco |
| 2009/0018644 A1 | 1/2009 | Weber et al. |
| 2009/0018647 A1 | 1/2009 | Benco et al. |
| 2009/0028785 A1 | 1/2009 | Clarke |
| 2009/0030504 A1 | 1/2009 | Weber et al. |
| 2009/0076588 A1 | 3/2009 | Weber |
| 2009/0076595 A1 | 3/2009 | Lindquist et al. |
| 2009/0081450 A1 | 3/2009 | Ascher et al. |
| 2009/0112310 A1 | 4/2009 | Zhang |
| 2009/0118809 A1 | 5/2009 | Scheuermann et al. |
| 2009/0118812 A1 | 5/2009 | Kokate et al. |
| 2009/0118813 A1 | 5/2009 | Scheuermann et al. |
| 2009/0118814 A1 | 5/2009 | Schoenle et al. |
| 2009/0118815 A1 | 5/2009 | Arcand et al. |
| 2009/0118818 A1 | 5/2009 | Foss et al. |
| 2009/0118820 A1 | 5/2009 | Gregorich et al. |
| 2009/0118821 A1 | 5/2009 | Scheuermann et al. |
| 2009/0118822 A1 | 5/2009 | Holman et al. |
| 2009/0118823 A1 | 5/2009 | Atanasoska et al. |
| 2009/0123517 A1 | 5/2009 | Flanagan et al. |
| 2009/0123521 A1 | 5/2009 | Weber et al. |
| 2009/0138077 A1 | 5/2009 | Weber et al. |
| 2009/0149942 A1 | 6/2009 | Edelman et al. |
| 2009/0157165 A1 | 6/2009 | Miller et al. |
| 2009/0157166 A1 | 6/2009 | Singhal et al. |
| 2009/0157172 A1 | 6/2009 | Kokate et al. |
| 2009/0177273 A1* | 7/2009 | Piveteau et al. ............... 623/1.46 |
| 2009/0186068 A1 | 7/2009 | Miller et al. |
| 2009/0192593 A1 | 7/2009 | Meyer et al. |
| 2009/0202610 A1 | 8/2009 | Wilson |
| 2009/0204196 A1* | 8/2009 | Weber ........................... 623/1.2 |
| 2009/0208428 A1 | 8/2009 | Hill et al. |
| 2009/0220612 A1 | 9/2009 | Perera |
| 2009/0259300 A1 | 10/2009 | Dorogy, Jr. et al. |
| 2009/0264975 A1 | 10/2009 | Flanagan et al. |
| 2009/0281613 A1 | 11/2009 | Atanasoska et al. |
| 2009/0287301 A1 | 11/2009 | Weber |
| 2009/0306765 A1 | 12/2009 | Weber |
| 2009/0317766 A1 | 12/2009 | Heidenau et al. |
| 2009/0319032 A1 | 12/2009 | Weber et al. |
| 2010/0003904 A1 | 1/2010 | Duescher |
| 2010/0008970 A1 | 1/2010 | O'Brien et al. |
| 2010/0028403 A1 | 2/2010 | Scheuermann et al. |
| 2010/0030326 A1 | 2/2010 | Radhakrishnan et al. |
| 2010/0042206 A1 | 2/2010 | Yadav et al. |
| 2010/0042207 A1* | 2/2010 | Gellman et al. ............... 623/1.44 |
| 2010/0057197 A1 | 3/2010 | Weber et al. |
| 2010/0070013 A1 | 3/2010 | Park |
| 2010/0070022 A1 | 3/2010 | Kuehling |
| 2010/0070026 A1 | 3/2010 | Ito et al. |
| 2010/0130346 A1 | 5/2010 | Laine et al. |
| 2010/0131050 A1 | 5/2010 | Zhao |
| 2010/0233226 A1 | 9/2010 | Ferain et al. |
| 2010/0233227 A1* | 9/2010 | Weber ........................... 424/422 |
| 2011/0034752 A1 | 2/2011 | Kessler et al. |
| 2011/0264190 A1* | 10/2011 | McClain et al. ............... 623/1.11 |
| 2011/0313502 A1* | 12/2011 | Granada et al. ............... 623/1.2 |
| 2012/0010583 A1* | 1/2012 | Janusson et al. ............... 604/369 |
| 2013/0190857 A1* | 7/2013 | Mitra et al. ................... 623/1.23 |
| 2013/0261526 A1* | 10/2013 | Cleary et al. ................... 602/43 |

FOREIGN PATENT DOCUMENTS

| | | |
|---|---|---|
| AU | 4825696 | 10/1996 |
| AU | 5588896 | 12/1996 |
| AU | 5266698 | 6/1998 |
| AU | 6663298 | 9/1998 |
| AU | 716005 | 2/2000 |
| AU | 5686499 | 3/2000 |
| AU | 2587100 | 5/2000 |
| AU | 2153600 | 6/2000 |
| AU | 1616201 | 5/2001 |
| AU | 737252 | 8/2001 |
| AU | 2317701 | 8/2001 |
| AU | 5215401 | 9/2001 |
| AU | 5890401 | 12/2001 |
| AU | 3597401 | 6/2002 |
| AU | 2002353068 | 3/2003 |
| AU | 2002365875 | 6/2003 |
| AU | 2003220153 | 9/2003 |
| AU | 2003250913 | 1/2004 |
| AU | 770395 | 2/2004 |
| AU | 2003249017 | 2/2004 |
| AU | 2003256499 | 2/2004 |
| AU | 771367 | 3/2004 |
| AU | 2003271633 | 4/2004 |
| AU | 2003272710 | 4/2004 |
| AU | 2003285195 | 6/2004 |
| AU | 2003287633 | 6/2004 |
| AU | 2003290675 | 6/2004 |
| AU | 2003290676 | 6/2004 |
| AU | 2003291470 | 6/2004 |
| AU | 2003295419 | 6/2004 |
| AU | 2003295535 | 6/2004 |
| AU | 2003295763 | 6/2004 |
| AU | 2004202073 | 6/2004 |
| AU | 2003300323 | 7/2004 |
| AU | 2004213021 | 9/2004 |
| AU | 2003293557 | 1/2005 |
| AU | 780539 | 3/2005 |
| BR | 8701135 | 1/1988 |
| BR | 0207321 | 2/2004 |

(56) References Cited

FOREIGN PATENT DOCUMENTS

| | | |
|---|---|---|
| BR | 0016957 | 6/2004 |
| BR | 0316065 | 9/2005 |
| BR | 0316102 | 9/2005 |
| CA | 1283505 | 4/1991 |
| CA | 2172187 | 10/1996 |
| CA | 2178541 | 12/1996 |
| CA | 2234787 | 10/1998 |
| CA | 2235031 | 10/1998 |
| CA | 2238837 | 2/1999 |
| CA | 2340652 | 3/2000 |
| CA | 2392006 | 5/2001 |
| CA | 2337565 | 8/2001 |
| CA | 2409862 | 11/2001 |
| CA | 2353197 | 1/2002 |
| CA | 2429356 | 8/2002 |
| CA | 2435306 | 8/2002 |
| CA | 2436241 | 8/2002 |
| CA | 2438095 | 8/2002 |
| CA | 2460334 | 3/2003 |
| CA | 2425665 | 4/2003 |
| CA | 2465704 | 4/2003 |
| CA | 2464906 | 5/2003 |
| CA | 2468677 | 6/2003 |
| CA | 2469744 | 6/2003 |
| CA | 2484383 | 1/2004 |
| CA | 2497602 | 4/2004 |
| CA | 2499976 | 4/2004 |
| CA | 2503625 | 5/2004 |
| CA | 2504524 | 5/2004 |
| CA | 2505576 | 5/2004 |
| CA | 2513721 | 5/2004 |
| CA | 2505080 | 6/2004 |
| CA | 2506622 | 6/2004 |
| CA | 2455670 | 7/2004 |
| CA | 2508247 | 7/2004 |
| CA | 2458172 | 8/2004 |
| CA | 2467797 | 11/2004 |
| CA | 2258898 | 1/2005 |
| CA | 2308177 | 1/2005 |
| CA | 2475968 | 1/2005 |
| CA | 2489668 | 6/2005 |
| CA | 2490170 | 6/2005 |
| CA | 2474367 | 1/2006 |
| CA | 2374090 | 5/2007 |
| CA | 2282748 | 11/2007 |
| CA | 2336650 | 1/2008 |
| CA | 2304325 | 5/2008 |
| CN | 1430491 | 7/2003 |
| CN | 1547490 | 11/2004 |
| CN | 1575154 | 2/2005 |
| CN | 1585627 | 2/2005 |
| CN | 1669537 | 9/2005 |
| DE | 3516411 | 11/1986 |
| DE | 3608158 | 9/1987 |
| DE | 19916086 | 10/1999 |
| DE | 19855421 | 5/2000 |
| DE | 19916315 | 9/2000 |
| DE | 9422438 | 4/2002 |
| DE | 1096902 | 5/2002 |
| DE | 10064596 | 6/2002 |
| DE | 10107339 | 9/2002 |
| DE | 69712063 | 10/2002 |
| DE | 10127011 | 12/2002 |
| DE | 10150995 | 4/2003 |
| DE | 69807634 | 5/2003 |
| DE | 69431457 | 6/2003 |
| DE | 10200387 | 8/2003 |
| DE | 69719161 | 10/2003 |
| DE | 02704283 | 4/2004 |
| DE | 60106962 | 4/2005 |
| DE | 60018318 | 12/2005 |
| DE | 69732439 | 1/2006 |
| DE | 69828798 | 1/2006 |
| DE | 102004044738 | 3/2006 |
| DE | 69830605 | 5/2006 |
| DE | 102005010100 | 9/2006 |
| DE | 602005001867 | 5/2008 |
| DE | 69829015 | 3/2009 |
| DK | 127987 | 9/1987 |
| DK | 914092 | 8/2002 |
| EP | 0222853 | 5/1987 |
| EP | 0129147 | 1/1990 |
| EP | 0734721 | 10/1996 |
| EP | 0650604 | 9/1998 |
| EP | 0865762 | 9/1998 |
| EP | 0875217 | 11/1998 |
| EP | 0633840 | 11/1999 |
| EP | 0953320 | 11/1999 |
| EP | 0971644 | 1/2000 |
| EP | 0982041 | 3/2000 |
| EP | 1105169 | 6/2001 |
| EP | 1124594 | 8/2001 |
| EP | 1127582 | 8/2001 |
| EP | 1131127 | 9/2001 |
| EP | 1132058 | 9/2001 |
| EP | 1150738 | 11/2001 |
| EP | 1172074 | 1/2002 |
| EP | 1181943 | 2/2002 |
| EP | 0914092 | 4/2002 |
| EP | 1216665 | 6/2002 |
| EP | 0747069 | 9/2002 |
| EP | 0920342 | 9/2002 |
| EP | 1242130 | 9/2002 |
| EP | 0623354 | 10/2002 |
| EP | 0806211 | 10/2002 |
| EP | 1275352 | 1/2003 |
| EP | 0850604 | 2/2003 |
| EP | 1280512 | 2/2003 |
| EP | 1280568 | 2/2003 |
| EP | 1280569 | 2/2003 |
| EP | 1294309 | 3/2003 |
| EP | 0824900 | 4/2003 |
| EP | 1308179 | 5/2003 |
| EP | 1310242 | 5/2003 |
| EP | 1314405 | 5/2003 |
| EP | 1316323 | 6/2003 |
| EP | 1339448 | 9/2003 |
| EP | 1347791 | 10/2003 |
| EP | 1347792 | 10/2003 |
| EP | 1348402 | 10/2003 |
| EP | 1348405 | 10/2003 |
| EP | 1359864 | 11/2003 |
| EP | 1365710 | 12/2003 |
| EP | 1379290 | 1/2004 |
| EP | 0902666 | 2/2004 |
| EP | 1460972 | 2/2004 |
| EP | 0815806 | 3/2004 |
| EP | 1400219 | 3/2004 |
| EP | 0950386 | 4/2004 |
| EP | 1461165 | 4/2004 |
| EP | 1416884 | 5/2004 |
| EP | 1424957 | 6/2004 |
| EP | 1429816 | 6/2004 |
| EP | 1448116 | 8/2004 |
| EP | 1448118 | 8/2004 |
| EP | 1449545 | 8/2004 |
| EP | 1449546 | 8/2004 |
| EP | 1254674 | 9/2004 |
| EP | 1453557 | 9/2004 |
| EP | 1457214 | 9/2004 |
| EP | 0975340 | 10/2004 |
| EP | 1319416 | 11/2004 |
| EP | 1476882 | 11/2004 |
| EP | 1479402 | 11/2004 |
| EP | 1482867 | 12/2004 |
| EP | 1011529 | 1/2005 |
| EP | 0875218 | 2/2005 |
| EP | 1181903 | 2/2005 |
| EP | 1504775 | 2/2005 |
| EP | 1042997 | 3/2005 |
| EP | 1754684 | 3/2005 |
| EP | 1520594 | 4/2005 |
| EP | 1521603 | 4/2005 |
| EP | 1028672 | 6/2005 |

(56) References Cited

FOREIGN PATENT DOCUMENTS

| | | |
|---|---|---|
| EP | 1539041 | 6/2005 |
| EP | 1543798 | 6/2005 |
| EP | 1550472 | 6/2005 |
| EP | 1328213 | 7/2005 |
| EP | 1551569 | 7/2005 |
| EP | 1554992 | 7/2005 |
| EP | 1560613 | 8/2005 |
| EP | 1562519 | 8/2005 |
| EP | 1562654 | 8/2005 |
| EP | 1570808 | 9/2005 |
| EP | 1575631 | 9/2005 |
| EP | 1575638 | 9/2005 |
| EP | 1575642 | 9/2005 |
| EP | 0900059 | 10/2005 |
| EP | 1581147 | 10/2005 |
| EP | 1586286 | 10/2005 |
| EP | 1254673 | 11/2005 |
| EP | 1261297 | 11/2005 |
| EP | 0927006 | 1/2006 |
| EP | 1621603 | 2/2006 |
| EP | 1218665 | 5/2006 |
| EP | 1222941 | 5/2006 |
| EP | 1359867 | 5/2006 |
| EP | 1656961 | 5/2006 |
| EP | 1277449 | 6/2006 |
| EP | 0836839 | 7/2006 |
| EP | 1684817 | 8/2006 |
| EP | 1687042 | 8/2006 |
| EP | 0907339 | 11/2006 |
| EP | 1359865 | 11/2006 |
| EP | 1214108 | 1/2007 |
| EP | 1416885 | 1/2007 |
| EP | 1441667 | 1/2007 |
| EP | 1192957 | 2/2007 |
| EP | 1236447 | 2/2007 |
| EP | 1764116 | 3/2007 |
| EP | 1185215 | 4/2007 |
| EP | 1442757 | 4/2007 |
| EP | 1786363 | 5/2007 |
| EP | 1787602 | 5/2007 |
| EP | 1788973 | 5/2007 |
| EP | 1796754 | 6/2007 |
| EP | 1330273 | 7/2007 |
| EP | 0900060 | 8/2007 |
| EP | 1355588 | 8/2007 |
| EP | 1355589 | 8/2007 |
| EP | 1561436 | 8/2007 |
| EP | 1863408 | 12/2007 |
| EP | 1071490 | 1/2008 |
| EP | 1096902 | 1/2008 |
| EP | 0895762 | 2/2008 |
| EP | 0916317 | 2/2008 |
| EP | 1891988 | 2/2008 |
| EP | 1402849 | 4/2008 |
| EP | 1466634 | 7/2008 |
| EP | 1572032 | 7/2008 |
| EP | 1527754 | 8/2008 |
| EP | 1968662 | 9/2008 |
| EP | 1980223 | 10/2008 |
| EP | 1988943 | 11/2008 |
| EP | 1490125 | 1/2009 |
| EP | 1829626 | 2/2009 |
| EP | 1229901 | 3/2009 |
| EP | 1128785 | 4/2009 |
| EP | 2051750 | 4/2009 |
| EP | 1427353 | 5/2009 |
| ES | 2169012 | 7/2002 |
| FR | 2867059 | 9/2005 |
| GB | 2397233 | 7/2004 |
| JP | 7002180 | 1/1995 |
| JP | 3673973 | 2/1996 |
| JP | 3249383 | 10/1996 |
| JP | 3614652 | 11/1998 |
| JP | 10295824 | 11/1998 |
| JP | 11188109 | 7/1999 |
| JP | 2000312721 | 11/2000 |
| JP | 2001098308 | 4/2001 |
| JP | 2001522640 | 11/2001 |
| JP | 2002065862 | 3/2002 |
| JP | 2002519139 | 7/2002 |
| JP | 2002523147 | 7/2002 |
| JP | 2002-308683 | 10/2002 |
| JP | 2003024449 | 1/2003 |
| JP | 2003-512098 | 4/2003 |
| JP | 2003521274 | 7/2003 |
| JP | 2003290361 | 10/2003 |
| JP | 2003-310744 | 11/2003 |
| JP | 2003533333 | 11/2003 |
| JP | 2004500925 | 1/2004 |
| JP | 2004188314 | 7/2004 |
| JP | 2004522559 | 7/2004 |
| JP | 2004223264 | 8/2004 |
| JP | 2004267750 | 9/2004 |
| JP | 2004275748 | 10/2004 |
| JP | 2004305753 | 11/2004 |
| JP | 2005501654 | 1/2005 |
| JP | 2005502426 | 1/2005 |
| JP | 2005040584 | 2/2005 |
| JP | 2005503184 | 2/2005 |
| JP | 2005503240 | 2/2005 |
| JP | 2005507285 | 3/2005 |
| JP | 2005511139 | 4/2005 |
| JP | 2005511242 | 4/2005 |
| JP | 2005131364 | 5/2005 |
| JP | 2005152526 | 6/2005 |
| JP | 2005152527 | 6/2005 |
| JP | 2005199054 | 7/2005 |
| JP | 2005199058 | 7/2005 |
| JP | 2008-503320 | 2/2008 |
| JP | 2008516726 | 5/2008 |
| KR | 2002/0066996 | 8/2002 |
| KR | 2004/0066409 | 7/2004 |
| KR | 2005/0117361 | 12/2005 |
| NZ | 331388 | 1/2000 |
| SU | 393044 | 12/1973 |
| WO | WO86/06617 | 11/1986 |
| WO | WO93/06792 | 4/1993 |
| WO | WO93/07934 | 4/1993 |
| WO | WO93/16656 | 9/1993 |
| WO | WO94/16646 | 8/1994 |
| WO | WO95/03083 | 2/1995 |
| WO | WO96/04952 | 2/1996 |
| WO | WO96/09086 | 3/1996 |
| WO | WO96/32907 | 10/1996 |
| WO | WO97/41916 | 11/1997 |
| WO | WO98/17331 | 4/1998 |
| WO | WO98/18408 | 5/1998 |
| WO | WO98/23228 | 6/1998 |
| WO | WO98/36784 | 8/1998 |
| WO | WO98/38946 | 9/1998 |
| WO | WO98/38947 | 9/1998 |
| WO | WO98/40033 | 9/1998 |
| WO | WO98/57680 | 12/1998 |
| WO | WO99/16386 | 4/1999 |
| WO | WO99/23977 | 5/1999 |
| WO | WO99/42631 | 8/1999 |
| WO | WO99/49928 | 10/1999 |
| WO | WO99/52471 | 10/1999 |
| WO | WO99/62432 | 12/1999 |
| WO | WO00/01322 | 1/2000 |
| WO | WO00/10622 | 3/2000 |
| WO | WO00/25841 | 5/2000 |
| WO | WO00/27303 | 5/2000 |
| WO | WO00/30710 | 6/2000 |
| WO | WO00/48660 | 8/2000 |
| WO | WO00/64506 | 11/2000 |
| WO | WO01/35928 | 5/2001 |
| WO | WO01/41827 | 6/2001 |
| WO | WO01/45862 | 6/2001 |
| WO | WO01/45763 | 7/2001 |
| WO | WO01/66036 | 9/2001 |
| WO | WO01/80920 | 11/2001 |
| WO | WO01/87263 | 11/2001 |
| WO | WO01/87342 | 11/2001 |

(56) References Cited

FOREIGN PATENT DOCUMENTS

| | | |
|---|---|---|
| WO | WO01/87374 | 11/2001 |
| WO | WO01/89417 | 11/2001 |
| WO | WO01/89420 | 11/2001 |
| WO | WO02/26162 | 4/2002 |
| WO | WO02/30487 | 4/2002 |
| WO | WO02/38827 | 5/2002 |
| WO | WO02/42521 | 5/2002 |
| WO | WO02/43796 | 6/2002 |
| WO | WO02/47581 | 6/2002 |
| WO | WO02/058753 | 8/2002 |
| WO | WO02/060349 | 8/2002 |
| WO | WO02/060350 | 8/2002 |
| WO | WO02/060506 | 8/2002 |
| WO | WO02/064019 | 8/2002 |
| WO | WO02/065947 | 8/2002 |
| WO | WO02/069848 | 9/2002 |
| WO | WO02/074431 | 9/2002 |
| WO | WO02/076525 | 10/2002 |
| WO | WO02/078668 | 10/2002 |
| WO | WO02/083039 | 10/2002 |
| WO | WO02/085253 | 10/2002 |
| WO | WO02/085424 | 10/2002 |
| WO | WO02/085532 | 10/2002 |
| WO | WO02/096389 | 12/2002 |
| WO | WO03/009779 | 2/2003 |
| WO | WO03/022178 | 3/2003 |
| WO | WO03/024357 | 3/2003 |
| WO | WO03/026713 | 4/2003 |
| WO | WO03/035131 | 5/2003 |
| WO | WO03/037220 | 5/2003 |
| WO | WO03/037221 | 5/2003 |
| WO | WO03/037223 | 5/2003 |
| WO | WO03/037398 | 5/2003 |
| WO | WO03/039407 | 5/2003 |
| WO | WO03/045582 | 6/2003 |
| WO | WO03/047463 | 6/2003 |
| WO | WO03/051233 | 6/2003 |
| WO | WO03/055414 | 7/2003 |
| WO | WO03/061755 | 7/2003 |
| WO | WO03/072287 | 9/2003 |
| WO | WO03/077802 | 9/2003 |
| WO | WO03/083181 | 10/2003 |
| WO | WO03/094774 | 11/2003 |
| WO | WO2004/004602 | 1/2004 |
| WO | WO2004/004603 | 1/2004 |
| WO | WO2004/006491 | 1/2004 |
| WO | WO2004/006807 | 1/2004 |
| WO | WO2004/006976 | 1/2004 |
| WO | WO2004/006983 | 1/2004 |
| WO | WO2004/010900 | 2/2004 |
| WO | WO2004/014554 | 2/2004 |
| WO | WO2004/026177 | 4/2004 |
| WO | WO2004/028347 | 4/2004 |
| WO | WO2004/028587 | 4/2004 |
| WO | WO2004/043292 | 5/2004 |
| WO | WO2004/043298 | 5/2004 |
| WO | WO2004/043300 | 5/2004 |
| WO | WO2004/043509 | 5/2004 |
| WO | WO2004/043511 | 5/2004 |
| WO | WO2004/045464 | 6/2004 |
| WO | WO2004/045668 | 6/2004 |
| WO | WO2004/058100 | 7/2004 |
| WO | WO2004/060428 | 7/2004 |
| WO | WO2004/064911 | 8/2004 |
| WO | WO2004/071548 | 8/2004 |
| WO | WO2004/072104 | 8/2004 |
| WO | WO2004/073768 | 9/2004 |
| WO | WO2004/080579 | 9/2004 |
| WO | WO2004/087251 | 10/2004 |
| WO | WO2004/096176 | 11/2004 |
| WO | WO2004/100827 | 11/2004 |
| WO | WO2004/101017 | 11/2004 |
| WO | WO2004/105639 | 12/2004 |
| WO | WO2004/108021 | 12/2004 |
| WO | WO2004/108186 | 12/2004 |
| WO | WO2004/108346 | 12/2004 |
| WO | WO2004/110302 | 12/2004 |
| WO | WO2005/004754 | 1/2005 |
| WO | WO2005/006325 | 1/2005 |
| WO | WO2005/011529 | 2/2005 |
| WO | WO2005/014892 | 2/2005 |
| WO | WO2005/015596 | 2/2005 |
| WO | WO2005/027794 | 3/2005 |
| WO | WO2005/032456 | 4/2005 |
| WO | WO2005/034806 | 4/2005 |
| WO | WO2005/042049 | 5/2005 |
| WO | WO2005/044361 | 5/2005 |
| WO | WO2005/049520 | 6/2005 |
| WO | WO2005/051450 | 6/2005 |
| WO | WO2005/053766 | 6/2005 |
| WO | WO2005/063318 | 7/2005 |
| WO | WO2005/072437 | 8/2005 |
| WO | WO2005/082277 | 9/2005 |
| WO | WO2005/082283 | 9/2005 |
| WO | WO2005/086733 | 9/2005 |
| WO | WO2005/089825 | 9/2005 |
| WO | WO2005/091834 | 10/2005 |
| WO | WO2005/099621 | 10/2005 |
| WO | WO2005/099626 | 10/2005 |
| WO | WO2005/110285 | 11/2005 |
| WO | WO2005/115276 | 12/2005 |
| WO | WO2005/115496 | 12/2005 |
| WO | WO2005/117752 | 12/2005 |
| WO | WO2006/014969 | 2/2006 |
| WO | WO2006/015161 | 2/2006 |
| WO | WO2006/020742 | 2/2006 |
| WO | WO2006/029364 | 3/2006 |
| WO | WO2006/029708 | 3/2006 |
| WO | WO2006/036801 | 4/2006 |
| WO | WO2006/055237 | 5/2006 |
| WO | WO2006/061598 | 6/2006 |
| WO | WO2006/063157 | 6/2006 |
| WO | WO2006/063158 | 6/2006 |
| WO | WO2006/074549 | 7/2006 |
| WO | WO2006/083418 | 8/2006 |
| WO | WO2006/104644 | 10/2006 |
| WO | WO2006/104976 | 10/2006 |
| WO | WO2006/105256 | 10/2006 |
| WO | WO2006/107677 | 10/2006 |
| WO | WO2006/116752 | 11/2006 |
| WO | WO2006/124365 | 11/2006 |
| WO | WO2007/016961 | 2/2007 |
| WO | WO2007/034167 | 3/2007 |
| WO | WO2007/070666 | 6/2007 |
| WO | WO2007/095167 | 8/2007 |
| WO | WO2007/124137 | 11/2007 |
| WO | WO2007/126768 | 11/2007 |
| WO | WO2007/130786 | 11/2007 |
| WO | WO2007/133520 | 11/2007 |
| WO | WO2007/143433 | 12/2007 |
| WO | WO2007/145961 | 12/2007 |
| WO | WO2007/147246 | 12/2007 |
| WO | WO2008/002586 | 1/2008 |
| WO | WO2008/002778 | 1/2008 |
| WO | WO2008/024149 | 2/2008 |
| WO | WO2008/024477 | 2/2008 |
| WO | WO2008/024669 | 2/2008 |
| WO | WO2008/033711 | 3/2008 |
| WO | WO2008/034048 | 3/2008 |
| WO | WO2008/036549 | 3/2008 |
| WO | WO2008/036554 | 3/2008 |
| WO | WO2008/039319 | 4/2008 |
| WO | WO2008/045184 | 4/2008 |
| WO | WO2008/057991 | 5/2008 |
| WO | WO2008/061017 | 5/2008 |
| WO | WO2008/063539 | 5/2008 |
| WO | WO2008/082698 | 7/2008 |
| WO | WO2008/106223 | 9/2008 |
| WO | WO2008/108987 | 9/2008 |
| WO | WO2008/124513 | 10/2008 |
| WO | WO2008/124519 | 10/2008 |
| WO | WO2008/134493 | 11/2008 |
| WO | WO2008/140482 | 11/2008 |
| WO | WO2008/147848 | 12/2008 |

(56) References Cited

FOREIGN PATENT DOCUMENTS

| | | |
|---|---|---|
| WO | WO2008/147853 | 12/2008 |
| WO | WO2009/009627 | 1/2009 |
| WO | WO2009/009628 | 1/2009 |
| WO | WO2009/012353 | 1/2009 |
| WO | WO2009/014692 | 1/2009 |
| WO | WO2009/014696 | 1/2009 |
| WO | WO2009/018035 | 2/2009 |
| WO | WO2009/020520 | 2/2009 |
| WO | WO2009/050168 | 4/2009 |
| WO | WO2009/059081 | 5/2009 |
| WO | WO2009/059085 | 5/2009 |
| WO | WO2009/059086 | 5/2009 |
| WO | WO2009/059098 | 5/2009 |
| WO | WO2009/059129 | 5/2009 |
| WO | WO2009/059141 | 5/2009 |
| WO | WO2009/059146 | 5/2009 |
| WO | WO2009/059165 | 5/2009 |
| WO | WO2009/059166 | 5/2009 |
| WO | WO2009/059180 | 5/2009 |
| WO | WO2009/059196 | 5/2009 |
| WO | WO2009/089382 | 7/2009 |
| WO | WO2009/091384 | 7/2009 |
| WO | WO2009/094270 | 7/2009 |
| WO | WO2009/126766 | 10/2009 |
| WO | WO2009/135008 | 11/2009 |
| WO | WO2009/137786 | 11/2009 |
| WO | WO2009/148821 | 12/2009 |
| WO | WO2010/030873 | 3/2010 |
| ZA | 9710342 | 6/1998 |

OTHER PUBLICATIONS

U.S. Appl. No. 11/694,436, filed Mar. 30, 2007, Atanasoska et al.
"Cyclic voltammetry"—from Wikipedia, (http://en.wikipedia.org/wiki/Cyclic_voltammetry), pp. 1-3, (downloaded [2007]).
"Electrophoretic deposition"—from Wikipedia, (http://en.wikipedia.org/wiki/electrophoretic_deposition), pp. 1-8, (downloaded [2007]).
"Impressive Progress in Interventional Cardiology—From 1st Balloon Inflation to First Bioabsorbable Stent," Medical News Today, pp. 1-2, May 15, 2006, (http://www.medicalnewstoday.com/articles/43313.php).
"Inorganic Polymers", Polymer Science Learning Center, Department of Polymer Science, University of Southern Mississippi, 5 pages, [first accessed Aug. 17, 2011].
"Jomed Starts Clinical Studies on Tacrolimus-Eluting Coronary Stents," Jomed Press Release, 2 pages, Jan. 14, 2002.
"Nano PLD," PVD Products, Inc. Wilmington, MA, pp. 1-2, (2003).
"Paclitaxel"—from Wikipedia, (http://en.wikipedia.org/wiki/Paclitaxel), 12 pages, (downloaded Sep. 14, 2011).
"Sputtering," Wikipedia.com, (http://en.wikipedia.org/wiki/Sputtering), pp. 1-5, (downloaded [2009]).
"Ultraviolet-Ozone Surface Treatment," Three Bond Technical News #17, pp. 1-10, Issued Mar. 20, 1987, (http://www.threebond.co.jp/en/technical/technicalnews/pdf/tech17.pdf).
Abbott et al., "Voltammetric and impedance studies of the electropolishing of type 316 stainless steel in a choline chloride based ionic liquid," Electrochimica Acta, vol. 51, pp. 4420-4425, (2006).
Abstract: "Edelstahlfreier stent aus niobium mit iridiumoxyd (IrOx)-beschichtung: Erste Ergebnisse der LUSTY-studie", (Stainless steel-free Stent out of niobium with iridiumoxyd (IrOx)-coating: Initial results of the LUSTY-study), Annual Meeting of the German Society for Cardiology, Apr. 24-26, 2003.
Adanur et al., "Nanocomposite Fiber Based Web and Membrane Formation and Characterization," Journal of Industrial Textiles, vol. 36, No. 4, pp. 311-327, Apr. 2007.
Advincula et al., "Surface modification of surface sol-gel derived titanium oxide films by self-assembled monolayers (SAMs) and non-specific protein adsorption studies," Colloids and Surfaces B: Biointerfaces, vol. 42, pp. 29-43, (2005).

Akhras, "Bare metal stent, lunar IrOx2 coated or drug-eluting stent for patients with CAD?", PowerPoint presentation, pp. 1-20, Oct. 2006.
Akhras, Comparison of Iridiumoxide Coated Stent with Paclitaxel-Eluting Stent and a Bare Metal Stent in Patients With Coronary Artery Disease; Abstract, 1 page, Oct. 2006.
Al-Lamee, "Programmable Elution Profile Coating for Drug-Eluting Stents," Medical Device Technology: Materials, pp. 12-15, Mar. 2005.
Amanatides et al., "Electrical and optical properties of CH4/H2 RF plasmas for diamond-like thin film deposition," Diamond & Related materials, vol. 14, pp. 292-295, (2005).
Amberg et al., "Silver Deposition on Temperature Sensitive Substrates by Means of an Inverted Cylindrical Magnetron," Poster, 1 page, 2003.
Anders, "Ion Plating and Beyond: Pushing the Limits of Energetic Deposition," Vacuum Technology & Coating, pp. 41-46, Dec. 2002.
Andersson et al., "Influence of Systematically Varied Nanoscale Topography on the Morphology of Epithelial Cells," IEEE Transactions on Nanobioscience, vol. 2, No. 2, pp. 49-57, Jun. 2003.
Andersson et al., "Nanoscale features influence epithelial cell morphology and cytokine production," Biomaterials, 2003. vol. 24, No. 20, pp. 3427-3436, (2003).
Annis et al., "An Elastomeric Vascular Prosthesis," Transactions—American Society for Artificial Internal Organs. vol. XXIV, pp. 209-214, (1978).
Ansell et al., "X-Ray Rhotoelectron Spectroscopic Studies of Tin Electrodes after Polarization in Sodium Hydroxide Solution," Journal of Electrochemical Society: Electrochemical Science and Technology, vol. 124, No. 9, pp. 1360-1364, Sep. 1977.
Antunes et al., "Characterization of Corrosion Products Formed on Steels in the First Months of Atmospheric Exposure", Materia, vol. 8, No. 1, pp. 27-34, (2003).
Armani et al., "Microfabrication Technology for Polycaprolactone, a Biodegradable Polymer," Journal of Micromechanics and Microengineering, vol. 10, pp. 80-84, (2000).
Arnold et al., "Activation of Integrin Function by Nanopatterned Adhesive Interface," ChemPhysChem, vol. 5, pp. 383-388, (2004).
Ashfold et al., "Pulsed laser ablation and deposition of thin films," Chem. Soc. Rev., vol. 33, pp. 23-31, (2004).
Asoh et al., "Conditions for Fabrication of Ideally Ordered Anodic Porous Alumina Using Pretextured A1," Journal of the Electrochemical Society, vol. 148, pp. B152-B156, (2001).
Atanasoska et al., "XPS Studies on Conducting Polymers: Polypyrrole Films Doped with Perchlorate and Polymeric Anions," Chemistry Materials vol. 4, pp. 988-994, (1992).
Aughenbaugh et al., "Silica sol-gel for the controlled release of antibiotics. II. The effect of synthesis parameters on the in vitro release kinetics of vancomycin," Journal of Biomedical Materials Research, vol. 57, No. 3, pp. 321-326, Dec. 5, 2001.
Awad et al., "Deposition of duplex Al2O3/TiN coatings on aluminum alloys for tribological applications using a combined microplasma oxidation (MPO) and arc ion plating (AIP)," Wear, vol. 260, pp. 215-222, (2006).
AxynTec product review, AxynTec Dunnschichttechnik GmbH (www.axyntec.de), pp. 1-8, (2002).
Ayon et al., "Drug loading of nonopouros TiO2 films," Institute of Physics Publishing, Biomedical Materials, vol. 1, pp. L11-L15, (2006).
Azom, "Porous Coatings for Improved Implant Life—Total Hip Replacements," pp. 1-7, [downloaded Sep. 1, 2005], (http://www.azom.com/Details.asp?ArticleID=1900).
Bak et al., "Electrodeposition of polymer next to the three-phase boundary," Electrochemisty Communications, vol. 7, pp. 1098-1104, (2005).
Balamuguran et al., "Bioactive Sol-Gel Hydroxyapatite Surface for Biomedical Applications-In Vitro Study," Trends in Biomaterials & Artificial Organs, vol. 16, No. 1, pp. 18-20, (2002).
Balas et al., "Formation of Bone-Like Apatite on Organic Polymers Treated with a Silane-Coupling Agent and a Titania Solution," Biomaterials, vol. 27, pp. 1704-1710, (2006).
Balaur et al., "Tailoring the wettability of TiO2 nanotube layers," Electrochemistry Communications, vol. 7, pp. 1066-1070, (2005).

(56) References Cited

OTHER PUBLICATIONS

Banks et al., "Femtosecond Laser-Induced Forward Transfer (LIFT): A Technique for Versatile Micro-Printing Applications," European Conference on Lasers and Electro-Optics and the International Quantum Electronics Conference, 1 page, Jun. 17-22, 2007.

Banks et al., "Nano-droplets Deposited in Microarrays by Femtosecond Ti: Saphire Laser-Induced Forward Transfer," Optoelectronics Reaserch Centre, University of Southhampton, Applied Physics Letters, vol. 89, Issue 19, pp. 1-12, (2006).

Barbucci et al, Micro and nano-structured surfaces,: Journal of Materials Science: Materials in Medicine, vol. 14, No. 8, pp. 721-725, (2003).

Bates et al. "Description of research activites: Block copolymers," Organization for Minnesota Nanotechnology Institute, University of Minnesota, pp. 1-2, (2002).

Bayoumi et al., "Formation of self-organized titania nano-tubes by dealloying and anodic oxidation," Electrochemistry Communications, vol. 8, pp. 38-44, (2006).

Békési et al., "Efficient Submicron Processing of Metals with Femtosecond UV Pulses," Applied Physics A, vol. 76, pp. 355-357 (2003).

Benson, "Drug Delivery Technology and Access," Polygenetics, Inc., pp. 1-10, Oct. 2005.

Benson, "Highly Porous Polymers," American Laboratory, pp. 1-14, Apr. 2003.

Berg et al., "Controlled Drug Release from Porous Polyelectrolyte Multilayers," Biomacromolecules, vol. 7, pp. 357-364, (2006).

Berkland et al., "Controlling surface nano-structure using flow-limited field-injection electrostatic spraying (FFESS) of poly(D,L-lactide-co-glycolide)," Biomaterials, vol. 25, pp. 5649-5658, (2004).

Berry et al., "The fibroblast response to tubes exhibiting internal nanotopography," Biomaterials, vol. 26, No. 24, pp. 4985-4992, (2005).

Biederman et al. "Plasma Polymer-Metal Composite Films," Plasma Deposition, Treatment and Etching of Polymers, pp. 269-320, (1990).

Bock et al., "Anion and water involvement in hydrous Ir oxide redox reactions in acidic solutions," Journal of Electroanalytical Chemistry, vol. 475, pp. 20-27, (1999).

Bolle et al., "Characterization of submicrometer periodic structures produced on polymer surfaces with low-fluence ultraviolet laser radiation," Journal of Applied Physics, vol. 73, No. 7, pp. 3516-3524, Apr. 1, 1993.

Bolzán et al., "The Potentiodynamic behaviour of iridium electrodes in aqueous 3.7 M H2SO4 in the 293-195 K Range," Journal of Electroanalytical Chemistry, vol. 461, pp. 40-51, (1999).

Boulmedais et la., "Controlled Electrodissolution of Polyelectrolyte Multilayers: A Platform Technology Towards the Surface-Initiated Delivery of Drugs," Advanced Functional Materials, vol. 63, pp. 63-70, (2006).

Boura et al., "Endothelial cell—interactions with polyelectrolyte multilayer films," Biomaterials, vol. 26. pp. 4568-4575, (2005).

Bradley et al., "Visuotopic Mapping Through a Multichannel Stimulating Implant in Primate V1," Journal of Neurophysiology, vol. 93, pp. 1659-1670, (2005).

Bretagnol et al., "Functional Micropatterning Surface by Combination of Plasma Polymerization and Lift-Off Process," Plasma Process and Polymers, vol. 3, pp. 30-38, Nov. 14, 2005.

Bretagnol et al., "Surface Functionalization and Patterning Techniques to Design Interfaces for Biomedical and Biosensor Applications," Plasma Processes and Polymers, vol. 3, pp. 443-455, (2006).

Brody et al., "Characterization Nanoscale topography of the Aortic Heart Valve Basement Membrane for Tissue Engineering Heart Valve Scaffold Design," Tissue Engineering, vol. 12, No. 2, pp. 413-421, Nov. 2, 2006.

Bruckner et al., "Metal plasma immersion ion implantation and deposition (MPIIID): chromium on magnesium," Surface and Coatings Technology vol. 103-104, pp. 227-230, (1998).

Brunetti et al., "Oxide/hydroxide films on tin. Part I: Kinetic aspects of the electroformation and electroreductions of the films," Journal of Electroanalytical Chemisty, pp. 1-7, (2007).

Bu et al., "Preparation of nanocrystalline TiO2 porour films from terpineol-ethanol-PEG system," Journal of Materials Science, vol. 41, pp. 2067-2073, (2006).

Bu et al., "Synthesis of TiO2 Porous Thin Films by Polythylene Glycol Templating and Chemistry of the Process," Journal of the European Ceramic Society, vol. 25, pp. 673-679 (2005).

Burmeister et al., "Colloid Monolayers as Versatile Lithographic Masks," Langmuir, vol. 13, pp. 2983-2987, (1997).

Buster et al., "Crystal habits of the Magnesium Hydroxide mineral Brucite within Coral Skeletons," American Geophysical Union Annual Meeting, Abstract and Poster, pp. 1-3, (2006).

Buttiglieri et al., "Endothelization and adherence of leucocytes to nanostructured surfaces," Biomaterials, vol. 24, pp. 2731-2738, (2003).

Calcagno et al., "Structural modification of polymer films by ion irradiation," Nuclear Instruments and Methods in Physics Research, vol. B65, pp. 413-422, (1992).

Carp et al., "Photoinduced Reactivity of Titanium Dioxide," Progress in Solid State Chemistry, vol. 32, pp. 33-177, (2004).

Caruso, "Nanoscale Particle Modifications via Sequential Electrostatic Assembly," Colloids and Colloid Assemblies: Synthesis, Modification, Organization and Utilization of Colloid Particles, pp. 266-269, Mar. 19, 2004.

Cassak, "ART: Bucking the Trend in Bioabsorbable Stents", Windhover Information Inc., In Vivo Jun., pp. 1-14, 2008.

Catledge et al, "Structure and Mechanical Properties of Functionally-Graded Nanostructured Metalloceramic Coatings," Mat. Res. Soc. Symp. Proc. vol. 778, pp. U7.8.1-U7.8.6, (2003).

Catledge et al., "Structural and mechanical properties of nanostructured metalloceramic coatings on cobalt chrome alloys," Applied Physics Letters, vol. 82, No. 10, pp. 1625-1627, Mar. 10, 2003.

Caves et al., "The evolving impact of microfabrication and nanotechnology on stent design," Journal of Vascular Surgery, pp. 1363-1368, Dec. 2006.

Caves et al., "The evolving impact of microfabrication and nanotechnology on stent design," Journal of Vascular Surgury, vol. 44, pp. 1363-1368, (2006).

Cernigoj et al., "Photocatalytically Active TiO2 Thin Films Produced by Surfactant-Assistant Sol-Gel Processing," Thin Solid Films, vol. 495, pp. 327-332, (2006).

Ceruti et al., "Preparation, characterization, cytotoxicity and pharmacokinetics of liposomes containing water-soluble prodrugs of paclitaxel," Journal of Controlled Release, vol. 63, pp. 141-153, (2000).

Champagne et al., "Nanometer-scale scanning sensors fabricated using stencil lithography," Applied Physics Letters, vol. 82, No. 7, pp. 1111-1113, Feb. 17, 2003.

Chandra et al., "Biodegradable Polymers," Progress in Polymer Science, vol. 23, pp. 1273-1335, (1998).

Chang et al., "Preparation and Characterization of Nanostructured Tin Oxide Films by Electrochemical Deposition," Electrochemical and Solid-State Letters, vol. 5, No. 8, pp. C71-C74, (2002).

Chen et al., "Blood compatiblity and sp3/sp2 contents of diamond-like carbon (DLC) synthesized by plasma immersion ion implantation-deposition," Surface and Coatings Technology, vol. 156, pp. 289-294, (2002).

Chen et al., "Fabrication of micro-field emitters on ceramic substrates," Microelectronic Engineering, vol. 84, pp. 94-100, (2007).

Chen et al., "Behavior of Cultured Human Umbilical Vein Endothelial Cells on Titanium Oxie Films Fabricated by Plasma Immersion Ion Implantation and Deposition," Surface & Coatings Technology, vol. 186, pp. 270-276, (2004).

Cheng et al., "Anatase Coating on NiTi Via a Low-Temperature Sol-Gel Route for Improving Corrosion Resistance," Scripta Materialia, vol. 51, pp. 1041-1045, (2004).

Cho et al., "A Novel Route to Three-Dimensionally Ordered Macroporous Polymers by Electron Irradiation of Polymer Colloids" Advanced Materials, vol. 17, No. 1, pp. 120-125, Jan. 6, 2005.

(56) References Cited

OTHER PUBLICATIONS

Cho et al., "Influence of Silica on Shape Memory Effect and Mechanical Properties of Polyurethane-Silica Hybrid," European Polymer Journal, vol. 40, pp. 1343-1348, (2004).
Cho et al., "Preparation and Characterization of Iridium Oxide Thin Films Grown by DC Reactive Sputtering," Japanese Journal of Applied Physics, vol. 36, Part 1, No. 3B, pp. 1722-1727, Mar. 1997.
Choi et al., "Synthesis and Characterization of Diamond-Like Carbon Protective AR Coating," Journal of the Korean Physical Society, vol. 45, p. S864, Dec. 2004.
Chougnet et al., "Substrates do influence the ordering of mesoporous thin films," Journal of Materials Chemistry, vol. 15, pp. 3340-3345, (2005).
Chougnet et al., "The Influence of the Nature of the Substrate on the Ordering of Mesoporous Thin Films," Thin Solid Films, vol. 495, pp. 40-44, (2006).
Chow et al., "Nanostructured Films and Coating by Evaporation, Sputtering, Thermal Spraying, Electro and Electroless Deposition," Handbook of Nanophase and Nanostructured Materials, vol. 1, Chapter 9, pp. 246-272, (2003).
Chow et al., "Preliminary Evaluation of KEM for Fabrication," Proceedings of the 12th General Meeting of JOWOG 31, Livermore, CA, University of California, pp. 1-7, (1996).
Chronakis, "Novel nanocomposites and nanoceramics based on polymer nanofibers using electrospinning process—A review," Journal of Materials Processing Technology, vol. 167, pp. 283-293, (2005).
Chu, "Recent developments and applications of plasma immersion ion implantation," Journal of Vacuum Science Technology, vol. B22, No. 1, pp. 289-296, Jan./Feb. 2004.
Chuang et al., "Titanium Oxide and Polyaniline Core-Shell Nanocomposites," Synthetic Metals, vol. 152, pp. 361-364, (2005).
Chung et al., "Roles of discontinuities in bio-inspired adhesive pads," Journal of The Rolyal Society: Interface, vol. 2, pp. 55-61, Feb. 8, 2005.
Clark, "Micropatterning Cell Adhesiveness", Immobilized Biomolecules in Analysis, Oxford University Press, pp. 95-111, (1998).
Clevy et al., "Micromanipulation and Micro-Assembly Systems," IEEE/RAS International Advanced Robotics Program, IARP'06, Paris, France, pp. 1-6, (2006).
Colina et al., "DNA deposition through laser induced forward transfer," Biosensors and Bioelectronics, vol. 20, pp. 1638-1642, (2005).
Costanzo et al., "Model-Based Simulations to Engineer Nanoporous Thin Films," LPCM Research, Pennsylvania State University, pp. 1-3, (2004), (http://lpcm.esm.psu.edu/~tjy107/research.htm).
Course: C-103, "An Introduction to Physical Vapor Deposition (PVD) Processes," Society of Vacuum Coaters, SVC Education Programs: course description and syllabus, pp. 1-4, Apr. 19, 2008.
Course: C-208, "Sputter Deposition in Manufacturing" Society of Vacuum Coaters, SVC Education Programs: course description and syllabus, pp. 1-5, Apr. 22, 2008.
Csete et al., "The existence of sub-micrometer micromechanical modulation generated by polarized UV laser illumination on polymer surfaces," Materials Science and Engineering C, vol. 23, pp. 939-944, (2003).
Csete et al., "The role of original surface roughness in laser-induced periodic surface structure formation process on poly-carbonate films," Thin Solid Films, vol. 453-454, pp. 114-120, (2004).
Curtis et al. "Cells react to nanoscale order and symmetry in their surroundings," IEEE Transactions on Nanobioscience, vol. 3, No. 1, pp. 61-65, Mar. 2004.
Curtis et al., "Nantotechniques and approaches in biotechnology," Trends in Biotechnology, vol. 19, No. 3, pp. 97-101, Mar. 2001.
Curtis et al., "New Depths in Cell Behaviour: Reactions of Cells to Nanotopography," Biochem, Soc, Symp, vol. 65, pp. 15-26, (1999).
Curtis et al., "New depths in cell behaviour: Reactions of cells to nanotopography," Biochemical Society Symposium, No. 65, pp. 15-26 (1997).
Curtis et al., "Topographical Controls of Cells," Biomaterials, vol. 18, pp. 1573-1583, (1997).
Curtis, "Tutorial on the biology of nanotopography," IEEE Transactions on Nanobioscience, vol. 3, No. 4, pp. 293-295, Dec. 2004.
Cyster et al., "The effect of surface chemistry and nanotopography of titanium nitride (TiN) films on 3T3-L1 fibroblasts," Journal of Biomedical Materials Research: A., vol. 67, No. 1, pp. 138-147, Oct. 2003.
Cyster et al., "The effect of surface chemistry and nanotopography of titanium nitride (TiN) films on primary hippocampal neurones," Biomaterials, vol. 25, pp. 97-107, (2004).
da Cruz et al., "Preparation, structure and electrochemistry of a polypyrrole hybrid film with [Pd(dmit)2]2-, bis(1,3-dithiole-2-thione-4,5-dithiolate)palladate(II)," Electrochimica Acta, vol. 52, pp. 1899-1909, (2007).
Dalby et al., "In vitro reaction of endothelial cells to polymer demixed nanotopography," Biomaterials, vol. 23, No. 14, pp. 2945-2954, (2002).
Dalby, "Topographically induced direct cell mechanotransduction," Medical Engineering & Physics, vol. 27, No. 9, pp. 730-742, (2005).
Damen et al., "Paclitaxel Esters of Malic Acid as Prodrugs with Improved Water Solubility," Bioorganic & Medicinal Chemistry, vol. 8, pp. 427-432, (2000).
D'Aquino, "Good Drug Therapy: It's Not Just the Molecule—It's the Delivery," CEP Magazine, (www.cepmagazine.org), 3 pages, Feb. 2004.
Datta et al., "Fundamental aspects and applicatio of electrochemical microfabrication," Electrochimica Acta, vol. 45, pp. 2535-2558, (2000).
Daxini et al., "Micropatterned polymer surface inprove retention of endothelial cells exposed to flow-induced shear stress," Biorheology, vol. 43, pp. 45-55, (2006).
De Aza et al., "Crack growth resistance of alumina, zirconia and zirconia toughened alumina ceramics for joint prostheses," Biomaterials, vol. 23, No. 3, pp. 937-945, Feb. 2002.
Deakin et al., "De-alloying of type 316 stainless steel in hot, concentrated sodium hydroxide solution," Corrosion Science, vol. 46, pp. 2117-2133, (2004).
Debiotech, "Debiostar, An Innovative Solution for Sustained Drug Delivery," pp. 1-4, Copyright 2001, (http://www.debiotech.com/products/drugdd/stent_page_1.html).
Debiotech, "Debiostent: An Innovatice Ceramic Coating for Implantable Medical Devices," pp. 1-2, [first downloaded on Sep. 1, 2005], (http://www.debiotech.com/products/drugdd/stent_page_1.html).
Debiotech, "Debiostent: Polymer free drug eluting coating," Jun. 14, 2007, pp. 1-2, (www.debiotech.com/products/druggd/stent_page_1.html).
Debiotech, "Debiotech Obtains Exclusive Rights to an Innovative Drug Eluting Stent Technology," Press release, 1 page, Mar. 7, 2003.
Demisse, "Computational Investigation of Conducting Polythiophenes and Substituted Polythiophenes," A Thesis Submitted to the School of Graduate Studies of Addis Ababa University, Ethiopia, pp. 1-86, Jun. 2007.
Deniau et al., "Study of the polymers obtained by electroreduction of methacrylonitrile," Journal of Electroanalytical Chemistry, vol. 505, pp. 33-43, (2001).
Desai et al., "Characterization of micromachined silicon membranes for imrnunoisolation and bioseparation applications," Journal of Membrane Science, vol. 159, pp. 221-231, (1999).
Desai et al., "Use of Microfabricated 'Nanopore' Membranes as a Rate-Limiting Barrier to Diffusion of Small and Large Molecules: Possible Role in Drug Delivery" BioMEMs and Nanotechnology World, pp. 1-2, (2001).
Desai, Integrating Cells with Microsystems: Application in Tissue Engineering and Cell-Based Delivery, PowerPoint presentation, pp. 1-41, May 10, 2002.
Di Mario et al., "Drug-eluting bioabsorbable magnesium stent," Journal of Interventional Cardiology, vol. 17, Issue 6, pp. 1-5, Dec. 2004.
Di Mario et al., "Moonlight: a controlled registry of an iridium oxide-coated stent with angographic follow-up," International Journal of Cardiology, vol. 95, pp. 329-331, (2004).

(56) References Cited

OTHER PUBLICATIONS

Di Mario, The Moonlight Study: Multicenter Objective Observational Lunar Iridium Oxide Intimal Growth Trial, PowerPoint presentation, pp. 1-10, (2002).
Dibra et al., "Influence of the stent surface topology on the outcomes of patients undergoing coronary stenting: a randomized double-blind controlled trial", Catheterization and Cardiovascular Interventions, vol. 65, pp. 374-380, (2005).
Dittmar et al., "Nanostructured Smart Drug Delivery Coatings," European Cells and Materials, vol. 31, Supplement 2, p. 73, (2007).
Dong et al., "Preparation of Submicron Polypyrrole/Poly(methly methacrylate) Coaxial Fibers and conversion to Polypyrrole Tubes and Carbon Tubes," Langmuir, vol. 22, pp. 11384-11387, (2006).
Doraiswamy et al., "Excimer laser forward transfer of mammalian cells using a novel triazene absorbing layer," Applied Surface Science, vol. 252, pp. 4743-4747, (2006).
DTI Technology Group: Materials-Coating, "Kinetic spray coating method," www.delphi.com, 1 page, Jul. 2004.
Dumas et al., "Characterization of magnesium fluride thin films produced by argon ion beam-assisted deposition," Thin Solid Films, vol. 382, pp. 61-68, (2001).
Duncan et al., "Polymer-drug conjugates, PDEPT and PELT: basic principals for design and transfer from laboratory to clinic," Journal of Controlled Release, vol. 74, pp. 135-146, (2001).
Duncan, "The Dawning Era of Polymer Therapeutics," Nature Reviews: Drug Discovery, vol. 2, pp. 347-360, May 2003.
Dutta et al., "Self-Organization of Colloidal Nanoparticles," Encyclopedia of Nanoscience and Nanotechnology, vol. 9, pp. 617-640, (2003).
Duwez et al., "Mechanochemistry: targeted delivery of single molecules," Nature Nanotechnology, vol. 1, pp. 122-125, (2006).
EAG Technical Note, "Functional Sites on Non-polymeric Materials: Gas Plasma Treatment and Surface Analysis," Evans Analytical Group, pp. 1-2, (2003).
Eberli et al., "The Lunar Coronary Stent System," Handbook of coronary stents, 4th edition, Chapter 17, 11 pages, (Martin Dunitz Ltd 2002).
Eesley et al., "Thermal properties of kinetics spray Al—SiC metal-matrix composite," Journal of Materials Research, vol. 18, No. 4, pp. 855-860, Apr. 2003.
Egerhazi et al., "Thickness distribution of carbon nitride films grown by inverse-pulsed laster deposition," Applied Surface Science, vol. 247, pp. 182-187, (2005).
Electropolymerization, (http://intel.ucc.ie/sensors/Electropolym.htm), pp. 1-2, (downloaded [2007]).
Erlebacher et al., "Evolution of nonoporosity in dealloying," Nature, vol. 410, pp. 450-453, Mar. 22, 2001.
Esrom et al., "New approach of a laser-induced forward transfer for deposition of patterned thin metal films," Applied Surface Science, vol. 86, pp. 202-207, (1995).
Faupel et al., "Microstructure of pulsed laser deposited ceramic-metal and polymer-metal nanocomposite thin films," Applied Physics A, vol. 79, pp. 1233-1235 (2004).
Faust et al., "Biofunctionalised Biocompatible Titania Coatings for Implants," Euro Ceramics VII, Key Engineering Materials, vol. 206, No. 2, pp. 1547-1550, (2006).
Fernandez-Pradas et al., "Laser-induced forward transfer of biomolecules," Thin Solid Films, vol. 453-454, pp. 27-30, (2004).
Ferraz et al., "Influence of nanoporesize on platelet adhesion and activation," Journal of Materials Science: Materials in Medicine, vol. 19, pp. 3115-3121, (2008).
Figallo et al., "Micropatterned Biopolymer 3D Scaffold for Static and Dynamic Culture of Human Fibroblasts," Biotechnology Progress, vol. 23, pp. 210-216, (2007).
Finkelstein et al., "Local drug delivery via a coronary stent with programmable release pharmakinetics," Circulation, vol. 107, pp. 777-784, Jan. 13, 2003.
Flemming et al., "Effects of synthetic micro- and nano-structured surfaces on cell behavior," Biomaterials, vol. 20, No. 6, pp. 573-588, (1999).

Fogarassy et al., "Laser-induced forward transfer: A new approach for the deposition of high Tc superconducting thin films," Journal of Materials Research, vol. 4, No. 5, pp. 1082-1086, Sep./Oct. 1989.
Fonseca et al., "Paclitaxel-loaded PLGA nanoparticles: preparation, physicochemical characterization and in vitro anti-tumoral activity," Journal of Controlled Release, vol. 83 pp. 273-286, (2002).
Forty, "Corrosion micromorphology of noble metal alloys and depletion gilding," Nature, vol. 282, pp. 597-598, Dec. 6, 1979.
Frechet, "Functional Polymers: from Plastic Electronics to Polymer-Assisted Therapeutics," Progress in Polymer Science, vol. 30, pp. 844-857, (2005).
Free Online Dictionary, "Aperture," definition, [first viewed Oct. 9, 2009].
Freitas et al., "Nimesulide PLA microsphere as a potential sustained release system for the treatment of inflammatory diseases," International Journal of Pharmaceutics, Vo. 295, pp. 201-211, (2005).
Freitas, "Nanomedicine, vol. I: Basic Capabilities," Landes Bioscience, pp. 87, 90, 255 and 265, (1999).
Friedrich et al., "Developing Interdisciplinary Undergraduate and Graduate Courses Through the Integration of Recent Research Results into the Curricula," (http://www.ineer.org/Events/ICEE1997/Proceedings/paper326.htm), 10 pages, [first downloaded Mar. 10, 2005.].
Fu et al., "Effects of mesh-assisted carbon plasma immersion ion implantation on the surface propoerties of insulating silicon carbide ceramics," Journal of Vacuum Science Technology, vol. A22, No. 2, pp. 356-360, Mar./Apr. 2004.
Fu et al., "Influence of thickness and dielectric properties on implantation efficacy in plasma immersion ion implantation of insulators," Journal of Applied Physics, vol. 95, No. 7, pp. 3319-3323, Apr. 1, 2004.
Fujisawa et al., "A novel textured surface for blood-contact," Biomaterials, vol. 20, pp. 955-962, (1999).
Fulton, "Ion-Assisted Filtered Cathodic Arc Deposition (IFCAD) System for Volume Production of Thin-Film Coatings," Society of Vacuum Coaters, 42nd Annual Technical Conference Proceedings, (1999).
Gabel et al., "Solid-State Spray Forming of Aluminum Near-Net Shapes," Journal of Metals, vol. 49, No. 8, pp. 31-33, (1997).
Gabel, "Low Temperature Metal Coating Method," Lawrence Livermore National Laboratory, p. 1-4, Apr. 3, 2000.
Gadegaard et al., "Tubes with Controllable Internal Nanotopography," Advanced Materials, vol. 16, No. 20, pp. 1857-1860, Oct. 18, 2004.
Galinski et al., "Ionic liquids as electrolytes," Electrochimica Acta, vol. 51, 5567-5580, (2006).
Gao, "Chemical Vapor Deposition," Handbook of Nanophase and Nanostructured Materials, vol. 1: Synthesis, Chapter 5, (2003).
Geretovszky et al., "Correlation of compositional and structural changes during pulsed laser deposition of tantalum oxide films," Thin Solid Films, vol. 453-454, pp. 245-250, (2004).
Gillanders et al., "A Composite Sol-Gel/Fluoropolymer Matrix for Dissolved Oxygen Optical Sensing," Journal of Photochemistry and Photobiology A: Chemistry, vol. 163, pp. 193-199, (2004).
Glocker et al., "AC Reactive Sputtering with Inverted Cylindrical Magnetrons," Society of Vacuum Coaters, 43rd Annual Technical Conference Proceedings—Denver, pp. 81-85, Apr. 15-20, 2000.
Glocker et al., "Recent developments in inverted cylindrical magnetron sputtering," PowerPoint presentation, pp. 1-21, (2001).
Glocker et al., "Recent developments in inverted cylindrical magnetron sputtering," Surface and Coatings Technology, vol. 146-147, pp. 457-462, (2001).
Goddard et al., "Polymer surface modification for the attachmend of bioactive compounds," Progress in Polymer Science, vol. 32, pp. 698-725, (2007).
Goh et al., "Nanostructuring Titania by Embossing with Polymer Molds Made from Anodic Alumina Templates," Nano Letters, vol. 5, No. 8, pp. 1545-1559, (2005).
Gollwitzer et al., "Titania Coating as Local "Drug" Delivery System with Antibacterial and Biocompatible Properties," 1 page, (2003).
Gong et al., "Controlled molecular release using nanopourous alumina capsules," Biomedical Microdevices, vol. 5, No. 1, pp. 75-80, Mar. 2003.

(56) References Cited

OTHER PUBLICATIONS

Gong et al., "Titanium oxide nanotube arrays prepared by anodic oxidation," Journal of Material Research, vol. 16, No. 12, pp. 3331-3334, (2001).
Goodison et al., "CD44 cell adhesion molecules," Journal of Clinical Pathology: Molecular Pathology, vol. 52, pp. 189-196, (1999).
Goodman et al., "Three-dimensional extracellular matrix textured biomaterials," Biomaterials, vol. 17, pp. 2087-2295, (1996).
Gorb et al., "Biological microtribology: anisotropy in frictional forces of orthopteran attachment pads reflects the unitrastructure of a highly deformable material," Proceeding of the Royal Society, London series B, vol. 267, pp. 1239-1244, (2000).
Gotszalk et al., "Diagnostics of micro- and nanostructure using the scanning probe microscopy," Journal of Telecommunications and Information Technology, pp. 41-46, (2005).
Granqvist et al., "Biodegradable and bioactive hybrid organic-inorganic PEG-siloxane fibers: Preparation and Characterization," Colloid Polymer Science, vol. 282, pp. 495-501, (2004).
Greeley et al., "Electrochemical dissolution of surface alloys in acids: Thermodynamic trends from first-principles calculations," Electrochimica Acta, vol. 52, pp. 5829-5836, (2007).
Green et al., "XPS Characterisation of Surface Modified Ni-Ti Shape Memory Alloy," Materials Science and Engineering, vol. A224, pp. 21-26, (1997).
Gressel-Michel et al., "From a Microwave Flash-Synthesized TiO2 Colloidal Suspension to TiO2 Thin Films," Journal of Colloid and Interface Science, vol. 285, pp. 674-679, (2005).
Groth et al., "Layer-by-Layer Deposition of Polyelectrolytes—A Versatile Tool for the In Vivo Repair of Blood Vessels," Angewandte Chemie, International Edition, vol. 43, pp. 926-928, (2004).
Grubmuller, "What happens if the Room at the Bottom Runs Out? A Close Look at Small Water Pores," PNAS, vol. 100, No. 13, pp. 7421-7422, Jun. 24, 2003.
Gu et al., "Biomimetic titanium dioxide film with structural color and extremely stable hydrophilicity," Applied Physics Letters, vol. 85, No. 21, pp. 5067-5069 (2004).
Guangliang et al., "The effects of current density on the phase composition and microstructure properties of micro-arc oxidation coating," Journal of Alloys and Compounds, vol. 345, pp. 169-200, (2002).
Guo et al., "Formation of oxygen bubbles and its influence on current efficiency in micro-arc oxidation process of AZ91D magnesium alloy," Thin Solid Films, vol. 485, pp. 53-58, (2005).
Guo et al., "Growth of ceramic coatings on AZ91D magnesium alloys by micro-arc oxidation in aluminate-fluoride solutions and evalucation of corrosion resistance," Applied Surface Science, col. 246, pp. 229-238, (2005).
Guo et al., "Investigation of corrosion behaviors of Mg—6Gd—3Y—0.4Zr alloy in NaCl aqueous solutions," Electrochimica Acta, vol. 52, pp. 2570-2579, (2007).
Guo et al., "Sol gel derived photocatalytic porous TiO2 thin films," Surface & Coatings Technology, vol. 198, pp. 24-29, (2005).
GVD Corporation, "Nanocoatings for a New Era," pp. 1-3, [first downloaded Nov. 12, 2003].
Haag et al., "Polymer Therapeutics: Concepts and Applications," Angewandte Chemie, vol. 45, pp. 1198-1215, (2006).
Haberland et al., "Filling of micron-sized contact holes with copper by energetic cluster impact," Journal of Vacuum Science Technology A, vol. 12, No. 5, pp. 2925-2930, Sep./Oct. 1994.
Haery et al., "Drug-eluting stents: The beginning of the end of restenosis?," Cleveland Clinic Journal of Medicine, vol. 71, No. 10, pp. 815-824, (2004).
Hahn et al., "A novel approach for the formation of Mg(OH)2/MgO nanowhiskers on magnesium: Rapid anodization in chloride containing solutions", Electrochemistry Communications, vol. 10, pp. 288-292, (2008).
Halme et al., "Spray Deposition and Compression of TiO2 Nanoparticle Films for Dye-Sensitized Solar Cells on Plastic Substrates," Solar Energy Materials & Solar Cells, vol. 90, pp. 887-899, (2006).

Hamley et al., "Nanostructure fabrication using block copolymers," Nanotechnology, vol. 14, pp. R39-R54, (2003).
Han et al., "Electron injection enhancement by diamond-like carbon film in organic electroluminescence devices," Thin Solid Films, vol. 420-421, pp. 190-194, (2002).
Han et al., "Pourous nanocrystalline titania films by plasma electrolytic oxidation," Surface and Coatings Technology, vol. 154, pp. 314-318, (2002).
Han et al., "Structure and in vitro bioactivity of titania-based films by micro-arc oxidation," Surface and Coatings Technology, vol. 168, pp. 249-258, (2003).
Han et al., "Synthesis of nanocrystalline titaniaa films by micro-arc oxidation," Materials Letters, vol. 56, pp. 744-747, (2002).
Hanley et al., "The growth and modification of materials via ion-surface processing," Surface Science, vol. 500, pp. 500-522, (2002).
Harris et al., "Fabrication of Perforated Thin Films with Helical and Chevron Pore Shapes," Electrochemical and Solid-State Letters, vol. 4, pp. C39-C42, (2004).
Harvard Nanopore, "Ion Beam Sculpting: Material Science—Fabricating Nanopores and Other Nanoscale Feature," pp. 1-5, [first downloaded Jul. 2, 2003], (http://www.mcb.harvard.edu.branton/projects-IonBeam/htm).
Hattori et al., "Photoreactivity of Sol-Gel TiO2 Films Formed on Soda-Lime Glass Substrates: Effect of SiO2 Underlayer Containing Fluorine," Langmuir, vol. 15, pp. 5422-5425, (1999).
Hau et al., "Surface-chemistry technology for microfluidics," Journal of Micromechanics and Microengineering, vol. 13, pp. 272-278, (2003).
Hausleiter et al., "Prvention of restenosis by a novel drug-eluting stent system with a dose-adjustable, polymer-free, on-site stent coating," European Heart Journal, vol. 26, pp. 1475-1481, (2005).
He et al., "Electrochemical Fabrication of Metal Nanowires," Encyclopedia of Nanoscience and Nanotechnology, vol. X, pp. 1-18, (2003).
He et al., "Optical properties of diamond-like carbon synthesized by plasma immersion ion processing," Journal of Vacuum Science Technology, vol. B17, No. 2, pp. 822-827, Mar./Apr. 1999.
Heidenau et al., "Structured Porous Titania as a Coating for Implant Materials," Key Eng Mater. vol. 192-195, pp. 87-90, (2001).
Heinig et al., "Modeling and Simulation of Ion Beam Systhesis of Nanoclusters," 6 pages, [first downloaded Jan. 3, 2000], (http://www.fz-rossendorf.de/pls/rois/Cms?pOId=10960&pFunc=Print&pLang=de).
Helmersson et al., "Ionized physical vapor deposition (IPVD): A review of technology and applications," Thin Solid Films, vol. 513, pp. 1-24, (2006).
Helmus et al. "Surface Analysis of a Series of Copolymers of L-Glutamic Acid and L-Leucine," Journal of Colloid and Interface Science, vol. 89, No. 2, pp. 567-570, (1982).
Helmus et al., "Plasma Interaction on Block Copolymers as Determined by Platelet Adhesion," Biomaterials: Interfacial Phenomena and Applications: Chapter 7, pp. 80-93, (1981).
Helmus et al., "The Effect of Surface Charge on Arterial Thrombosis," Journal of Biomedical Materials Research, vol. 18, pp. 165-183, (1984).
Hentze et al., "Porous polymers and resins for biotechnological and biomedical applications," Reviews in Molecular Biology, vol. 90, pp. 27-53, (2002).
Hoa et al., "Preparation of porous meterials with ordered hole structure," Advances in Colloid and Interface Science, vol. 121, pp. 9-23, (2006).
Hoffman, "Non-Fouling Surface Technologies," Journal of Biomaterials Science, Polymer Edition, vol. 10, No. 10, pp. 1011-1014, (1999).
Hoglund, "Controllable Degradation Product Migration From Biomedical Polyester-ethers," KTH Chemical Science and Engineering, Stockholm, pp. 1-52, May 24, 2007.
Holland et al., "Synthesis of Macroporous Minerals with Highly Ordered Three-Dimensional Arrays of Spheroidal Voids," Science, vol. 281, pp. 538-540, Jul. 24, 1998.

(56) References Cited

OTHER PUBLICATIONS

Hong et al., "The super-hydrophilicities of Bi—TiO2, V—TiO2, and Bi—V—TiO2 nano-sized particles and their benzene photodecompositions with H2O addition," Materials Letters, vol. 60, pp. 1296-1305, (2006).

Hopp et al., "Absorbing film assisted laser induced forward transfer of fungi (*Trichoderma conidia*)," Journal of Applied Physics, vol. 96, No. 6, pp. 3478-3481, Sep. 15, 2004.

Houbertz, "Laser interaction in sol-gel based materials—3-D lithography for photonic applications," Applied Surface Science, vol. 247, pp. 504-512, (2005).

Houdayer et al., "Preparation of new antimony(0)/polyaniline nanocomposites by a one-pot solution phase method," Materials Letter, vol. 61, pp. 171-176, (2007).

Hrudey et al., "Organic Alq3 Nanostructures Fabricated with Glancing Angle Depostion," Vacuum Technology & Coating, pp. 1-6, May 2006.

Hsiao et al., "Soluble aromatic polyamides bearing asymmetrical diaryl ether groups," Polymer, vol. 45, pp. 7877-7885, (2004).

Hu et al., "Cyclic voltammetric deposition of hydrous ruthenium oxide for electrochemical capacitors: effects of codeposting iridium oxide," Electrochimica Acta, vol. 45, pp. 2684-2696, (2000).

Hu et al., "Voltammetric investigation of platinum oxides II. Efect of hydration on the reduction behavior," Electrochimica Acta, vol. 45, pp. 3063-3068, (2000).

Hüppauff et al., "Valency and Structure of Iridium in Anodic Iridium Oxide Films," Journal of Electrochemical Society, vol. 140, No. 3, pp. 598-602, Mar. 1993.

Hurley et al., "Nanopatterning of Alkynes on Hydrogen-Terminated Silicon Surfaces by Scanning Probe-Induced Cathodic Eletrografting," Journal of American Chemistry Society, vol. 125, pp. 11334-11339, (2003).

Hussain et al., "Atomic force microscope study of three-dimensional nanostructure sidewalls," Nanotechnology, vol. 18, pp. 1-8, (2007).

Ichinose et al., "A surface sol-gel process of TiO2 and other metal oxide films with molecular precision," Chem. Mater. vol. 9, pp. 1296-1298, (1997).

Ichinose et al., "Ultrathin composite films: An indispensable resource for nanotechnology," Riken Review, No. 37, pp. 34-37, Jul. 2001.

Ignatova et al., "Combination of Electrografting and Aton-Transfer Radical Polymerization for Making the Stainless Steel Surface Antibacterial and Protein Antiadhesive," Langmuir, vol. 22, pp. 255-262, (2006).

Imai et al., "Preparation of Porous Anatase Coatings from Sol-Gel-Derived Titanium Dioxide and Titanium Dioxide-Silica by Water-Vapor Exposure," Journal of American Ceramics Society, vol. 82, No. 9, pp. 2301-2304, (1999).

Inflow Dynamics starts "LUSTY" Study, Company Press Release: First clinical trial with Niobium stents, (www.tctmd.com/industry-news/one.html?news_id=3364), 1 page, Jun. 25, 2002.

Inoue et al., "Corrosion rate of magnesium and its alloys in buffered chloride solutions," Corrosion Science, vol. 44, pp. 603-610, (2002).

Inovati, "Award Winning—Environmentally-Safe, High-Quality, Metal Spray Process," Press Release, pp. 1-6, (2002), (http://www.inovati.com/papers/KM-PressRelease.doc).

Inovati, "Inovati to Develop Green Metal Coating Technology" Press Release, 1 page, [first downloaded Sep. 1, 2005], (http://www.inovati.com/papers/bmdopr.html).

Inovati, "Low temperature, high-speed sprays make novel coatings," 1 pages, [first downloaded on Mar. 18, 2003], (http://www.inovati.com/papers/ampmar01.html).

Introduction to the Metal Printing Process: Future manufacturing equipment of advanced materials and complex geometrical shapes, (www.mpp.no/intro/intro.htm), pp. 1-2, downloaded Mar. 18, 2002.

Irhayem et al., "Glucose Detection Based on Electrochemically Formed Ir Oxide Films," Journal of Electroanalytical Chemisty, vol. 538-539, pp. 153-164, (2002).

Irvine et al., Nanoscale clustering of RGD peptides at surfaces using Comb polymers. 1. Synthesis and characterization of Comb thin films, Biomacromolecules, vol. 2, No. 1, pp. 85-94, Spring 2001.

Irvine et al., "Nanoscale clustering of RGD peptides at surfaces using comb polymers. 2. Surface segregation of comb polymers in polylactide," Biomacromolecules, vol. 2, No. 2, pp. 545-556, Summer 2001.

Ishizawa et al., "Characterization of thin hydroxyapatite layers formed on anodic titanium oxide films containing Ca and P by hydrothermal treatment," Journal of Biomedical Materials Research, vol. 29, pp. 1071-1079, (1995).

Ishizawa et al., "Histomorphometric evaluation of the thin hydroxyapatite layer formed through anodization followed by hydrothermal treatment," Journal of Biomedical Materials Research, vol. 35, pp. 199-206, (1997).

Isoflux Inc., "Isoflux specializes in vacuum coating equipment and coating process," http://www.isofluxinc.com/about.shtml, 1 page, Jul. 2009.

Iurhayem et al. "Glucose detection based on electrochemically formed Ir oxide films," Journal of Electroanalytical Chemistry, vol. 539-539, pp. 153-164, (2002).

Jensen et al., "Low-temperature preparation of nanocrystalline anatase films through a sol-gel rout," Journal of Sol-Gel Science and Technology, vol. 39, pp. 229-233, (2006).

Jewell et al., "Multilayered polyelectrolyte films promote the direct and localized delivery of DNA to cells," Journal of Controlled Release, vol. 106, pp. 214-223, (2005).

JMAR LLC, "Collimated Plasma Lithography (CPL)," 1 page, [first downloaded Jul. 2, 2003], (http://www.jmar.com/co451.html).

Johnson, "What's an Ionic Liquid?," The Electrochemical Society: Interface, pp. 38-41, Spring 2007.

Juodkazis et al., "Alternative view of anodic surface oxidation of nobel metals," Electrochimica Acta, vol. 51, pp. 6159-6164, (2006).

Kamei et al., "Hydrophobic drawings on hydrophilic surfaces of single crystalline titanium dioxide: surface wettability control by mechanochemical treatment," Surface Science Letters, vol. 463 pp. L609-L612, (2000).

Kanda et al., "Characterization of Hard Diamond-Like Carbon Films Formed by Ar Gas Cluster Ion Beam-Assisted Fullerene Deposition," Japanese Journal of Applied Physics, vol. 41, Part 1, No. 6B, pp. 4295-4298, Jun. 2002.

Kang et al., "Controlled drug release using nanoporous anodic aluminum oxide on stent," Thin Solid Films, vol. 515, pp. 5184-5187, (2007).

Kaplan, "Cold Gas Plasma and Silanes," Presented at the 4th International Symposium on Silanes and Other Coupling Agents, Jul. 11-13, 2003.

Karuppuchamy et al., "Cathodic Electrodeposition of Oxide Semiconductor Thin Films and their Application to Dye-Sensitized Solar Cells," Solid State Ionics, vol. 151, pp. 19-27, (2002).

Karuppuchamy et al., "Photoinduced Hydrophilicity of Titanium Dioxide Thin Films Prepared by Cathodic Electrode position," Vacuum, vol. 80, pp. 494-498, (2006).

Karuppuchamy et al., "Super-hydrophilic amorphous titanium dioxide thin film deposited by cathodic electrodeposition," Materials Chemisty and Physics, vol. 93, pp. 251-254, (2005).

Karuri et al., "Biological length scale topography enhances cell-substratum adhesion of human corneal epithelial cells," Journal of Cell Science, vol. 117, No. 15, pp. 3153-3164, (2004).

Kasemo et al., "Implant surfaces and interface processes," Adv. Dent. Res. vol. 13, pp. 8-20 Jun. 1999.

Kasemo, "Biological surface science," Surface Science, vol. 500, pp. 656-677, (2002).

Kato et al., "N-succinyl-chitosan as a drug carrier: water-insoluble and water-soluble conjugates," Biomaterials, vol. 25, pp. 907-915, (2004).

Katsumata et at., "Effect of Microstructure on Photoinduced Hydrophilicity of Transparent Anatase Thin Films," Surface Science, vol. 579, pp. 123-130, (2005).

Katz, "Developments in Medical Polymers for Biomaterials Applications," Medical Device Link, pp. 1-9, Jan. 2001, (http://www.devicelink.com/mddi/archive/01/01/003.html).

Kean et al. "The Analysis of Coatings Produced by Accelerated Nanoparticles," Mantis Deposition Ltd., Presentaction at NSTI Nano Tech 2006, Boston, May 7-11, pp. 1-4, 2006.

(56) References Cited

OTHER PUBLICATIONS

Kesapragada et al., "Two-component nanopillar arrays grown by Glancing Angle Deposition," Thin Solid Films, vol. 494, pp. 234-239, (2006).

Kesler et al., "Enhanced Strength of Endothelial Attachment on Polyester Elastomer and Polytetrafluoroethylene graft Surfaces with Fibronectin Substrate," Journal of Vascular Surgery, vol. 3, No. 1, pp. 58-64, (1986).

Kesting, "Synthetic Polymeric Membranes—A Structural Perspective", Chapters 6-7, pp. 225-286, Oct. 1985.

Kickelbick, "Concepts for the incorporation of inorganic building blocks into organic polymers on a nanoscale," Progress in Polymer Science, vol. 28, pp. 81-114, (2003).

Kidambi et al., "Selective Depositions on Polyelectrolyte Multilayers: Self-Assembled Monolayers on m-dPEG Acid as Molecular Template," Journal of the American Chemistry Society, vol. 82, No. 9, pp. 4697-4703, (2004).

Kilian et al., "Plasma transglutaminase factor XIII induces microvessel ingrowth into biodegradable hydroxyapatite implants in rats," Biomaterials, vol. 26, pp. 1819-1827, (2005).

Kim et al. "Porous ZrO2 bone scaffold coated with hydroxyapatite with fluorapatite intermediate layer," Biomaterials, vol. 24, pp. 3277-3284, (2003).

Kim et al., "Adhesion of RF bias-sputtered Cr thin films onto photosensitivepolyimide substrates," IEEE, International Symposium on Eelectrical Materials and Pakaging, pp. 202-207, (2001).

Kim et al., "Fabrication of WC—Co coatings by cold spray deposition," Surface & Coatings Technology, vol. 191, pp. 335-340, (2005).

Kim et al., "Hollow Silica Spheres of Controlled Size and Porosity by Sol-Gel Processing," Journal of Americal Ceramic Society, vol. 74, Nol. 8, pp. 1987-1992, (1991).

Kim et al., "Proton conducting polydimethylsiloxane/metal oxide hybrid membranes added with phosphotungstic acid(II)," Electrochimica Acta, vol. 49, pp. 3429-3433, (2004).

Kim et al., "Fabrication and Characterization of TiO2 Thin Film Prepared by a Layer-by-Layer Self-Assembly Method," Thin Solid Films, vol. 499, pp. 83-89, (2006).

Kitagawa et al., "Near-Edge X-Ray Absorption Fine Structure Study for Optimization of Hard Diamond-Like Carbon Film Formation with Ar Cluster Ion Beam," Japanese Journal of Applied Physics, vol. 42, pp. 3971-3975, (2003).

Kitagawa et al., Optimum Incident Angle of Ar Cluster Ion Beam for Superhard Carbon Film Deposition, Japanese Journal of Applied Physics, vol. 43, No. 6B, pp. 3955-3958, (2004).

Kittaka et al., "The Structure of Water Monolayers on a Hydroxylated Chromium Oxide Surface," Adsorption, vol. 11, pp. 103-107, (2005).

Kleinertz et al., "LUSTY Studie: Lunar STF Study," PowerPoint presentation, pp. 1-24, Sep. 4, 2004.

Kleisner et al., "A system based on metal alkyl species that forms chemically bound organic overlays on hydroxylated planar surfaces," Thin Solid Films, vol. 381, pp. 10-14, (2001).

Kogure et al., "Microstructure of nemalite, fibrous iron-bearing brucite", Mineralogical Journal, vol. 20, No. 3, pp. 127-133, Jul. 1998.

Kohli et al., "Arrays of lipid bilayers and liposomes on patterned polyelectrolyte templates," Journal of Colloid and Interface Science, vol. 301, pp. 461-469, (2006).

Kokubo et al., "Novel bioactive materials with different mechanical properties," Biomaterials, vol. 24, pp. 2161-2175, (2003).

Kommireddy et al., "Layer-by-Layer Assembly of TiO2 Nanoparticles for Stable Hydrophilic Biocompatible Coatings" Journal of Nanoscience and Nanotechnology, vol. 5, pp. 1081-1087, (2005).

Kondyurin et al., "Plasma Immersion ion implantation of polyethylene," Vacuum, vol. 64, pp. 105-111, (2002).

Kong et al., "Polyelectrolyte-functionalized multiwalled carbon nanotubes: preparation, characterization and layer-by-layer self-assembly," Polymer, vol. 46, pp. 2472-2485, (2005).

Konig et al., "Nanoprocessing with nanojoule near-infrared femtosecond laser pulses," Medical Laser Application, vol. 20, pp. 169-184, (2005).

Konishi et al., "Morphology Control of Dy-Ni Alloy Films by Electrochemical Displantation," Electrochemical and Solid-State Letters, vol. 5, No. 12, pp. B37-B39, (2002).

Koo et al., "Co-regulation of cell adhesion by nanoscale RGD organization and mechanical stimulus," Journal of Cellular Science, vol. 115, Part 7, pp. 1423-1433, Apr. 1, 2002.

Kopanski et al., "Scanning Kelvin Force Microscopy for Characterizing Nanostructures in Atmosphere," Characterization and Metrology for Nanoelectronics: 2007 International Conference on Frontiers of Characterization and Metrology. American Institute of Physics Conference Proceedings, vol. 931, pp. 530-534, Sep. 26, 2007.

Kostov et al., "Two Dimensional Computer Simulation of Plasma Immersion Ion Implantation," Brazilian Journal of Physics, vol. 34, No. 4B, pp. 1689-1695, Dec. 2004.

Kötz et al., "XPS Studies of Oxygen Evolution on Ruand RuO2 Anodes," Journal of Electrochemical Society: Electrochemical Science and Technology, pp. 825-829, Apr. 1983.

Kowalski et al., "Corrosion protection of steel by bi-layered polypyrrole doped with molybdophosphate and naphthalenedisulfonate anions," Corrosion Science, Vo. 49, pp. 1635-1644, (2007).

Kraft et al., "Thin films from fast clusters: golden TiN layers on a room temperature substrate" Surface and Coatings Technology 158-159, pp. 131-135, (2002).

Krumeich et al., "HyFraSurf-Advanced Surface Technology for Superior Electrode Performance," European Cells and Materials, vol. 1, Suppl. 1, p. 43, (2001).

Kumar et al., "Influence of electric field type on the assembly of single walled carbon nanotubes," Chemical Physics Letters, vol. 383, pp. 235-239, (2004).

Kumar et al., "Polyanhydrides: an overview," Advanced Drug Delivery Reviews, vol. 54, pp. 889-910, (2002).

Kunitake et al., "Molecular imprinting in ultrathin titania gel films via surface sol-gel process," Analytica Chimica Acta, vol. 504, pp. 1-6, (2004).

Kurth et al., "Multilayers on Solid Planar Substrates: From Structure to Function," Multilayer Thin Films: Sequential Assembly of Nanocomposite Materials, Chapter 14, pp. 393-426, Mar. 7, 2003.

Kutsenko et al., "Structural changes in Mg alloy induced by plasma immersion ion implantation of Ag," Acta Materialia, vol. 52, pp. 4329-4335, (2004).

Kutz, "Biomaterials to Promote Tissue Regeneration," in Standard Handbook of Biomedical Engineering and Design, ISBN 0-07-135637-1, pp. 16.13-16.29, (2003).

Kvastek et al., "Electochemical properties of hydrous rithenium oxide films formed and measured at different potentials," Journal of Electroanalytical Chemistry, vol. 511, pp. 65-78, (2001).

Lakard et al., "Adhesion and proliferation of cells on new polymers modified biomaterials," Bioelectrochemistry, vol. 62, pp. 19-27, (2004).

Lakatos-Varsanyi et al., "Cyclic voltammetry measurements of different single-, bi- and multilayer TiN and single layer CrN coatings on low-carbon-steel substrates," Corrosion Science, vol. 41, pp. 1585-1598, (1999).

Lamaka et al., "TiOx self-assembled networks prepared by templating approach as nanostructured reservoirs for self-healing anticorrosion pre-treatments," Electrochemistry Comunications, vol. 8, pp. 421-428, (2006).

Larner et al., "The Challenge of Plasma Processing—Its Diversity," Presented at the ASM Materials and Processes for Medical Devices Conference, Aug. 25-27, 2004.

Laser-Induced Forward Transfer (LIFT): Paul Scherrer Institut, (http://materials.web.psi.ch/Research/Thin_Films/Methods/LIFT.htm), pp. 1-2, downloaded Dec. 7, 2006.

Lau et al., "Hot-wire chemical vapor deposition (HWCVD) of fluorocarbon and organosilicon thin films," Thin Solid Films, vol. 395, pp. 288-291, (2001).

LaVan et al., Small-scale systems for in vivo drug delivery, Nature Biotechnology, vol. 21, No. 10, pp. 1184-1191, Oct. 2003.

(56) References Cited

OTHER PUBLICATIONS

Leary-Swan et al., "Fabrication and evaluation of nanoporous alumina membranes for osteoblast culture," Journal of Biomedical Materials Research: Part A, vol. 72A, pp. 288-295, (2005).

Lee et al., "A Template-Based Electrochemical Method for the Synthesis of Multisegmented Metallic Nanotubes," Angewandte Chemie, vol. 44, pp. 6050-6054, (2005).

Lee et al., "Biocompatibility and Charge Injection Property of Iridium Film Formed by Ion Beam Assisted Deposition," Biomaterials, vol. 24, pp. 2225-2231, (2003).

Lee et al., "Structural characterization of porous low-k thin films prepared by different techniques using x-ray porosimetry," Journal of Applied Physics, vol. 95, No. 5, Mar. 1, 2004.

Lee et al., "A study on electrophoretic deposition of Ni nanoparticles on pitted Ni alloy 600 with surface fractality", Journal of Colloid and Interface Science, vol. 308, pp. 413-420, (2007).

Lefaux et al., "Polyelectrolyte Spin Assembly: Influence of Ionic Strenght on the Growth of Multilayered Thin Films," Journal of Polymer Science Part B: Polymer Physics, vol. 42, pp. 3654-3666, (2004).

Lei et al., "Fabrication of Highly Ordered Nanoparticle Arrays Using Thin Porous Alumina Masks," Advanced Materials for Micro- and Nano-Systems (AMMNS), pp. 1-6, Jan. 2001.

Leng et al., "Mechanical properties and platelet adhesion behavior of diamond-like carbon films synthesized by pulsed vacuum arc plasma deposition," Surface Science, vol. 531, pp. 177-184, (2003).

Lenza et al., "In vitro release kinetics of proteins from bioactive foams," Journal of Biomedical Materials Research: A, vol. 67, No. 1, pp. 121-129, Oct. 2003.

Leoni et al., "Characterization of Nanoporous Membranes for immunoisolation: Diffusion Properties and Tissue Effects," Biomedical Microdevices, vol. 4, No. 2, pp. 131-139, (2002).

Leoni et al., "Nanoporous Platforms for Cellular Sensing and Delivery," Sensors, 51(2), pp. 111-120, (2002).

Leung et al., "Fabrication of photonic band gap crystal using microtransfer molded templates," Journal of Applied Physics, vol. 93, No. 10, pp. 5866-5870, May 15, 2003.

Lewis et al., "Silicon nonopillars formed with gold colloidal partical masking," Journal of Vacuum Science Technology B, vol. 16, No. 6, pp. 2938-2941, Nov./Dec. 1998.

Li et al., "A simple approach to fabricate amorphous silicon pattern on single crystal silicon," Tribology International, vol. 40, pp. 360-364, (2007).

Li et al., "Bioactive Hydroxyapatite Composite Coating Prepared by Sol-Gel Process," Journal of Sol-Gel Science and Technology, vol. 7, pp. 27-34, (1996).

Li et al., "Fabrication and Microstructuring of Hexagonally Ordered Two-Dimensional Nanopore Arrays in Anodic Alumina," Advanced Materials, vol. 11, pp. 483-487, (1999).

Li et al., "Hexagonal pore arrays with a 50-420 nm interpore distance formed by self-organization in anodic alumina," Journal of Applied Physics, vol. 84, No. 11, pp. 6023-6026, Dec. 1, 1998.

Li et al., "Improved biological performance of Ti implants due to surface modification by micro-arc oxidation," Biomaterials, vol. 25, pp. 2867-2875, (2004).

Li et al., "On the growth of highly ordered pores in anodized aluminum oxide," Chem. Mater., vol. 10, pp. 2470-2480, (1999).

Li et al., "pH-compensation effect of bioactive inorganic fillers on the degradation of PLGA," Composites Science and Technology, vol. 65, pp. 2226-2232, (2005).

Li et al., "Polycrystalline nanopore arrays with haxagonal ordering on aluminum," Journal of Vacuum Science Technology: A, vol. 17, pp. 1428-1431, (1999).

Li et al., "A novel method for preparing surface-modified Mg(OH)2 nanocrystallines," Materials Science and Engineering A, 452-453, pp. 302-305, (2007).

Li, "Poly(L-glutamic acid)-anticancer drug conjugates," Advanced Drug Delivery Reviews, vol. 54, pp. 695-713, (2002).

Liaw et al., "Process Monitoring of Plasma Electrolytic Oxidation," presented at the 16th World Conference on Nondestructive Testing, Montreal, Canada, pp. 1-7, Aug. 30-Sep. 3, 2004.

Liebling et al., "Optical Properties of Fibrous Brucite from Asbestos, Quebec", American Mineralogist, vol. 57, pp. 857-864, (1972).

Lim et al., "Systematic variation in osteoblast adhesion and phenotype with substratum surface characteristics," Journal of Biomedical Materials and Research, vol. 68A, No. 3, pp. 504-511, (2004).

Lim et al., "UV-Driven Reversible Switching of a Roselike Vanadium Oxide Film between Superhydrophobicity and Superhydrophilicity," Journal of American Chemical Society, vol. 129, pp. 4126-4129, Mar. 15, 2007.

Lin et al., "PWA-doped PEG/SiO2 proton-conducting hybrid membranes for fuel cell applications," Journal of Membrane Science, vol. 254, pp. 197-205, (2005).

Lindstrom et al., "A New Method for Manufacturing Nanostructured Electrodes on Glass Substrates," Solar Energy Materials & Solar Cells, vol. 73, pp. 91-101 (2002).

Lippert et al., "Chemical and Spectroscopic Aspects of Polymer Ablation: Special Features and Novel Directions," Chemical Reviews, vol. 103, pp. 453-485, (2003).

Liu et al., "A metal plasma source ion implantation and deposition system," American Institute of Physics, Review of Scientific Instruments, vol. 70, No. 3, pp. 1816-1820, Mar. 1999.

Liu et al., "Electrodeposition of Polypyrrole Films on Aluminum from Tartrate Aqueous Solution," Journal of Brazilian Chemical Society, vol. 18, No. 1, pp. 143-152, (2007).

Liu et al., "Surface modification of titanium, titanium alloys, and related materials for biomedical applications," Materials Science and Engineering R, vol. 47, pp. 49-121, (2004).

Lu et al., "Fabricating Conducting Polymer Electrochromic Devices Using Ionic Liquids," Journal of The Electrochemical Society, vol. 151, No. 2, pp. H33-H39, (2004).

Lu et al., "Micro and nano-fabrication of biodegradable polymers for drug delivery," Advanced Drug Delivery Reviews, vol. 56, pp. 1621-1633, (2004).

Lv et al., "Controlled growth of three morphological structures of magnesium hydroxide nanoparticles by wet precipitation method," Journal of Crystal Growth, vol. 267, pp. 676-684, (2004).

Lv et al., "Controlled synthesis of magnesium hydroxide nanoparticles with different morphological structures and related properties in flame retardant ethyolene-vinyl acetate blends", Nanotechnology, vol. 15, pp. 1576-1581, (2004).

Lv et al., "In situ synthesis of nanolamellas of hydrophobic magnesium hydroxide", Colloids and Surfaces A: Physicochemical and Engineering Aspects, vol. 296, pp. 97-103, (2007).

Maeda et al., "Effect of Silica Addition on Crystallinity and Photo-Induced Hydrophilicity of Titania-Silica Mixed Films Prepared by Sol-Gel Process," Thin Solid Films, vol. 483, pp. 102-106, (2005).

Maehara et al., "Buildup of Multilayer Structures of Organic-Inorganic Hybrid Ultra Thin Films by Wet Process," Thin Solid Films, vol. 438-439, pp. 65-69, (2003).

Maheshwari et al., "Cell adhesion and motility depend on nanoscale RGD clustering," Journal of Cell Science, vol. 113, Part 10, pp. 1677-1686, May 2000.

Maitz et al., "Blood Compatibility of Titanium Oxides with Various Crystal Structure and Element Doping," Journal of Biomaterials Applications, vol. 17, pp. 303-319, Apr. 2003.

Manna et al., "Microstructural Evalution of Laser Surface Alloying of Titanium with Iridium," Scripta Materialia, vol. 37, No. 5, pp. 561-568, (1997).

Manoharan et al., "Ordered macroporous rutile titanium dioxide by emulsion templating," Proceedings of SPIE, vol. 3937, pp. 44-50, (2000).

Mantis Deposition Ltd., "Nanocluster Deposition," Thame, Oxforshire, United Kingdom, pp. 1-2, [downloaded on Feb. 2, 2007], (http://www.mantisdeposition.corn/nanocluster.html).

Martin et al., "Microfabricated Drug Delivery Systems: Concepts to Improve Clinical Benefit," Biomedical Microdevices, vol. 3, No. 2, pp. 97-107, Jun. 2001.

Martin, "Pulsed Laser Deposition and Plasma Plume Investigations," Andor Technology, Ltd. pp. 1-3, (2003).

(56) References Cited

OTHER PUBLICATIONS

Masuda et al., "Highly ordered nanochannel-array architecture in anodic alumina," Applied Physics Letters, vol. 71, pp. 2770-2772, (1997).
Matijević, "Colloid Chemical Aspects of Corrosion of Metals", Pure & Applied Chemisty, vol. 52, pp. 1179-1193, (1980).
Mattox, "Introduction: Physical Vapor Deposition (PVD) Processes," Vacuum Technology & Coating, pp. 60-63, Jul. 2002.
Mattox, "The History of Vacuum Coating Technology: Part V," Vacuum Technology & Coating, pp. 32-37, Oct. 2002.
Mattox, "The History of Vacuum Coating Technology: Part VI," Vacuum Technology & Coating, pp. 52-59, Oct. 2002.
Mauritz Group Homepage, "Sol-Gel Chemistry and Technology," (htty://www.psrc.usin.edu/mauritz/solgel.html), pp. 1-10, (downloaded [2006]).
McGuigan et al., "The influence of biomaterials on endothelial cell thrombogenicity," Biomaterials, vol. 28, pp. 2547-2571, (2007).
McNally et at., "Cathodic Electrodeposition of Cobalt Oxide Films Using Polyelectrolytes," Materials Chemistry and Physics, vol. 91, pp. 391-398, (2005).
Meijer et al., "Laser Machining by short and ultrashort pulses, state of the art and new opportunities in the age of the photons," Annals of CIRP 2002: Manufacturing Technology, vol. 51, No. 2, pp. 531-550, (2002).
Meletis et al., "Electrolytic plasma processing for cleaning and metal-coating of steel surfaces," Surface and Coatings Technology, vol. 150, pp. 246-256, (2002).
Merriam-Webster's Dictionary Website: For definition of Strut, 1 page,[first cited Jul. 21, 2010], (http://www.merriam-webster.com/dictionary/strut).
MicroFab Technologies Inc. "MicroFab: Biomedical Applications—Stents," pp. 1-4, [first downloaded Mar. 23, 2007], (http://www.microfab.com/technology/biomedical/Stents.html).
Mikhaylova et al., "Nanowire formation by electrodeposition in modified nanoporous polycrystalline anodic alumina templates," Mat. Res. Soc. Symp. Proc., vol. 704, pp. w6.34.1-W6.34.6, (2002).
Miller et al., "Endothelial and vascular smooth muscle cell function on poly(lactic-co-glycolic acid) with nano-structured surface features," Biomaterials, vol. 25, No. 1, pp. 53-61, (2004).
Miller et al., "Mechanism(s) of increased vascular cell adhesion on nanostructured poly(lactic-co-glycolic acid) films," Journal of Biomedical Materials Research A, vol. 73, No. 4, pp. 476-484, (2005).
MIV Therapeutics, "Hydroxyapatite Coating," pp. 1-4, [first downloaded Jun. 25, 2003], (http://www.mivtherapeutics.com/technology/hap/).
Mobedi et al., "Studying the Degradation of Poly(L-lactide) in Presence of Magnesium Hydroxide", Iranian Polymer Journal, vol. 15, No. 1, pp. 31-39, (2006).
Mu et al., "A novel controlled release formulation for the anticancer drug paclitaxel (Taxol): PLGA nanoparticles containing vitamin E TPGS," Journal of Controlled Release, vol. 86, pp. 33-48, (2003).
Mu et al., "Vitamin E TPGS used as emulsifier in the solvent evaporation/extraction technique for fabrication of polymeric nanospheres O for controlled release of paclitaxel (Taxol)", Journal of Controlled Release, vol. 80, pp. 129-144, (2002).
Muller et al., "Solid lipid nanoparticles (SLN) for controlled drug delivery: a review of the state of the art," European Journal of Pharmaceutics and Biopharmaceutics, vol. 50, pp. 161-177, (2000).
Munchow et al., "Poly[(oligoethylene glycol) Dihydroxytitanate] as Organic-Inorganic Polymer-Electrolytes," Electrochimica Acta, vol. 45, pp. 1211-1221, (2000).
Murray et al., "Electrosynthesis of novel photochemically active inherently conducting polymers using an ionic liquid electrolyte," Electrochimica Acta, vol. 51, pp. 2471-2476, (2006).
Naganuma et al., "Preparation of Sol-Gel Derived Titanium Oxide Thin Films Using Vacuum Ultraviolet irradiation with a Xenon Excimer Lamp," Japanese Journal of Applied Physics, vol. 43, No. 9A, pp. 6315-6318, (2004).
Nair et al., "Biodegradable polymers as biomaterials", Progress in Polymer Science, vol. 32, pp. 732-798, (2007).

Nakajima et al., "Effect of Vacuum Ultraviolet Light Illumination on the Crystallization of Sol-Gel-Derived Titanium Dioxide Precursor Films," Surface & Coatings Technology, vol. 192, pp. 112-116, (2005).
Nakayama et al., "Fabrication of drug-eluting covered stents with micropores and differential coating of heparin and FK506," Cardiovascular Radiation Medicine, vol. 4, pp. 77-82, (2003).
NanoBiotech News, vol. 2, No. 26, pp. 1-9, Jun. 30, 2004.
Nanoparticle coatings: Application note, "Antimicrobial Coatings," MANTIS Deposition Ltd, pp. 1-2, (2006).
Nanu, "Nanostructured TiO2—CuInS2 based solar cells," Symposium D, Thin Film and Nano-Structured Materials for Photovoltaics, E-MRS Spring Meeting 2003, pp. 1-2, Jun. 10-13, 2003.
NASA Glenn Research Center, "Fast Three-Dimensional Method of Modeling Atomic Oxygen Undercutting of Protected Polymers," pp. 1-6, [first downloaded on Jul. 3, 2003], (http://www.grc.nasa.gov/WWW/epbranch/suurtxt/surfaceabs.htm).
Neves et al., "The morphology, mechanical properties and ageing behavior of porous injection molded starch-based blends for tissue engineering scafolding," Materials Science and Engineering, vol. C25, pp. 195-200, (2005).
Newman et al., "Alloy Corrosion," MRS Bulletin, pp. 24-28, Jul. 1999.
Ngaruiya et al., "Structure formation upon reactive direct current magnetron sputtering of transition metal oxide films," Applied Physics Letters, vol. 85, No. 5, pp. 748-750, Aug. 2, 2004.
Ngaruiya et al., "The reactive DC-Magnetron Sputtering Process,", pp. 1-5, (circa 2004).
Nicoll et al., "In vitro release kinetics of biologically active transforming growth factor-beta 1 from a novel porous glass carrier," Biomaterials, vol. 18, Issue 12, pp. 853-859, (1997).
Nicoll et al., "Nanotechnology and Biomaterials—Drugs, Drug Delivery Systems, Quantum Dots and Disease Treatment," Azom.com, pp. 1-5, [first downloaded Mar. 22, 2004], (http://www.azom.com/details.asp?ArticleID=1853).
Nie et al., "Deposition of layered bioceramic hydroxyapatite/TiO2 coatings on titanium alloys using a hybrid technique of micro-arc oxidation and electrophoresis," Surface Coatings Technology, vol. 125, pp. 407-414, (2000).
Nishio et al., "Preparation and properties of electrochromic iridium oxide thin film by sol-gel process," Thin Solid Films, vol. 350, pp. 96-100, (1999).
Noguera et al., "3D fine scale ceramic components formed by ink-jet prototyping process," Journal of the European Ceramic Society, vol. 25, pp. 2055-2059, (2005).
O'Brien et al., "Passivation of Nitinol Wire for Vascular Implants—A Demonstration of the Benefits," Biomaterials, vol. 23, pp. 1739-1748, (2002).
Oh et al., "Microstructural characterization of biomedical titanium oxide film fabricated by electrochemical method," Surface & Coatings Technology, vol. 198, pp. 247-252, (2005).
Orloff et al., "Biodegradable implant strategies for inhibition of restenosis," Advanced Drug Delivery Reviews, vol. 24, pp. 3-9, (1997).
Oxford Applied Research, "Nanocluster Deposition Systems—Nanodep60," 1 page, [first downloaded Nov. 3, 2006], (http://www.oaresearch.co.uk.nanodep60.htm).
Paik et al., "Micromachining of mesoporous oxide films for microelectromechanical system structures," Journal of Materials Research, vol. 17, pp. 2121-2129, (2002).
Palasis et al., "Analysis of Adenoviral Transport Mechanisms in the Vessel Wall and Optimization of Gene Transfer Using Local Delivery Catheters," Human Gene Therapy, vol. 11, pp. 237-246, Jan. 20, 2000.
Palasis et al., "Site-Specific Drug Delivery from Hydrogel Coated Angioplasty Catheters," Proceedings of the International Symposium on Controlled Release: Bioactive Materials, vol. 24, pp. 825-826, (1997).
Palmaz et al., "Influence of surface topography on endothelialization of intravascular metallic material," Journal of Vascular and Interventional Radiology, vol. 10, No. 4, pp. 439-444, (1999).

(56) References Cited

OTHER PUBLICATIONS

Pang et al., "Electrodeposition of composite hydroxyapatite-chitosan films," Materials Chemistry and Physics, vol. 94, pp. 245-251, (2005).
Pang et al., "Electropolymerization of high quality electrochromic poly(3-alkyl-thiophene)s via a room termperature ionic liquid," Electrochimica Acta, vol. 52, pp. 6172-6177, (2007).
Park et al., "Multilayer Transfer Printing for Polyelectrolyte Multilayer Patterning. Direct Transfer of Layer-by-Layer Assembled Micropatterned Thin Films," Advanced Materials, vol. 16, No. 6, pp. 520-525, Mar. 18, 2004.
Park et al., "Novel Phenylethynyl Imide Silanes as Coupling Agents for Titanium Alloy," The 22nd Annual Meeting of the Adhesion Society, pp. 1-5, Feb. 21-24, 1999.
Park et al., "Cathodic electrodeposition of Ru02 thin films from Ru(III)C13 solution", Materials Chemistry and Physics, vol. 87, pp. 59-66, (2004).
Park et al., "Microstructural change and precipitation hardeningin melt-spun Mg—X—Ca alloys," Science and Technology of Advanced Materials, vol. 2, pp. 73-78, (2001).
Pathan et al., "A chemical route to room-temperature synthesis of nanocrystalline TiO2 thin films," Applied Surface Science, vol. 246, pp. 72-76, (2005).
Pelletier et al., "Plasma-based ion implantation and deposition: A review for physics, technology, and applications," Lawrence Berkeley and National Laboratory, pp. 1-68, May 16, 2005.
Peng et al., "Role of polymers in improving the results of stenting in coronary arteries," Biomaterials, vol. 17, No. 7, pp. 658-694 (1996).
Perlman et al., "Evidence for rapid onset of apoptosis in medial smooth muscle cells after balloon injury," Circulation, vol. 95, No. 4, pp. 981-987, Feb. 18, 1997.
Pharmaceutical Science Technology, Chapter 6: Electropolymerization, pp. 24-28, (2007).
Piazza et al., "Protective diamond-like carbon coatings for future optical storage disks," Diamond & Related Materials, vol. 14, pp. 994-999, (2005).
Pitt et al., "Attachment of hyaluronan to metallic surfaces," Journal of Biomedical Materials Research, vol. 68A, pp. 95-106, (2004).
Polygenetics, "Advanaced Drug Delivery," [first downloaded on May 4, 2007], 5 pages, (http://www.polygenetics.com/drug_delivery.htm).
Ponte et al., "Porosity determination of nickel coatings on copper by anodic voltammetry," Journal of Applied Electrochemistry, vol. 32, pp. 641-646, (2002).
Prior Clinicals, Boston Scientific memo, pp. 1-2, (more than a year prior to May 23, 2007).
Prokopowicz et al., "Synthesis and Application of Doxorubicin-Loaded Silica Gels as Solid Materials for Spectral Analysis," Talanta, vol. 65, pp. 663-671, (2005).
Prokopowicz et al., "Utilization of Standards Generated in the Process of Thermal Decomposition Chemically Modified Silica Gel or a Single Point Calibration of a GC/FID System," Talanta, vol. 44, pp. 1551-1561, (1997).
Pulsed Laser Deposition, (http://www.physandtech.net), pp. 1-7, Apr. 28, 2001.
PVD Materials—Materials Available for Physical Vapour Deposition (PVD) from Williams Advanced Materials. (www.azom.com), pp. 1-8, [first downloaded Apr. 28, 2006].
Qasem et al., "Kinetics of Paclitaxel 2'-N-Methylpyridinium Mesylate Decomposition," AAPS PharmaSciTech, vol. 4, No. 2, Article 21, pp. 1-8, (2003).
Qian et al., "Preparation, characterization and enzyme inhibition of methylmethacrylate copolymer nanoparticles with different hydrophilic polymeric chains," European Polyer Journal, vol. 42, pp. 1653-1661, (2006).
Qiang et al., "Hard coatings (TiN, Ti$\chi$Al1-$\chi$N) deposited at room temperature by energetic cluster impact," Surface and Coatings Technology, 100-101, pp. 27-32, (1998).
Qiu et al., "Self-assembled growth of MgO nanosheet arrays via a micro-arc oxidations technique," Applied Surface Science vol. 253, pp. 3987-3990, (2007).
Radin et al., "Biocompatible and Resorbable Silica Xerogel as a Long-Term Controlled Release Carrier of Vancomycin," Orthopaedic Research Society, 47th Annual Meeting, Feb. 25-28, 2001, San Francisco, CA.
Radin et al., "Silica sol-gel for the controlled release of antibiotics. I. Synthesis, characterization, and in vitro release," Journal of Biomedical Materials Research, vol. 27, No. 2, pp. 313-320, Nov. 2001.
Radin, et al., "In vitro bioactivity and degradation behavior of silica xerogels intended as controlled release materials," Biomaterials. vol. 23, No. 15, pp. 3113-3122, Aug. 2002.
Radtchenko et al., "A Novel Method for Encapsulation of Poorly Water-Soluble Drugs: precipitation in Polyelectrolyte multilayer shells", International Journal of Pharmaceutics, vol. 242, pp. 219-223, (2002).
Razzacki et al., "Integrated microsystems for controlled drug delivery," Advanced Drug Delivery Reviews, vol. 56, pp. 185-198, (2004).
Rees et al., "Glycoproteins in the Recognition of Substratum by Cultured Fibroblasts," Symposia of the Society for Experimental Biology: Cell-Cell Recognition, No. 32, pp. 241-260 (1978).
Reyna-Gonzales et al., "Influence of the acidity level on the electropolymerization of N-vinylcarbazole: Electrochemical study and characterization of poly(3,6-N-vinylcarbazole)," Polymer, vol. 47, pp. 6664-6672, (2006).
Rice, "Limitations of pore-stress concentrations on the mechanical properties of porous materials," Journal of Material Science, vol. 32, pp. 4731-4736, (1997).
Ristoscu, "Thin Films and Nanostructured Materials." pp. 1-2, [first downloaded Jul. 3, 2003], (http://www..fisica.unile.it/radiazioni/ThinY02Ofilms%20and%20nanostmctured%20materials.htm).
Robbie et al., "Advanced techniques for glancing angle deposition," Journal of Vacuum Science and Technology B, vol. 16, No. 3, pp. 1115-1122, (May/Jun. 1998).
Robbie et al., "Sculptured thin films and glancing angle deposition: Growth mechanics and applications," Journal of Vacuum Science Technology: A., vol. 15, pp. 1460-1465, (1997).
Roder et al., "Tuning the microstructure of pulsed laser deposited polymer-metal nanocomposites," Applied Physics A. vol. 85, pp. 15-20 (2006).
Rosen et al., "Fibrous Capsule Formation and Fibroblast Interactions at Charged Hydrogel Interfaces," Hydrogels or Medical and Related Applications, Chapter 24, pp. 329-343, Jun. 1, 1976.
Rossi et al., "Pulsed Power Modulators for Surface Treatment by Plasma Immersion Ion Impantation," Brazilian Journal of Physics, vol. 34, No. 4B, pp. 1565-1571, Dec. 2004.
Routkevitch, "Nano- and Microfabrication with Anodic Alumina: A Route to Nanodevices," Foresight Institute 9th Conference on Molecular Nanotechnology, pp. 1-20, Nov. 8-11, 2001, Santa Clara, CA.
Ryu et al., "Biomimetic apatite induction on Ca-containing titania," Current Applied Physics, vol. 5, pp. 512-515, (2005).
Santos et al., "Si—Ca—P xerogels and bone morphogenetic protein act synergistically on rat stromal marrow cell differentiation in vitro," Journal of Biomedical Materials Research, vol. 41, No. 1, pp. 87-94, Jul. 1998.
Santos et al., "Sol-Gel Derived Carrier for the Controlled Release of Proteins," Biomaterials, vol. 20, pp. 1695-1700, (1999).
Sardella et al., "Plasma-Aided Micro- and Nanopatterning Processes for Biomedical Applications," Plasma Processes and Polymers, vol. 3, pp. 456-469, (2006).
Sasahara et al., "Macroporous and nanosized ceramic films prepared by modified sol-gel methods with PMMA microsphere templates," Journal of the European Ceramic Society, vol. 24, pp. 1961-1967, (2004).
Sawitowski, "Nanoporous alumina for implant coating—A novel approach towards local therapy," NanoMed 3rd Workshop, Medical Applications of Nanotechnology, Berlin, 1 page, Feb. 17-18, 2003.
Sawyer et al., "The Role of Electrochemical Surface Properties in Thrombosis at Vascular Interfaces: Cumulative Experience of Studies in Animals and Man," Bulletin of the New York Academy of Medicine, Second Series, vol. 48, No. 2, pp. 235-256, (1972).

(56) References Cited

OTHER PUBLICATIONS

Sawyer, "Electrode-Biologic Tissue Interreactions at Interfaces—A Review;" Biomat. Med. Dev. Art. Org., 12(3-4), pp. 161-196 (1984).
Schetsky, "Shape Memory Alloys", Encyclopedia of Chemical Technology (3rd ed.), John Wiley & Sons, vol. 20, pp. 726-736, (1982).
Schlottig et al., "Characterization of nanoscale metal structures obtained by template synthesis," Fresenius' Journal of Analytical Chemistry, vol. 361, pp. 684-686, (1998).
Schneider, "Laser Cladding with Powder: Effect of some machining parameters on clad properties," Doctoral Thesis—University of Twente, The Netherlands, pp. 1-176, ISBN 9036510988, Mar. 1998.
Schnitzler et al., "Organic/Inorganic Hybrid Materials Formed From TiO2 Nanoparticles and Polyaniline," Journal of Brazilian Chemistry Society, vol. 15, No. 3, pp. 378-384, (2004).
Selective laser sintering, from Wikipedia, (http://en.wikipedia.org/wiki/Selective_laser_sintering), pp. 1-2, downloaded on Sep. 28, 2007.
Senior et al., "Synthesis of tough nanoporous metals by controlled electrolytic dealloying," Nanotechnology, vol. 17, pp. 2311-2316, (2006).
Serra et al., "Preparation of functional DNA microarrays through laser-induced forward transfer," Applied Physics Letters, vol. 85, No. 9, pp. 1639-1641, Aug. 30, 2004.
Serruys et al., "The Effect of Variable Dose and Release Kinetics on Neointimal Hyperplasia Using a Novel Paclitaxel—Eluting Stent Platform," Journal of the American College of Cardiology, vol. 46, No. 2, pp. 253-260, Jul. 19, 2005.
Sgura et al., The Lunar Stent: characteristics and clinical results, Herz, vol. 27, pp. 1-14, (2002).
Shabalovskaya et al., "Surface Conditions of Nitinol Wires, Tubing, and As-Cast Alloys. The Effect of Chemical Etching, Aging in Boiling Water, and Heat Treatment," Wiley Periodicals, Inc., Journal of Biomedical Materials Research Part B: Appiled Biomaterials, vol. 65B: pp. 193-203, (2003).
Shamiryan et al., "Comparative study of SiOCH low-k films with varied porosity interacting with etching and cleaning plasma," Journal of Vacuum Science Technology B, vol. 20, No. 5, pp. 1923-1928, Sep./Oct. 2002.
Shang et al., "Structure and photocatalytic characters of TiO2 film photocatalyst coated on stainless steel webnet," Journal of Molecular Catalysis A: Chemical, vol. 202, pp. 187-1995, (2003).
Shao et al., "Fiber mats of poly(vinyl alcohol)/silica composite via Electrospinning," Materials Letters, vol. 57, pp. 1579-1584, (2003).
Shehukin et al., "Micron-scale hollow polyelectrolyte capsules with naosized magnetic Fe3O4 inside," Materials Letters, vol. 57, pp. 1743-1747, (2003).
Shevchenko et al., "Porous Surface of NiTi Alloy Produced by Plasma Ion Implantation," Institute of Ion Beam Physics and Materials Research, 1 page, May 2005.
Shevchenko, "Formation of nonoporous structures on stainless steel surface," Report, pp. 1-6, Apr. 2007.
Shibli et al., "Development of phosphate inter layered hydroxyapatite coating for stainless steel implants", Applied Surface Science, vol. 254, pp. 4103-4110, (2008).
Shockravi et al., "Soluable and thermally stable polyamides bearing 1,1'-thiobis(2-naphthoxy) groups," European Polymer Journal, vol. 43, pp. 620-627, (2007).
Shustak et al., "n-Alkanoic Acid Monolayers on 316L Stainless Steel Promote the Adhesion of electropolymerized Polypyrrole Films," Langmuir, vol. 22, pp. 5237-5240, (2006).
Siegfried et al., "Reactive Cylindrical Magnatron Deposition of Titanium Nitride and Zirconium Nitride Films," Society of Vacuum Coaters, 39th Annual Technical Conference Proceedings, pp. 97-101, (1996).
Silber et al., "A new stainless-steel-free stent with a potential of artifact free magnetic resonance compatibility: first clinical experience (Ein neuer Edelstahl-freier Stent mit Potential zur artefaktfreien MR-Kompatibilität: Erste klinische Erfahrungen)," German Society for Cardiology—Heart and Cardiovascular Research (Deutche Gesellschaft fur Kardiologie—Herz und Kreislaufforschung), 1 page, Oct. 30, 2005.
Silber et al., "A new stainless-steel-free stent with a potential of artifact free magnetic resonance compatibility: first clinical experience," Abstract and Poster, pp. 1-3, May 2006.
Silber, "LUSTY-Fim Study: Lunar Starflex First in Man Study," PowerPoint presentation at the Paris Course on Revascularization, pp. 1-11, May 2003.
Silber, "Ein edelstahfreier stent aus niobium mit iridiumoxyd (IrOx)-beschichtung: Erste Ergebnisse der LUSTY-studie" (Stainless steel-free Stent out of niobium with iridiumoxyd (IrOx)-coating: Initial results of the LUSTY-study), PowerPoint presentation, pp. 1-16, Oct. 15, 2004.
Silber, "LUSTY-Fim Study: Lunar Starflex First In Man Study," PowerPoint presentation, pp. 1-16, 2003.
Silber, "Niobium/iridiumoxide Stents: LUSTY randomized trial, Lunar ROX registry," PowerPoint presentation, pp. 1-33, 2003.
Silva et al., "Electrochemical characterisation of oxide films formed on Ti-6A1-4V alloy implanted with Ir for Bioengineering applications," Electrochimica Acta, vol. 43, Nos. 1-2, pp. 203-211, (1998).
Simon et al., "Influence of topography on endothelialization of stents: Clues for new designs," Journal of Long-Term Effects of Medical Implants, Voo. 10, No. 1-2, pp. 143-151, (2000).
Singer, "Paclitaxel Poliglumex (XYOTAX, CT-2103): A Macromolecular Taxane," Journal of Controlled Release, vol. 109, 120-126, (2005).
Singh et al., "Review: Nano and macro-structured component fabrication by electron beam-physical vapor deposition (EB-PVD)," Journal of Materials Science, vol. 40, pp. 1-26, (2005).
Sniadecki et al., "Nanotechnology for Cell-Substrate Interactions," Annals of Biomedical Engineering, vol. 34, No. 1, pp. 59-74, Jan. 1, 2006.
Sofield et al., "Ion beam modification of polymers," Nuclear Instruments and Methods in Physics Research, vol. B67, pp. 432-437, (1992).
Soler-Illia et al., "Block Copolymer-Templated Mesoporous Oxides," Current Opinion in Colloid and Interface Science, vol. 8, pp. 109-126, (2003).
Song et al., "Biomimetic apatite coatings on micro-arc oxidized titania," Biomaterials, vol. 25, pp. 3341-3349, (2004).
Sousa et al., "New Frontiers in Cardiology: Drug-Eluting Stents: Part I," Circulation: Journal of the Americal Heart Associate, vol. 107, pp. 2274-2279, http/www.circ.ahajournals.org, (2003).
Spasova et al., "Magnetic and optical tunable microspheres with a magnetite/gold nanoparticle shell," Journal of Material Chemisty, vol. 115, pp. 2095-2098, (2005).
Sprague et al., "Endothelial cell migration onto metal stent surfaces under static and flow conditions," Journal of Long-Term Effects of Medical Implants, vol. 10, No. 1-2, pp. 97-110, (2000).
Startschuss fur "lusty"-studie, (Launch of "lusty"-study), Cardio News, 1 page, Oct. 2002.
Stucky "High Surface Area Materials," pp. 1-5, Published: Jan. 1998, WTEC Hyper-Librarian, (http://www.wtec.org/loyola/nano/US.Review/07_03.htm).
Studart et al., "Colloidal Stabilization of Nanoparticles in Concentrated Suspensions," Langmuir, vol. 23, pp. 1081-1090, (2007).
Sun et al., "Construction of Size-Controllable Hierarchical Nanoporous TiO2 Ring Arrays and Their Modifications," Chem. Mater, vol. 18, pp. 3774-3779, (2006).
Sun et al., "Non-Fouling Biomaterial Surfaces: II Protein Adsorption on Radiation Grafted Polyethylene Glycol Methacrylate Copolymers," Polymer Preprints, vol. 28, No. 1, pp. 292-294, Apr. 1987.
Sundararajan et al., "Mechanisms underlying the formation of thick alumina coatings through the MAO coating technology," Surface and Coatings Technolgy, vol. 167, pp. 269-277, (2003).
Sung et al., "Formation of Nanoporous and Nanocrystalline Anatase Films by Pyrolysis of PEO-TiO2 Hybrid Films," Journal of Crystal Growth, vol. 286, pp. 173-177, (2006).
Szycher et al., "Drug-Eluting Stents to Prevent Coronary Restenosis," CardioTech International, pp. 1-10, (2002).

(56) References Cited

OTHER PUBLICATIONS

Tabata et al., "Generalized Semiempirical Equations for the Extrapolated Range of Electronics," Nuclear Instruments and Methods, vol. 103, pp. 85-91, Mar. 28, 1972.
Takitani et al., "Desorption of Helium from Austenitic Stainless Steel Heavily Bombarded by Low Energy He Ions," Journal of Nuclear Materials, vol. 329-333, pp. 761-765, (2004).
Tamura et al., "Surface Hydroxyl Site Densities on Metal Oxides as a Measrure for the Ion-Exchange Capacity," Journal of Colloid and Interface Science, vol. 209, pp. 225-231, (1999).
Tan et al., "Corrosion and wear-corrosion behavior of NiTi modified by plasma source ion implantation," Biomaterials, vol. 24, pp. 3931-3939, (2003).
Tanaka et al., "Micrometer-scale fabrication and assembly using focused ion beam," Thin Solid Films, vol. 509, pp. 113-117, (2006).
Tang et al., "Electrochemical Study of a Polarized Electrochemical Vapor Deposition Process," Journal of the Electrochemical Society, vol. 147, No. 9, pp. 3338-3344, (2000).
Tang et al., "Fabrication of Macroporous Alumina with Tailored Porosity," Jornal of American Ceramic Society, vol. 86, No. 12, pp. 2050-2054, (2003).
Tang et al., "Preparation of Porous anatase titania film," Materials Letters, vol. 58, pp. 1857-1860, (2004).
Tapphorn et al., "The Solid-State Spray Forming of Low-Oxide Titanium Components," Journal of Metals, vol. 50, No. 9, pp. 45-46,76, (1998).
Tassin et al., "Improvement of the Wear Resistance of 316 L Stainless Steel by Laser Surface Alloying," Surface and Coatings Technology, vol. 80, No. 9, pp. 207-210, (1996).
Terlingen, "Functionalization of Polymer Surfaces," Europlasma Technical Paper, pp. 1-29, May 8, 2004.
Terumo Europe, "Terumo Europe N.V. Enrols First Patient in Clinical Trial of the Nobori Drug-Eluting Coronary Stent," Press Release, 1 page, May 26, 2005, (http://www.terumo-europe.com/_press_release/may_26_2005.html.).
Thierry et al., "Bioactive Coatings of Endovascular Stents Based on Polyelectrolyte Multilayers," Biomacromolecules, vol. 4, pp. 1564-1571, (2003).
Thompson et al., "Tuning compliance of nanoscale polyelectrolyte multilayers to modulate cell adhesion," Biomaterials, vol. 26, pp. 6836-6845, (2005).
Tierno et al., "Using Electroless Deposition for the Preparation of Micron Sized Polymer/Metal Core/Shell Particles and Hollow Metal Spheres," Journal of Physics Chemistry B, vol. 110, pp. 3043-3050, (2006).
Tollon, "Fabrication of coated biodegradable polymer scaffolds and their effects on murin embryonic stem cells," Thesis presented to the University of Florida, pp. 1-7, (2005).
Tonosaki et al., "Nano-indentation testing for plasma-based ion-implanted surface of plastics," Surface and Coatings Technology, vol. 136, pp. 249-251, (2001).
Tones-Costa et al., "RBS Characterization of Porous Silicon Multilayer Interference Filters," Electrochemical and Solid-State Letters, vol. 7, No. 11, pp. G244-G249 (2004).
Toth et al., "Ar+ laser-induced forward transfer (LIFT): a novel method for micrometer-size surface patterning," Applied Surface Science, vol. 69, pp. 317-320, (1993).
Tsyganov et al., "Blood compatibilty of titanium-bases coatings prepared by metal plasma immersion ion implantation and deposition," Applied Surface Science, vol. 235, pp. 156-163, (2004).
Tsyganov et al., "Structure and Properties of Titanium Oxide Layers prepared by Metal Plasma Immersion Ion Implantation and Deposition," Surface & Coatings Technology, vol. 174-175, pp. 591-596, (2003).
Tsyganov et al., "Correlation between blood compatibility and physical surface properties of titanium-based coatings," Surface & Coatings Technology, vol. 200, pp. 1041-1044, (2005).
Uchida et al., "Apatite-forming ability of a zirconia/alumina nanocomposite induced by chemical treatment," Journal of Biomedical Materials Research, vol. 60, No. 2, pp. 277-282, May 2002.
University of Wisconsin, "Effect of Nano-Scale Textured Biomimetic Surfaces on Proliferation and Adhesion of Corneal Epithelial Cells," Materials Research Science and Engineering Center, pp. 1-2, (1997), (http://mrsec.wisc.edu/Past_proiects/seedproi4/Seedproi4.html).
Uyama et al., "Surface Modifications of Polymers by Grafting," Advances in Polymer Science, vol. 139, pp. 1-39, (1998).
Valsesia et al., "Selective immobilization of protein clusters on polymeric nanocraters," Advanced Functional Materials, vol. 16, pp. 1242-1246, (2006).
Valsesia, A. et al., "Fabrication of nanostructured polymeric surfaces for biosensing devices," Nanoletters, vol. 4, No. 6, pp. 1047-1050, (2004).
Van Alsten, "Self-Assembled Monolayers on Engineering Metals: Structure, Derivatization, and Utility," Langmuir, vol. 15, pp. 7605-7614, (1999).
Van Den Berg, "Nano particles play with electrons," pp. 1-9, [first downloaded on Nov. 12, 2003], (http://www.delftoutlook.tudelft.nl/info/index21fd.html?hoofdstuk=Article&ArtID=2243).
van der Eijk et al., "Metal Printing Process Development of a New Rapid Manufacturing Process for Metal Parts," Proceedings of the World PM2004 Conference held in Vienna, pp. 1-5, Oct. 17-21, 2004.
Van Steenkiste et al., "Kinetic spray coatings," Surface & Coatings Technology, vol. 111, pp. 62-71, (1999).
Vayssieres, "On the design of advanced metal oxide nanomaterials," International Journal of Nanotechnology, vol. 1, Nos. 1/2, pp. 1-41, (2004).
Velev et al., "Colloidal crystals as templates for porous materials," Current Opinion in Colloid & Interface Science, vol. 5, pp. 56-63, (2000).
Velev et al., "Porous silica via colloidal crystallization," Nature, vol. 389, pp. 447-448, Oct. 2, 1997.
Verheye et al., "Reduced Thrombus Formation by Hyaluronic Acid Coating of Endovascular Devices," Arteriosclerosis, Thrombosis, and Vascular Biology: Journal of the American Heart Association, vol. 20, pp. 1168-1172, (2000).
Vidal et al., "Electropolymerization of pyrrole and immobilization of glucose oxidase in a flow system: influence of the operating conditions on analytical performance," Biosensors & Bioelectronics, vol. 13, No. 3-4, pp. 371-382, (1998).
Vigil et al., "TiO2 Layers Grown from Flowing Precursor Solutions Using Microwave Heating," Langmuir, vol. 17, pp. 891-896, (2001).
Viitala et al., "Surface properties of in vitro bioactive and non-bioactive sol-gel derived materials," Biomaterials, vol. 23, pp. 3073-3086, (2002).
Vitte et al., "Is there a predictable relationship between surface physical-chemical properties and cell behaviour at the interface?" European Cells and Materials, vol. 7, pp. 52-63, (2004).
Volkel et al., "Electrodeposition of coppeer and cobalt nanostructures using self-assembled monolayer templates," Surface Science, vol. 597, pp. 32-41, (2005).
Vu et al., "Eletrophoretic deposition of nanocomposites formed from polythiophene and metal oxides," Electrochimica Acta, vol. 51, pp. 1117-1124, (2005).
Vuković et al., "Anodic stability and electrochromism of electrodeposited ruthenium—iridium coatings on titanium," Journal of Electroanalytical Chemisty, vol. 330, pp. 663-673 (1992).
Walboomers et al., "Effect of microtextured surfaces on the performance of percutaneous devices," Journal of Biomedical Materials Research Part A, vol. 74A, No. 3, pp. 381-387, (2005).
Wang et al., "Deposition of in-plane textured MgO on amorphous Si3N4 substrates by ion-beam-assisted deposition and comparisons with ion-beam-assistend deposidted yttria-stabilized-zirconia," Applied Physics Letters, vol. 71, No. 17, Issue 20, pp. 2955-2957, Nov. 17, 1997.
Wang et al., "Effect of substrate temperature on structure and electrical resistivity of laser ablated IrO2 thin films," Applied Surface Science, vol. 253, pp. 2911-2914, (2006).
Wang et al., "Effect of the discharge pulsating on microarc oxidation coating formed on Ti6A14V alloy," Materials Chemistry and Physics, vol. 90, pp. 128-133, (2005).

(56) References Cited

OTHER PUBLICATIONS

Wang et al., "Novel Poly(3-nonylthiophene)-TiO2 Hybrid Materials for Photovoltaic Cells," Synthetic Metals, vol. 155, pp. 677-680, (2005).
Wang et al., "Polyelectrolyte-Coated Colloid Spheres as Templates for Sol-Gel Reactions," Chem. Mater., vol. 14, pp. 1909-1913, (2002).
Wang et al., "Pulsed laser deposition of organic thin films," This Solid Films, vol. 363, pp. 58-60, (2000).
Wang et al., "Synthesis of Macroporous Titania and Inorganic Composite Materials from Coated Colloidal Spheres—A Novel Route to Tune Pore Morphology," Chem. Mater., vol. 13, pp. 364-371, (2001).
Webster et al."Enhanced functions of osteoblasts on nanophase ceramics," Biomaterials, vol. 21, No. 17, pp. 1803-1810, Sep. 2000.
Webster et al., "Increased osteoblast adhesion on nanophase metals: Ti, Ti6A14V, and CoCrMo," Biomaterials, vol. 25, No. 19, pp. 4731-4739, (2004).
Webster et al., "Specific proteins mediate enhanced osteoblast adhesion on nanophase ceramics," Journal of Biomedical Materials Research, vol. 5, No. 51, pp. 475-483, Sep. 2000.
Wei et al., "Structural Characterisation of Doped and Undoped Nanocrystalline Zinc Oxides Deposited by Ultrasonic Spray Assisted Chemical Vapour Deposition," Journal of Physics: Conference Series, vol. 26, pp. 183-186 (2006).
Wells, "Patterned Plasma Immersion Exposure of Insulating Materials for the Purpose of Modifying Optical Properties," thesis submitted to the college of William and Mary, Williamsburg, Vriginia, pp. 1-59, Apr. 2000.
Wesolowski et al., "Surface Charge and Ion Adsorption on Metal Oxides to 290° C.," Division of Chemical Sciences, Geosciences, and Biosciences, Office of Basic Energy Sciences, U.S. Department of Energy, pp. 1-6, (2001).
Wessling et al., "RF-sputtering of iridium oxide to be used as stimulation material in functional medical implants," Journal of Micromechanics and Microengineering, vol. 16, pp. S142-S148 (2006).
Whelan, "Targeted Taxane Therapy for Cancer," Drug Discovery Today, vol. 7, No. 2, pp. 90-92, Jan. 2002.
Which stent is right for you? pp. 1-3, (circa 2004).
Wieneke et al., "Synergistic Effects of a Novel Nanoporous Stent Coating and Tacrolimus on Intima Proliferation in Rabbits," Catheterization and Cardiovascular Interventions, vol. 60, pp. 399-407, (2003).
Wilkinson et al., "Nanofabrication in cellular engineering," Journal of Vacuum Science & Technology B, vol. 16, No. 6, pp. 3132-3136, (1998).
Wilkinson et al., "The use of materials patterned on a nano- and micro-metric scale in cellular engineering," Materials Science & Engineering C, vol. 19, No. 1-2, pp. 263-269, (2002).
Wilson et al., "Mediation of biomaterial-cell interactions by adsorbed proteins: A review," Tissue Engineering, vol. 11, No. 1-2, pp. 1-18, (2005).
Wong et al., "Balance of chemistry, topography, and mechanics at the cell-biomaterial interface: Issues and challenges for assessing the role of substrate mechanics on cell response," Surface Science, vol. 570, No. 1-2, pp. 119-133, (2004).
Wong et al., "Polymer segmental alignment in polarized pulsed laser-induced periodic surface structures," Applied Physics A, vol. 65, pp. 519-523, (1997).
Wood, "Next-generation drug-eluting stents tackle shortcomings of Cypher, Taxus," Heart Wire, pp. 1-6, Feb. 7, 2006, (http://www.theheart.org/article/641591.do.).
World Reference definition, "Interconnected," WorldReference.com, 1 page, [downloaded Jan. 21, 2010].
Wu et al., "Characterization of Mesoporous Nanocrystalline TiO2 Photocatalysts Synthesized Via a Sol-Solvothermal Process at a Low Temperature," Journal of Solid State Chemistry, vol. 178, pp. 321-328, (2005).
Wu et al., "Chitosan-Mediated and Spatially Selective Electrodeposition of Nanoscale Particles," Langmuir, vol. 21, pp. 3641-3646, (2005).
Wu et al., "Corrosion resistance of BaTiO3 films prepared by plasma electrolytic oxidation," Surface and Coatings Technology, vol. 166, pp. 31-36, (2002).
Wu et al., "Design of Doped Hybrid Xerogels for a Controlled Release of Brilliant Blue FCF," Journal of Non-Crystalline Solids, vol. 342, pp. 46-53, (2004).
Wu et al., "The effects of cathodic and anodic voltages on the characteristics of purous nanocrystalline titania coatings fabricated by microarc oxidation," Materials Letters, vol. 59, pp. 370-375, (2005).
Xia et al., "Monodispersed Colloidal Spheres: Old Materials with New Applications," Advanced Materials, vol. 12, No. 10, pp. 693-713, (2000).
Xu et al., "An Improved Method to Strip Aluminum from Porous Anodic Alumina Films," Langmuir, vol. 19, pp. 1443-1445, (2003).
Xu et al., "Cold spay deposition of thermoplastic powder," Surface & Coatings Technology, vol. 2001, pp. 3044-3050, (2006).
Xu et al., "Synthesis of porosity controlled ceramic membranes," Journal of Material Research, vol. 6, No. 5, pp. 1073-1081, May 1991.
Yamato et al. "Nanofabrication for micropatterned cell arrays by combining electron beam-irradiated polymer grafting and localized laser ablation," Journal of Biomedical Materials Research, vol. 67, No. 4, pp. 1065-1071, Dec. 15, 2003.
Yan et al., "New MOCVD precursor for iridium thin films deposition," Materials Letters, vol. 61, pp. 216-218, (2007).
Yan et al., "Sol-gel Processing," Handbook of Nanophase and Nanostructured Materials, vol. 1: Synthesis, Chapter 4, pp. 1-27, (2003).
Yang et al., "Laser spray cladding of porous NiTi coatings on NiTi substrates," The Hong Kong Polytechnic University, 1 page, Dec. 28, 2006.
Yang et al., "Poly(L,L-lactide-co-glycolide)/tricalcium phosphate composite scaffold and its various changes during degradation in vitro," Polymer Degradation and Stability, vol. 91 pp. 3065-3073, (2006).
Yang et al., "Thermal oxidation products and kinetics of polyethylene composites," Polymer Degradation and Stability, vol. 91, pp. 1651-1657, (2006).
Yang et al., "Solution phase synthesis of magnesium hydroxide sulfate hydrate nanoribbons", Nanotechology, vol. 15, pp. 1625-1627, (2004).
Yankov et al., "Reactive plasma immersion ion implantation for surface passivation," Surface and Coatings Technology, vol. 201, pp. 6752-6758, (2007).
Yap et al., "Protein and cell micropatterning and its integration with micro/nanoparticles assembley," Biosensors and Bioelectronics, vol. 22, pp. 775-788, (2007).
Yerokhin et al., "Kinetic aspects of aluminium titanate layer formation on titanium alloys by plasma electrolytic oxidation," Applied Surface Science, vol. 200, pp. 172-184, (2002).
Yerokhin et al., "Plasma electrolysis for surface engineering," Surface Coatings Technology, vol. 122, pp. 73-93, (1999).
Yim et al., "Nanopattern-induced changes in morphology and motility of smooth muscle cells," Biomaterials, vol. 26, pp. 5405-5413, (2005).
Yim et al., "Significance of synthetic nanostructures in dictating cellular response," Nanomedicine: Nanotechnology, Biology and Medicine, vol. 1, No. 1, pp. 10-21, Mar. 1, 2005.
Yoldi et al., "Electrophoretic deposition of colloidal crystals assisted by hydrodynamic flows," Journal of Materials Science, vol. 41, pp. 2964-2969, (2006).
Yoshida et al., "Impact of Low Energy Helium Irradiation on Plasma Facing Metals," Journal of Nuclear Materials, vol. 337-339, pp. 946-950, (2005).
Young et al., "Polarized electrochemical vapor deposition for cermet anodes in solid oxide fuel cells," Solid State Ionics, vol. 135, pp. 457-462, (2000).
Yu et al., "Encapsulated cells: an atomic force microscopy study," Biomaterials, vol. 25, pp. 3655-3662, (2004).

(56) References Cited

OTHER PUBLICATIONS

Yu et al., "Enhanced photocatalytic activity of mesoporous and ordinary TiO2 thin films by sulfuric acid treatment," Applied Catalysis B: Environmental, vol. 36, pp. 31-43, (2002).

Yu et al., "Enhanced photoinduced super-hydrophilicity of the sol-gel-derived TiO2 thin films by Fe-doping," Materials Chemistry and Physics, vol. 95, pp. 193-196, (2006).

Yu et al., "Light-induced super-hydrophilicity and photocatalytic activity of mesoporous TiO2 thin films," Journal of Photochemistry and Photobiology A: Chemistry, vol. 148, pp. 331-339, (2002).

Yun et at., "Low-Temperature Coating of Sol-Gel Anatase Thin Films," Materials Letters, vol. 58, pp. 3703-3706, (2004).

Zakharian et al., "A Fullerene-Paclitaxel Chemotherapeutic: Synthesis, Characterization, and Study of Biological Activity in Tissue Culture," Journal of American Chemistry Society, vol. 127, pp. 12508-12509, (2005).

Zbroniec et al., "Laser ablation of iron oxide in various ambient gases," Applied Surface Science, vol. 197-198, pp. 883-886, (2002).

Zeng et al., "Biodegradable electrospun fibers for drug delivery," Journal of Controlled Release, vol. 92, pp. 227-231, (2003).

Zhang et al., "Surface analyses of micro-arc oxidized and hydrothermally treated titanium and effect on osteoblast behavior," Journal of Biomedical Materials Research, vol. 68A, pp. 383-391, (2004).

Zhang et al., "Surface treatment of magnesium hydroxide to improve its dispersion in organic phase by the ultrasonic technique", Applied Surface Science, vol. 253, pp. 7393-7397, (2007).

Zhao et al., "Coating deposition by the kinetic spray process," Surface & Coatings Technology, vol. 200, pp. 4746-4754, (2006).

Zhao et al., "Designing Nanostructions by Glancing Angle Deposition," Proceedings of SPIE, vol. 5219: Nanotubes and Nanowires, pp. 59-73, (2003).

Zhao et al., "Formulation of a ceramic ink for a wide-array drop-on-demand ink jet printer," Ceramics International, vol. 29, pp. 887-892, (2003).

Zheng et al., "Substrate temperature dependent morphology and resistivity of pulsed laser deposited iridium oxide thin films," Thin Solid Films, vol. 496, pp. 371-375, (2006).

Zheng et al., "Synthesis of Mesoporous Silica Materials via Nonsurfactant Templated Sol-Gel Route Using Mixture of Organic Compounds as Template," Journal of Sol-Gel Science and Technology, vol. 24. pages 81-88, (2002).

Zhitomirsky et al., "Cathodic electrodeposition of MnOx films for electrochemical supercapacitors," Electrochimica Acta, vol. 51, pp. 3039-3045, (2006).

Zhitomirsky et al., "Electrodeposition of composite hydroxyapatite-chitosan films," Materials Chemistry and Physics, vol. 94, pp. 245-251, (2005).

Zhou et al., "Branched Ta nanocolumns grown by glancing angle deposition," Applied Physics Letters, vol. 88, p. 203117, (2006).

Zoppi et al., "Hybrid Films of Poly(ethylene oxide-b-amide 6) Containing Sol-Gel Silicon or Titanium Oxide as Inorganic Fillers: Effect of Morphology and Mechanical Properties on Gas Permeability," Polymer, vol. 41, pp. 5461-5470, (2000).

Zou et al., "Highly textural lamellar mesostructured magnesium hydroxide via a cathodic electrodeposition process", Materials Letters, vol. 61, pp. 1990-1993, (2007).

\* cited by examiner

MEDICAL DEVICES HAVING A COATING OF INORGANIC MATERIAL

CROSS REFERENCE TO RELATED APPLICATION

The present application claims priority to U.S. provisional application Ser. No. 61/047,002 filed Apr. 22, 2008, the disclosure of which is incorporated herein by reference in its entirety.

TECHNICAL FIELD

The present invention relates to medical devices, and in particular, medical devices having a coating containing a therapeutic agent.

BACKGROUND

Many implantable medical devices are coated with drugs that are eluted from the medical device upon implantation. For example, some vascular stents are coated with a drug which is eluted from the stent for treatment of the vessel and/or to prevent some of the unwanted effects and complications of implanting the stent. In such drug-eluting medical devices, various methods have been proposed to provide a mechanism for drug elution. However, there is a continuing desire for improved devices and methods for providing drug elution from medical devices.

SUMMARY

In one aspect, the present invention provides a medical device having a first configuration (e.g., unexpanded) and a second configuration (e.g., expanded), wherein the medical device comprises: (a) a reservoir containing a therapeutic agent; and (b) a barrier layer disposed over the reservoir, wherein the barrier layer comprises an inorganic material, wherein the barrier layer has a first permeability to the therapeutic agent when the medical device is in the first configuration and a second permeability to the therapeutic agent when the medical device is in the second configuration, and wherein the second permeability is greater than the first permeability.

In another aspect, the present invention provides a medical device comprising: (a) a reservoir containing a therapeutic agent; (b) a barrier layer disposed over the reservoir, wherein the barrier layer comprises an inorganic material; and (c) a swellable material disposed between the barrier layer and a surface of the medical device, wherein the swellable material is a material that swells upon exposure to an aqueous environment.

In yet another aspect, the present invention provides a medical device having a multi-layered coating, wherein the multi-layered coating comprises: (a) a first reservoir layer over a surface of the medical device, wherein the first reservoir layer comprises a first therapeutic agent; (b) a first barrier layer over the first reservoir layer, wherein the first barrier layer comprises a first inorganic material; (c) a second reservoir layer over the first barrier layer, wherein the second reservoir layer comprises a second therapeutic agent; (d) a second barrier layer over the second reservoir layer, wherein the second barrier layer comprises a second inorganic material; and (e) a plurality of excavated regions penetrating through at least a partial thickness of the multi-layered coating.

In yet another aspect, the present invention provides a medical device comprising: (a) a polymer layer comprising a block co-polymer, wherein the polymer layer contains a therapeutic agent; and (b) a barrier layer disposed over the polymer layer, wherein the barrier layer comprises an inorganic material, and wherein the barrier layer has a plurality of discontinuities.

The present invention also provides methods for forming a coating on medical devices and methods for delivering a therapeutic agent to a body site.

BRIEF DESCRIPTION OF THE DRAWINGS

FIG. 1A shows a top view of a strut on the stent. FIG. 1B shows a cross-section perspective view of a portion of the stent strut in FIG. 1A. FIG. 1C shows a cross-section side view of the stent strut in FIG. 1B, before the stent is expanded. FIG. 1D shows a cross-section side view of the stent strut in FIG. 1B, after the stent is expanded.

FIG. 2A shows the stent strut before the stent is expanded. FIG. 2B shows the stent strut after the stent is expanded. FIG. 2C shows the stent strut after degradation of the plugs.

FIG. 3A shows the stent strut before the stent is expanded. FIG. 3B shows the stent strut after the stent is expanded.

FIG. 4A shows the stent strut before the stent is expanded. FIG. 4B shows the stent strut after the stent is expanded.

FIG. 5A shows the stent strut before the stent is expanded. FIG. 5B shows the stent strut after the stent is expanded.

FIG. 6A shows the stent strut before the stent is expanded. FIG. 6B shows the stent strut after the stent is expanded.

FIG. 7A shows the stent strut before the water-swellable layer is hydrated. FIG. 7B shows the stent strut after the water-swellable layer is hydrated.

FIG. 8A shows the stent strut before the hydrogel capsules are hydrated. FIG. 8B shows the stent strut after the hydrogel capsules are hydrated.

FIG. 14A shows the stent strut before dissolution of the polymer layer. FIG. 14B shows the stent strut after dissolution of the polymer layer.

DETAILED DESCRIPTION

Figure 1A:
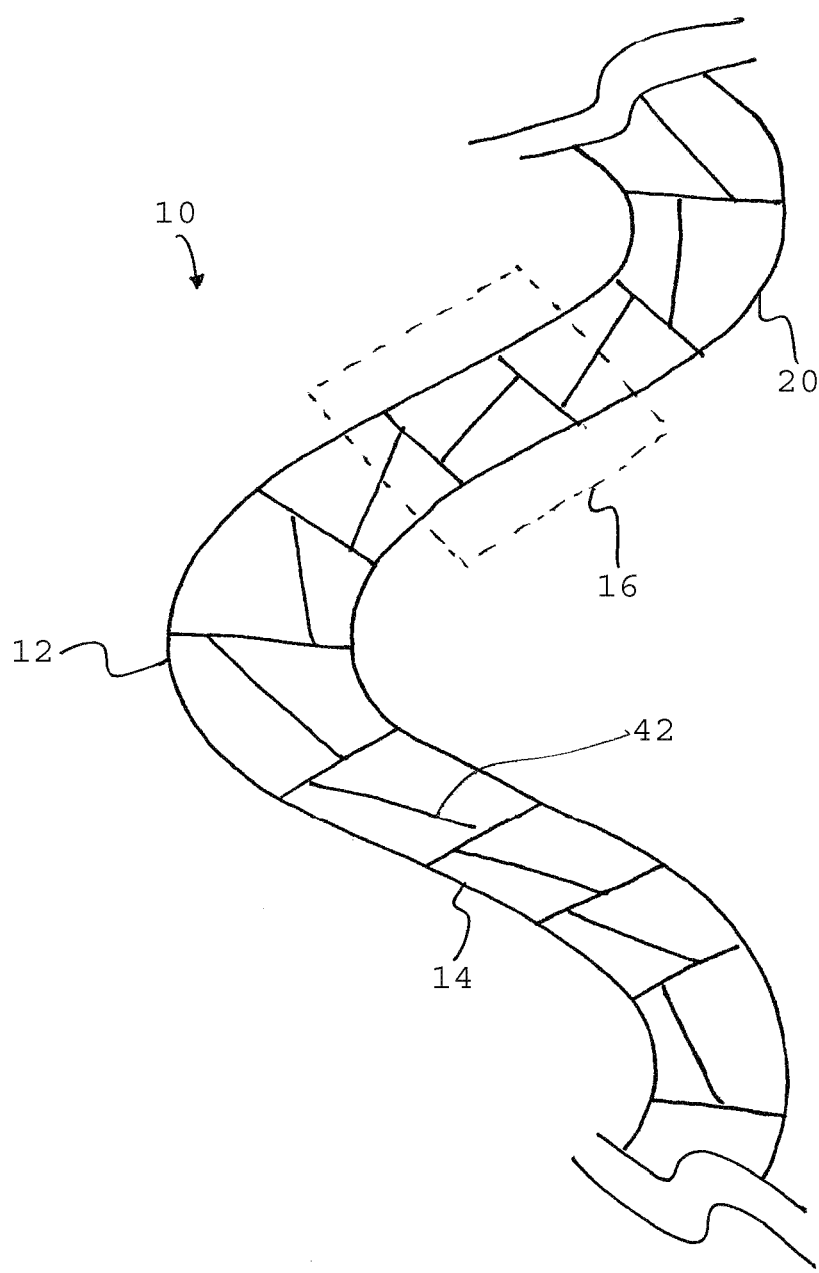
FIGS. 1A-1D show various views of a stent according to an embodiment of the present invention.

In one aspect, the present invention provides a medical device having a first configuration and a second configuration. The medical device comprises a reservoir containing a therapeutic agent. A barrier layer is disposed over the reservoir, wherein the barrier layer comprises an inorganic material.

Medical devices may have various types of first and second configurations. In some cases, the medical device is an expandable medical device having an unexpanded (first) configuration and an expanded (second) configuration. For example, the medical device may be an expandable stent or vascular graft which is delivered to the target body site in an unexpanded configuration and then expanded to the expanded configuration for implantation at the target site. Various other types of first/second configurations are also possible, including for example, unbent/bent configurations, unstretched/stretched configurations, or undeformed/deformed configurations.

The reservoir containing the therapeutic agent may be provided in various ways. The reservoir may be the therapeutic agent formulation alone, or may comprise any structure that retains or holds the therapeutic agent. For example, the reservoir may be a polymer layer or other layer over the medical device with the therapeutic agent disposed therein. In another example, the reservoir may be created in the surface of the medical device (e.g., a porous surface), or the medical device may have pits, pores, cavities, or holes that contain the therapeutic agent.

The barrier layer comprises an inorganic material, which may be selected on the basis of various considerations depending upon the particular application. For example, the inorganic material may be selected for its biologic properties (e.g., biocompatibility), structural properties (e.g., porosity), chemical properties (e.g., chemical reactivity), handling properties (e.g., storage stability), or the deposition techniques that can be used. Suitable inorganic materials for use in the barrier layer include inorganic elements, such as pure metals including aluminum, chromium, gold, hafnium, iridium, niobium, palladium, platinum, tantalum, titanium, tungsten, zirconium, and alloys of these metals (e.g., nitinol); and inorganic compounds, such as metal oxides (e.g., iridium oxide or titanium oxide), metal nitrides, and metal carbides, as well as inorganic silicides. Other suitable inorganic materials include certain carbon-containing materials that are traditionally considered inorganic materials, such as carbonized materials, carbon nanostructure materials, (e.g., carbon nanotubes, fullerenes, etc.), and diamond-like materials.

By being comprised of an inorganic material, the barrier layer may be useful in improving the biocompatibility or therapeutic effectiveness of the medical device. For example, the barrier layer may be useful in protecting body tissue from direct exposure to an underlying polymer layer that is less biocompatible than the barrier layer. Also, the barrier layer may present a more attractive surface for body tissue. For example, in the case of a vascular stent, the barrier layer may present a surface that promotes the migration and growth of endothelial cells, which can help to reduce the incidence of adverse effects related to stent implantation.

In some cases, the barrier layer may be formed using any of various layer deposition processes. For example, layer deposition processes that may be suitable for forming the barrier layer include: chemical vapor deposition, plasma vapor deposition, sputtering, pulsed laser deposition, sol-gel, evaporation (thermal, electron beam, etc.), molecular beam epitaxy, solution process (e.g., spray coating, dip coating, roll coating, etc.), or electrodeposition (e.g., electroplating, electrospray, etc.). The barrier layer may also be formed by carbonization (e.g., by laser heating or ion bombardment) of a precursor carbon material (e.g., a polymer) to form a barrier layer formed of an inorganic carbonized material.

The process used to form the barrier layer can be selected on the basis of various considerations, such as the type of medical device, the vulnerability of the therapeutic agent to heat degradation, or the type of inorganic material being used in the barrier layer. The thickness of the barrier layer will vary, depending upon the particular application. In some cases, the thickness of the barrier layer is in the range of 20 nm to 10 μm, but other thicknesses are also possible.

The barrier layer has a first permeability to the therapeutic agent when the medical device is in the first configuration and a second permeability to the therapeutic agent when the medical device is in the second configuration, with the second permeability being greater than the first permeability. Various possible degrees of permeability are possible for the first and second permeabilities of the barrier layer. In some cases, the first permeability does not provide a therapeutically effective release profile of the therapeutic agent (e.g., negligible or zero permeability), whereas the second permeability does provide a therapeutically effective release profile of the therapeutic agent. In some cases, the second permeability is at least 1.5-fold greater; and in some cases, at least 3.0-fold greater than the first permeability (where the first permeability is non-zero).

The second permeability is provided by discontinuities that are formed in the barrier layer when the medical device changes from the first configuration (e.g., unexpanded) to the second configuration (e.g., expanded). As used herein, the term "discontinuities" refers to discrete defects in the barrier layer that allow the passage of therapeutic agents through the barrier layer. Examples of such discrete defects include fractures lines, cracks, breaks, gaps, faults, holes, perforations, and other openings through the full thickness of the barrier layer. These discontinuities may have various dimensions and geometries, which can affect the permeability of the barrier layer. For example, wider discontinuities can increase the permeability of the barrier layer, and thus, increase the rate at which the therapeutic agent diffuses through the barrier layer. The discontinuities may be linear or curved, jagged or smooth, irregular or regular, or have any of various other patterns.

In addition to providing the second permeability, the discontinuities may also serve to relieve any stress on the adhesive bond between the barrier layer and the underlying substrate when the medical device undergoes deformation. By allowing the formation of discontinuities in the barrier layer, the barrier layer is made less sensitive to strain, thus relieving stress on the adhesive bond when the medical device undergoes deformation.

In certain embodiments, the medical device is provided in the first configuration (e.g., unexpanded) with the barrier layer having a plurality of regions of structural weakness. As used herein, "regions of structural weakness" refers to regions of relative weakness in the barrier layer such that when the barrier layer is strained, discontinuities will form and/or propagate in the regions of structural weakness. In certain embodiments, the regions of structural weakness are excavated regions in the barrier layer. As used herein, "excavated regions" refers to voids (e.g., holes, slots, grooves, channels, etchings, scribe lines, perforations, pits, etc.) that are created by removal of material using techniques that control the size, shape, and location of the voids. For example, such techniques include direct-write etching using energetic beams (e.g., laser, ion, or electron), micromachining, microdrilling, or lithographic processes.

The excavated regions may have various geometries and dimensions, which may be adjusted to achieve the desired amount of weakness in that particular region of the barrier layer. The excavated regions may extend partially or completely through the barrier layer. Increasing the depth of penetration of the excavated regions can increase the amount of weakness in that particular region of the barrier layer. In some cases, the excavated regions have an average penetration depth of 10%-90% through the thickness of the layer, but other average penetration depths are also possible. In some cases, the average penetration depth of the excavated regions is greater than 10% of the thickness of the barrier layer; and in some cases, greater than 33%; and in some cases, greater than 50%. Increasing the width of the excavated regions can also increase the amount of weakness in the barrier layer in that particular region. In some cases, the excavated regions have an average width in the range of 10 nm to 1 µm, but other average widths are also possible. The overall ratio between the surface area of the excavated regions and the non-excavated regions will vary depending upon the particular application. In some cases, the excavated regions may constitute 5-90%; and in some cases, 30-70% of the overall surface area, but other ratios are also possible Also, the surface area ratio of the excavated regions to the non-excavated regions may be different at different portions of the medical device.

Figure 1B:
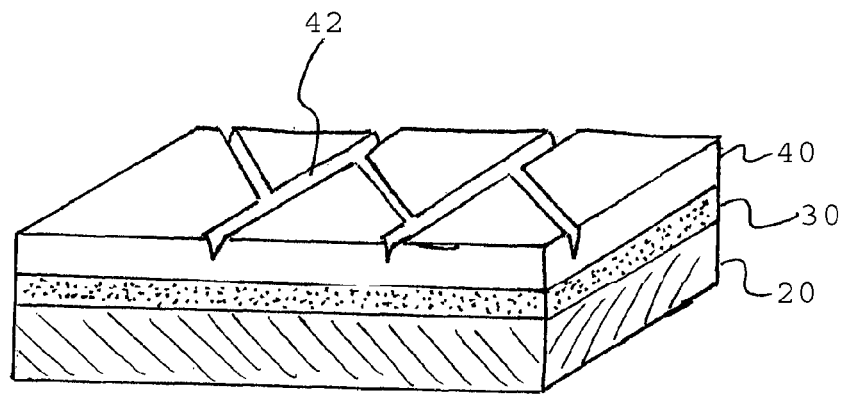
Figure 1C:
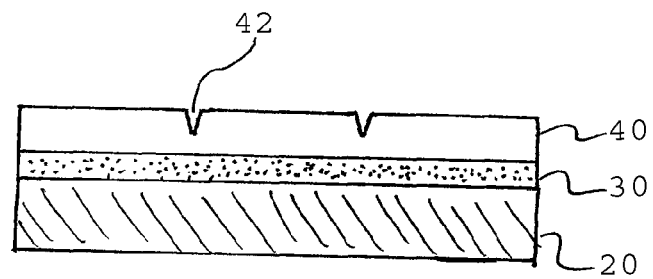

For example, referring to the embodiment shown in FIGS. 1A-1D, a strut 20 of an expandable stent 10 is coated with a polymer layer 30 containing a therapeutic agent. Polymer layer 30 is coated with a barrier layer 40 formed of iridium oxide. Referring to FIG. 1A, showing a top view of a portion of stent strut 20, barrier layer 40 over stent strut 20 has multiple scribe lines 42 that are formed by laser etching. FIG. 1B is a cross-section perspective view and FIG. 1C is a cross-section side view of portion 16 in FIG. 1A, showing barrier layer 40, polymer layer 30, and stent strut 20 when stent 10 is in an unexpanded configuration. In this particular embodiment, scribe lines 42 penetrate partially through barrier layer 40.

Figure 1D:
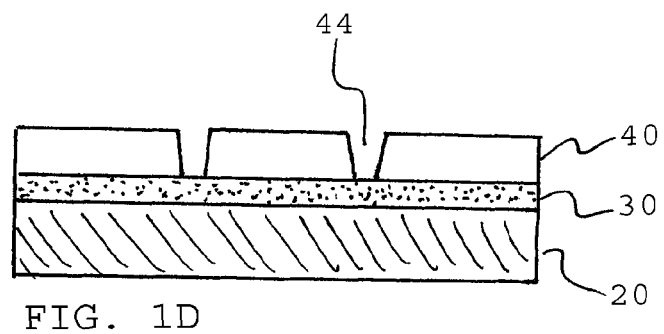

In operation, stent 10 is delivered to a body site in an unexpanded configuration. Once at the target body site, stent 10 is expanded. As shown in FIG. 1D, upon expansion, deformation of the stent struts imposes strain on barrier layer 40, causing the formation of cracks 44 in barrier layer 40 along scribe lines 42. These cracks 44 allow the passage of therapeutic agent from polymer layer 30 through barrier layer 40 to the external environment.

The laser used in the etching process may be any of various lasers capable of ablating inorganic material, including excimer lasers. Various parameters, including for example, the wavelength, pulse energy, and/or pulse frequency of the laser, may be adjusted to achieve the desired result. The laser can be applied using direct-write techniques or by using masking techniques (e.g., laser lithography). In some cases, a cold ablation technique is used (e.g., using a femtosecond laser or a short wavelength excimer laser), which may be useful in reducing any damage to the therapeutic agent or, where a polymeric material is used in the medical device, in reducing damage to the polymeric material.

Figure 2A:
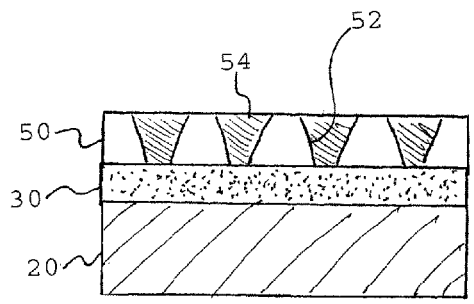
FIGS. 2A-2C show cross-section views of a strut on a stent according to another embodiment.

In certain embodiments, the excavated regions may extend through the full thickness of the barrier layer, with the excavated regions being filled with a biodegradable filler material. For example, referring to the embodiment shown in FIGS. 2A and 2B, a stent strut 20 of an expandable stent is coated with a polymer layer 30 containing a therapeutic agent. Polymer layer 30 is coated with a barrier layer 50, which has multiple perforations 52. Perforations 52 are filled with plugs 54, which comprises a biodegradable filler material, such as a biodegradable polymer, pharmaceutically acceptable salt or sugar, or a biodegradable metal (e.g., magnesium).

Figure 2B:
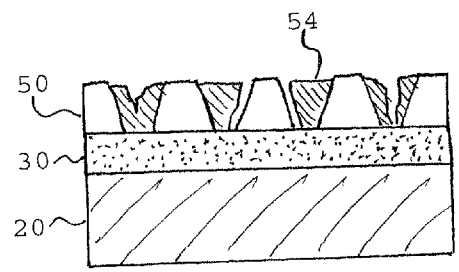
Figure 2C:
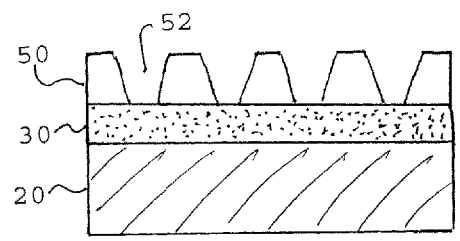

In operation, the stent is delivered to a body site in an unexpanded state. Once at the target body site, the stent is expanded. As shown in FIG. 2B, upon expansion, deformation of the stent struts imposes strain upon barrier layer 50. This causes plugs 54 to partially detach or fracture, increasing the exposure of plugs 54 to the physiologic fluid. As shown in FIG. 2C, plugs 54 then undergo biodegradation such that perforations 52 are made patent. This allows the passage of therapeutic agent from polymer layer 30 through perforations 52 to the external environment.

In certain embodiments, the regions of structural weakness are regions where the barrier layer has reduced thickness relative to the full thickness of the barrier layer. The regions of reduced thickness may be created in various ways during the formation of the barrier layer. In one example, the regions of reduced thickness may be created by disposing the barrier layer on a textured surface such that the barrier layer has reduced thickness in the regions that are located over the protruding features of the textured surface. The protruding features may be bumps, ridges, ribs, folds, corrugations, projections, prominences, elevations, or other features that protrude from the textured surface. The textured surface may form a pattern that is regular or irregular.

Figure 3A:
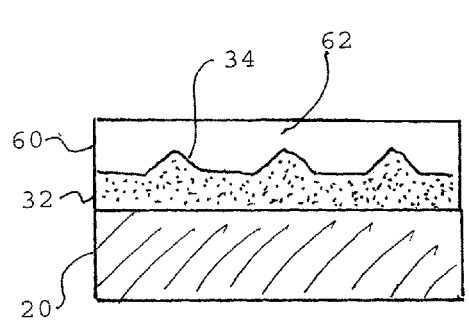
FIGS. 3A and 3B show cross-section views of a strut on a stent according to yet another embodiment.
Figure 3B:
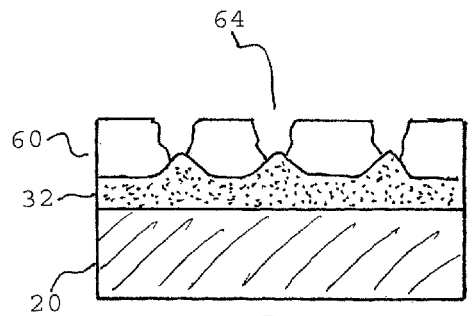

For example, referring to the embodiment shown in FIGS. 3A and 3B, a stent strut 20 of an expandable stent is coated with a polymer layer 32. The surface of polymer layer 32 has a plurality of ridges 34. Polymer layer 32 is coated with a barrier layer 60. The portions of barrier layer 60 overlying ridges 34 are thinner portions 62 that have reduced thickness compared to the full thickness barrier layer 60.

In operation, the expandable stent is delivered to a body site in an unexpanded state. Once at the target body site, the expandable stent is expanded. As shown in FIG. 3B, when the expandable stent is expanded, deformation of the stent struts imposes strain on barrier layer 60, causing the formation of cracks 64 in the thinner portions 62 of barrier layer 60. These cracks 64 allow the passage of therapeutic agent from polymer layer 30 through barrier layer 62 to the external environment.

The regions of structural weakness may be distributed in various ways on different portions of the medical device. In certain embodiments, the regions of structural weakness are distributed uniformly throughout the medical device. In certain embodiments, the regions of structural weakness in the barrier layer at one portion of the medical device has different characteristics than those at a different portion of the medical device. In some cases, the regions of structural weakness are arranged and/or constructed to accommodate the location-dependent variation in strain forces that the barrier layer will experience when the medical device is changed from the first configuration to the second configuration. For example, in the expandable stent 10 of FIG. 1A, different portions of stent strut 20 will undergo varying amounts of deformation when stent 10 is expanded. In this particular stent, portion 12 of stent strut 20 will undergo more deformation than portion 14, causing more strain in barrier layer 40 over portion 12 than over portion 14. As such, the regions of structural weakness can be made weaker in areas where barrier layer 40 undergoes less strain in order to achieve the desired amount of second permeability in those areas of barrier layer 40.

Figure 4A:
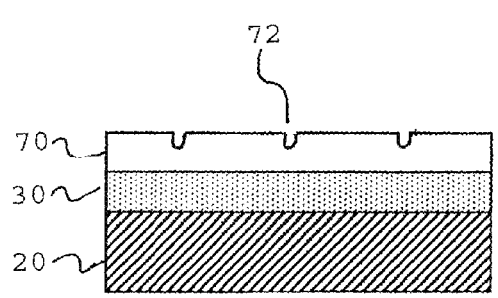
FIGS. 4A and 4B show cross-section views of a strut on a stent according to yet another embodiment.
Figure 4B:
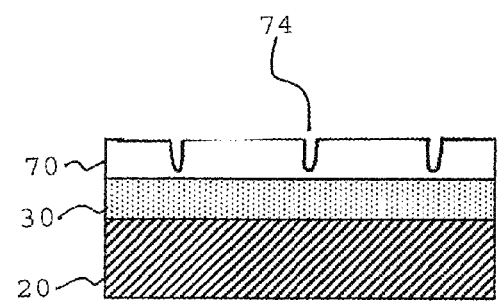
Figure 5A:
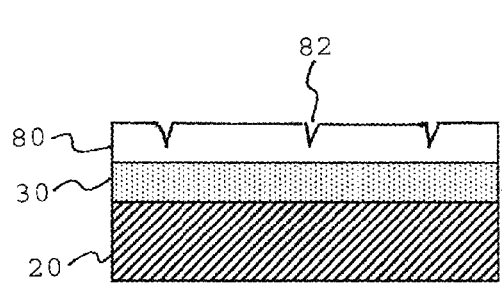
FIGS. 5A and 5B show cross-section views of a strut on a stent according to yet another embodiment.
Figure 5B:
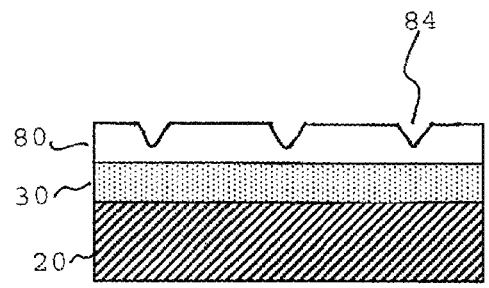
Figure 6A:
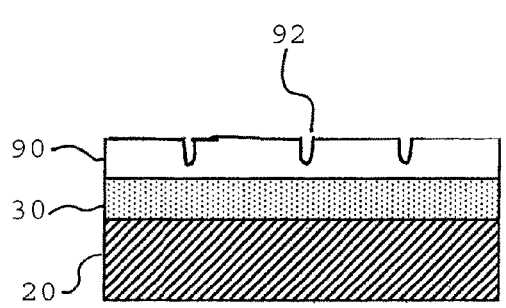
FIGS. 6A and 6B show cross-section views of a strut on a stent according to yet another embodiment.
Figure 6B:
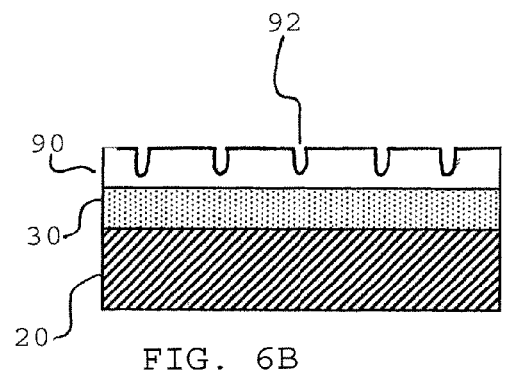

For example, referring to the embodiment shown in FIGS. 4A and 4B, a stent strut 20 of an expandable stent is coated with a polymer layer 30 containing a therapeutic agent. Polymer layer 30 is coated with a barrier layer 70. Referring to FIG. 4A, in portions of the stent where the stent struts experience greater deformation during expansion, barrier layer 70 has shallow scribe lines 72. Referring to FIG. 4B, in portions of the stent where the stent struts experience less deformation during expansion, barrier layer 70 has deep scribe lines 74. In another example, referring to the embodiment shown in FIGS. 5A and 5B, a stent strut 20 of an expandable stent is coated with a polymer layer 30 containing a therapeutic agent. Polymer layer 30 is coated with a barrier layer 80. The shape of the base of the scribe lines can also have an effect on crack propagation, with blunt or larger radius tips sustaining less stress concentration than sharp or smaller radius tips. Thus, referring to FIG. 5A, in portions of the stent where the stent struts experience less deformation during expansion, barrier layer 80 has narrow scribe lines 82. Referring to FIG. 5B, in portions of the stent where the stent struts experience greater deformation during expansion, barrier layer 80 has wide scribe lines 84. In yet another example, referring to the embodiment shown in FIGS. 6A and 6B, a stent strut 20 of an expandable stent is coated with a polymer layer 30 containing a therapeutic agent. Polymer layer 30 is coated with a barrier layer 90. Referring to FIG. 6A, in portions of the stent where the stent struts experience greater deformation during expansion, barrier layer 90 has a lower density of scribe lines 92. Referring to FIG. 6B, in portions of the stent where the stent struts experience less deformation during expansion, barrier layer 90 has a higher density of scribe lines 92.

In another aspect, the present invention provides a medical device having a reservoir containing a therapeutic agent. Further, a barrier layer is disposed over the reservoir, wherein the barrier layer comprises an inorganic material. Further, a swellable material is disposed between the barrier layer and a surface of the medical device, wherein the swellable material is a material which swells upon exposure to an aqueous environment. Such swellable materials include water-swellable polymers and oxidizable metals. The composition and structure of the reservoir, as well as the manner in which it may be formed, are as described above. The composition and structure of the barrier layer, as well as the manner in which it may be formed, are as described above.

The barrier layer has a first permeability to the therapeutic agent prior to swelling of the swellable material and a second permeability to the therapeutic agent after swelling of the swellable material, with the second permeability being greater than the first permeability. In certain embodiments, the barrier layer may have regions of structural weakness as described above. When the swellable material swells, it applies outward pressure against the barrier layer. The strain imposed by this pressure causes the formation of discontinuities in the barrier layer, which increases the permeability of the barrier layer. Thus, the second permeability of the barrier layer is provided by discontinuities that form in the barrier layer upon swelling of the swellable material. Where the barrier layer has a plurality of regions of structural weakness, the discontinuities may form in these regions.

In certain embodiments, the swellable material is a water-swellable polymer that swells when it becomes hydrated. In such cases, the medical device is designed such that the water-swellable polymer becomes hydrated when the medical device is exposed to an aqueous environment (e.g., body fluid or tissue). The aqueous fluid may be distributed to the water-swellable polymer through various pathways. In certain embodiments, aqueous fluid has access to the water-swellable polymer via a pathway that does not involve the barrier layer. For example, aqueous fluid may have access to the water-swellable polymer through another portion of the medical device, or aqeuous fluid may be actively supplied to the water-swellable polymer by the medical device.

In certain embodiments, aqueous fluid from the external environment accesses the water-swellable polymer by passing through the barrier layer, which is allowed by a first, initial permeability of the barrier layer. This first, initial permeability of the barrier layer may be provided in various ways. In some cases, the barrier layer may be porous or semi-permeable. In some cases, the barrier layer may have one or more initially present discontinuities that allow the penetration of aqueous fluid through the barrier layer. These initially present discontinuities may be formed in various ways. One such method involves heating and/or cooling the barrier layer, which would cause thermal expansion and/or contraction of the barrier layer and result in the formation of discontinuities. For example, the barrier layer may be cooled by dipping the medical device into a cold solvent mixture or a cryogenic liquid (e.g., liquid nitrogen). In another example, the barrier layer may be subjected to alternating cycles of heating and cooling (or vice versa).

Any of a number of various types of water-swellable polymers known in the art may be used, including those that form hydrogels. Other examples of water-swellable polymers include polyethylene oxide, hydroxypropyl methylcellulose, poly(hydroxyalkyl methacrylate), polyvinyl alcohol, and polyacrylic acid. The water-swellable polymer may be applied to the medical device in various ways. For example, the water-swellable polymer may be provided in the form of gels, layers, fibers, agglomerates, blocks, granules, particles, capsules, or spheres. In some cases, the water-swellable polymer is contained within or underneath a polymer layer containing the therapeutic agent. In such cases, the polymer layer may serve to control the rate at which the water-swellable polymer becomes hydrated.

Figure 7A:
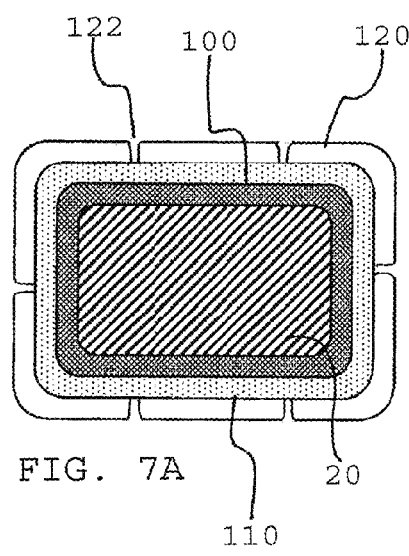
FIGS. 7A and 7B show cross-section views of a strut on a stent according to yet another embodiment.

The following non-limiting examples further illustrate various embodiments of this aspect of the present invention. In one example, referring to the embodiment shown in FIGS. 7A and 7B, a stent strut 20 of a stent is coated with a water-swellable layer 100 formed of a hydrogel. Water-swellable layer 100 is coated with a polymer layer 110 containing a therapeutic agent. Polymer layer 110 is coated with a barrier layer 120, which has multiple small pores 122 to allow the passage of fluids through barrier layer 120 so that water-swellable layer 100 can become hydrated when the stent is exposed to an aqueous environment. In alternate embodiments, the positions of water-swellable layer 100 and polymer layer 110 may be switched.

Figure 7B:
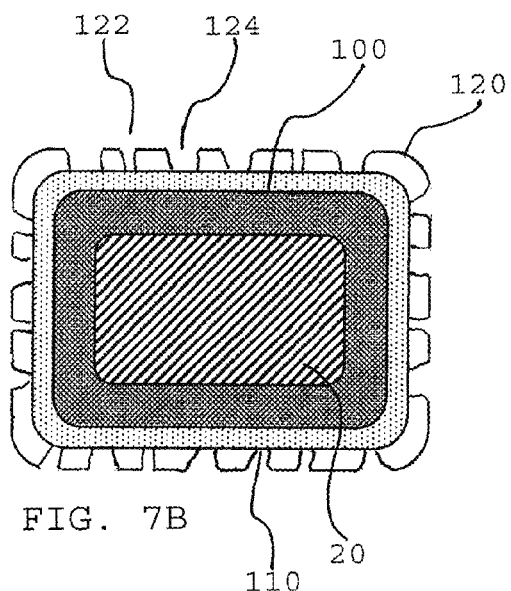

In operation, when the stent is delivered to a target body site, body fluid flows through pores 122 of barrier layer 120, diffuses through polymer layer 110, and hydrates the hydrogel in water-swellable layer 100. As shown in FIG. 7B, hydration of the hydrogel causes volume expansion of water-swellable layer 100, which causes the formation of cracks 124 in barrier layer 120. These cracks 124 allow the passage of therapeutic agent from polymer layer 110 through barrier layer 120 to the external environment.

Figure 8A:
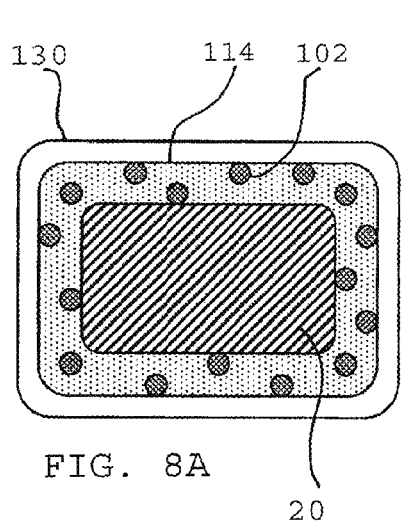
FIGS. 8A and 8B show cross-section views of a strut on a stent according to yet another embodiment.
Figure 8B:
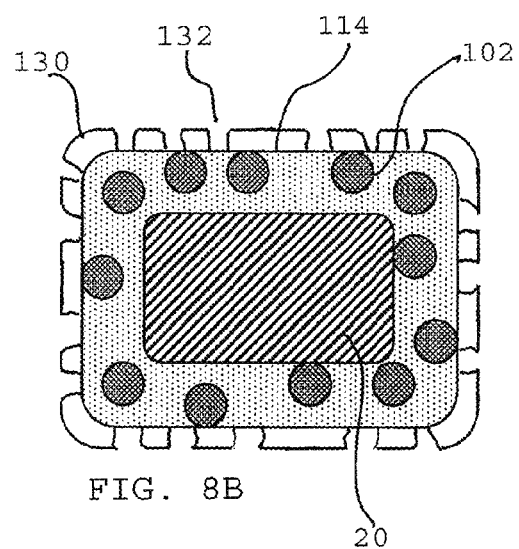

In another example, referring to the embodiment shown in FIGS. 8A and 8B, a stent strut 20 of a stent is coated with a polymer layer 114 containing a therapeutic agent. Embedded in polymer layer 114 are capsules 102 which contain a hydrogel. Polymer layer 114 is coated with a barrier layer 130, which is semi-permeable to allow the passage of fluids through barrier layer 130.

In operation, when the stent is delivered to a target body site, body fluid flows through semi-permeable barrier layer 130, diffuses through polymer layer 114, and hydrates the hydrogel in capsules 102. As shown in FIG. 8B, hydration of the hydrogel causes the volume expansion of capsules 102, which in turn, causes volume expansion of polymer layer 114. This volume expansion of polymer layer 114 causes the formation of cracks 132 in barrier layer 130. These cracks 132 allow the passage of therapeutic agent from polymer layer 114 through barrier layer 132 to the external environment.]

In another embodiment, the swellable material is an oxidizable metal that undergoes volume expansion upon oxidation (e.g., iron). The oxidation can occur upon exposure to an aqueous environment. As such, the oxidizable metal may be used in a manner similar to that for the water-swellable polymer described above.

In yet another aspect, the present invention provides a medical device having a multi-layered coating. The multi-layered coating comprises a first reservoir layer over a surface of the medical device, wherein the first reservoir layer comprises a first therapeutic agent. Further, a first barrier layer is disposed over the first reservoir layer, wherein the first barrier layer comprises a first inorganic material. Further, a second reservoir layer is disposed over the first barrier layer, wherein the second reservoir layer comprises a second therapeutic agent. The reservoir layers are formed using a material that is capable of retaining or holding the therapeutic agent, such as polymeric materials.

The first and second therapeutic agents may be the same or different. For example, one therapeutic agent may be an anti-thrombotic agent and the other therapeutic agent may be an anti-inflammatory agent to provide a combination treatment. Also, various characteristics of the first and second reservoir layers may be the same or different. Such characteristics include, for example, their composition, their density, their thicknesses, and the rate at which the therapeutic agents diffuse through the polymer layers. By independently controlling the characteristics of each reservoir layer, the release rate of the therapeutic agents can be adjusted.

Further, a second barrier layer is disposed over the second reservoir layer, wherein the second barrier layer comprises a second inorganic material. The composition and structure of the barrier layers, as well as the manner in which they may be formed, are as described above. Each barrier layer may each independently have their own various characteristics, including their composition, density, thickness, and permeability to the therapeutic agents.

Further, a plurality of excavated regions (as defined above) penetrate through at least a partial thickness of the multi-layered coating. The excavated regions provide a means by which therapeutic agents in the reservoir layers may be released into the external environment.

Figure 9:
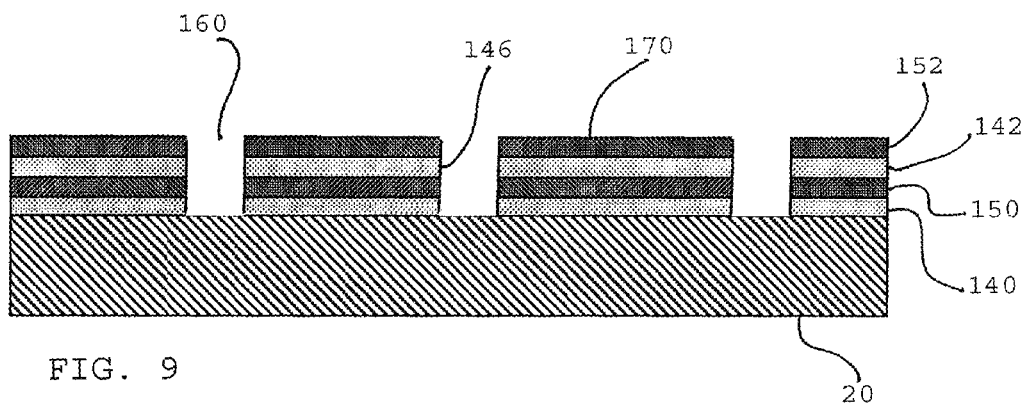
FIG. 9 shows a cross-section view of a strut on a stent having a multi-layered coating according to yet another embodiment.

For example, referring to the embodiment shown in FIG. 9, a stent strut 20 of a stent has a multi-layered coating 170. The first layer in multi-layered coating 170 is a first reservoir layer 140 containing a first therapeutic agent. First reservoir layer 140 is coated with a first barrier layer 150 which, in this particular embodiment, is impermeable to the first therapeutic agent. First barrier layer 150 is coated with a second reservoir layer 142 which contains a second therapeutic agent which, in this particular embodiment, is different from the first therapeutic agent. Second reservoir layer 142 is coated with a second barrier layer 152 which, in this particular embodiment, is impermeable to the second therapeutic agent. Multiple slots 160 penetrating through the full thickness of multi-layered coating 170 are created by laser ablation. In this particular embodiment, slots 160 have a width in the range of 100 nm to 1 µm, but other widths are also possible depending upon the particular application. In operation, when the stent is delivered to a body site, the therapeutic agents diffuse out of reservoir layers 140 and 142 through the side aspects (e.g., side aspect 146) of reservoir layers 140 and 142. The therapeutic agents are then released out of slots 160.

Figure 10:
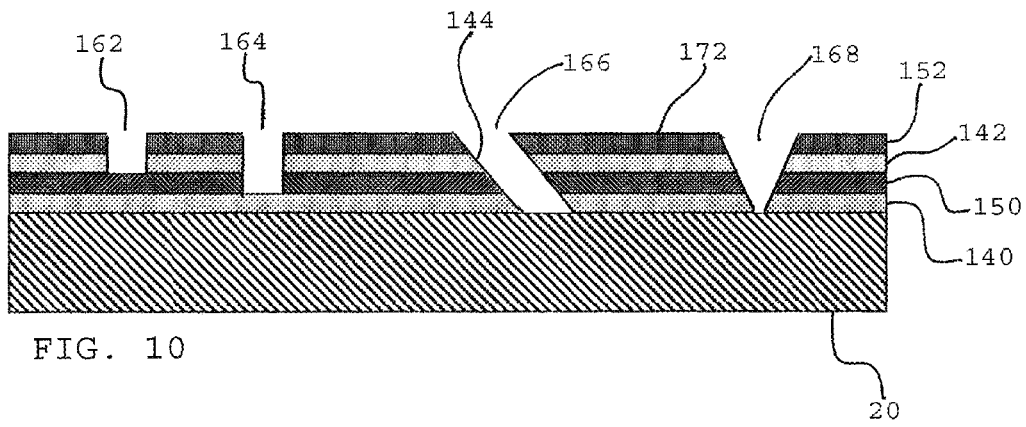
FIG. 10 shows a cross-section view of a strut on a stent having a multi-layered coating according to yet another embodiment.

The excavated regions may have various geometries and dimensions, including various sizes, widths, shapes, and degrees of penetration through the multi-layered coating. This feature may be useful in varying the release rate of the therapeutic agents. For example, referring to the embodiment shown in FIG. 10, a stent strut 20 of a stent has a multi-layered coating 172 with slots (162, 164, 166, and 168) having various different dimensions and geometries. Multi-layered coating 172 has a first reservoir layer 140 containing a first therapeutic agent, a first barrier layer 150, a second reservoir layer 142 containing a second therapeutic agent, and a second barrier layer 152. Slot 162 penetrates partially through multi-layered coating 172 such that only reservoir layer 142 is exposed. Because of this geometry, only the first therapeutic agent in reservoir layer 142 would be released from slot 162. Slot 164 also penetrates partially through the multi-layered coating, but both reservoir layer 140 and 142 are exposed. Slot 166 has a slanted geometry with respect to the plane of multi-layered coating 172. A slot having this geometry may be useful in enlarging the side aspect surface (e.g., side aspect 144) of reservoir layers 140 and 142, which would increase the rate at which the therapeutic agents diffuse out of the layers. Slot 168 has a wedge-shaped geometry, which like slot 166, enlarges the side aspect surface of reservoir layers 140 and 142, which would increase the rate at which the therapeutic agents diffuse out of the layers.

In certain embodiments, the excavated regions on one portion of the medical device have different characteristics than the excavated regions on another portion of the medical device. These different characteristics can involve different geometries or dimensions, or a different arrangement (e.g., pattern, number, or density) of the excavated regions. This feature may be useful in providing different therapeutic agent release rates on different portions of the medical device, or the release of different therapeutic agents on different portions of the medical device. For example, a vascular stent may have larger or a higher density of excavated regions at the end portions of the stent than at the intermediate portions of the stent to reduce the unwanted "edge-effect" that sometimes occurs with stent implantation.

The first and second barrier layers may have varying degrees of permeability to the therapeutic agents, or be completely impermeable. In some cases, the first barrier layer and/or second barrier layer are impermeable so that the therapeutic agent is released only though the excavated regions in the multi-layered coating. The permeability of the barrier layers may be controlled in various ways, including selecting the thickness, the density, the deposition process used, and the composition of the barrier layers. By individually adjusting the permeability of the barrier layers, the release rate profiles of the therapeutic agents may be further controlled.

In certain embodiments, the multi-layered coating comprises a plurality of alternating reservoir layers and barrier layers. For example, there may be a third reservoir layer disposed over the second barrier layer, wherein the third reservoir layer comprises a third therapeutic agent; and a third barrier layer disposed over the third reservoir layer, wherein the third barrier layer comprises a third inorganic material.

In yet another aspect, the present invention provides a medical device having a polymer layer, which comprises a block copolymer and a therapeutic agent. Further, a barrier layer is disposed over the polymer layer. The barrier layer comprises an inorganic material and has a plurality of discontinuities. The composition and structure of the reservoir, as well as the manner in which it may be formed, are as described above. The composition and structure of the barrier layer, as well as the manner in which it may be formed, are as described above.

Figure 11:
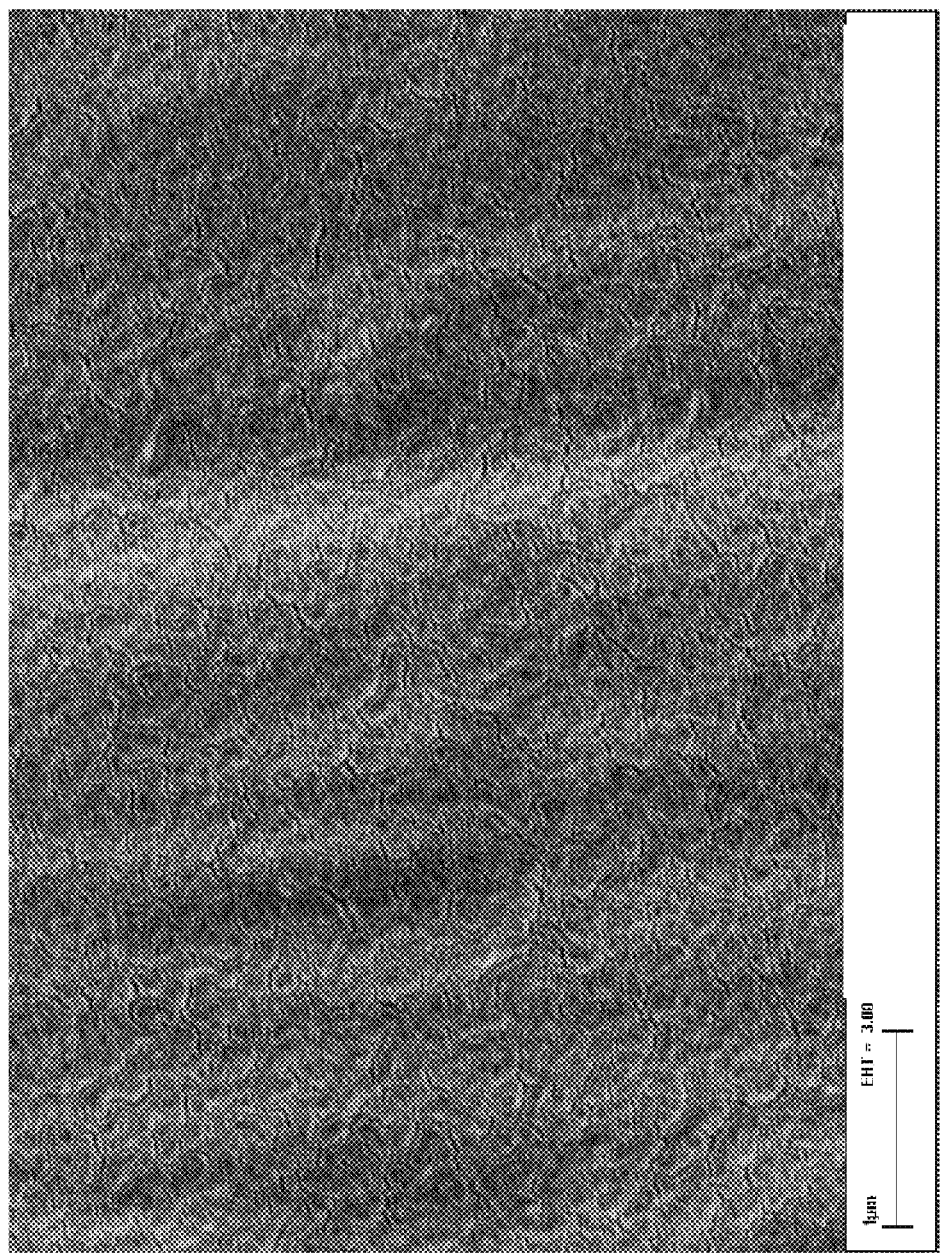
FIG. 11 shows a magnified view of the surface of a sputter-deposited layer of gold.
Figure 12:
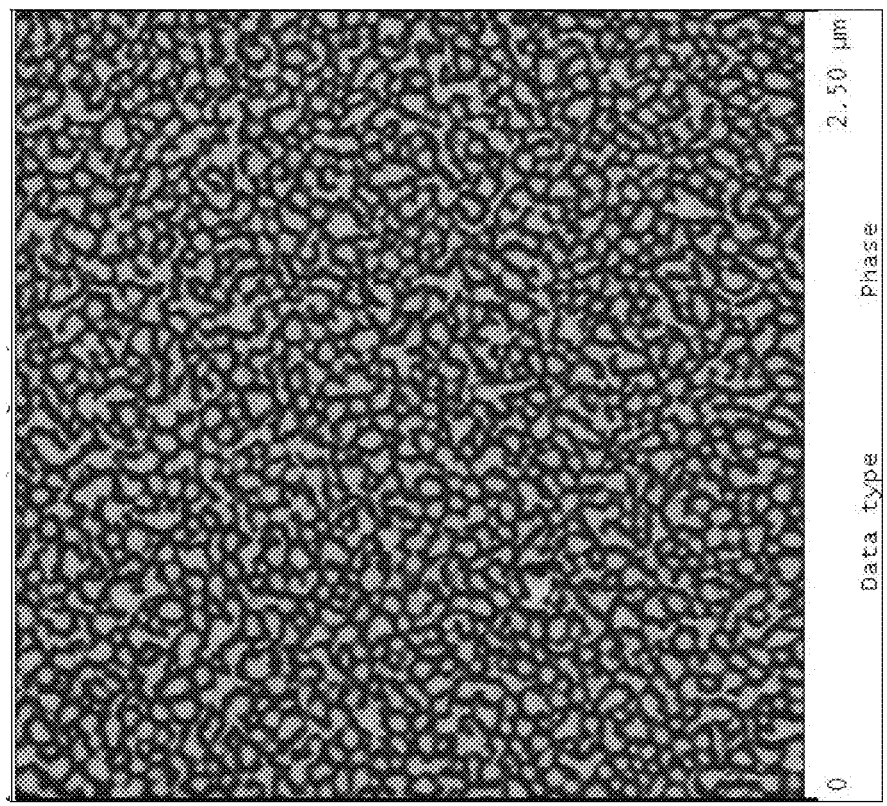
FIG. 12 shows an atomic force microscopic image of the surface of an SIBS block polymer film.

The inventors have discovered that depositing a thin layer of gold (by sputter deposition) onto a film of SIBS block copolymer on a stainless steel coupon unexpectedly resulted in the formation of nanometer-sized (about 20 nm wide) cracks in a reticulated pattern, as shown under 60,000-fold magnification in FIG. 11. It is believed that this pattern of cracks in the gold layer follows the particular surface morphology of the SIBS polymer film. Referring to FIG. 12, an atomic force microscopy image of the SIBS polymer film (deposited by evaporation on a stainless steel stent shows the surface morphology of this film as having features sized from about 30-90 nm. These surface features are believed to be caused by microphase-separated domains of the block copolymers in the film.

Therefore, in this aspect of the present invention, the polymer layer (comprising a block copolymer) and the barrier layer have a synergistic relationship because the resulting formation of discontinuities in the barrier layer allows for the release of therapeutic agent in the polymer layer to the external environment. Also, the polymer layer and the barrier layer have an additional synergistic relationship because the resulting surface morphology of the barrier layer is believed to be capable of promoting endothelial cell attachment and/or growth, which may improve the therapeutic effectiveness of medical devices that are implanted in blood vessels.

In certain embodiments, the surface morphology of the polymer layer comprises a plurality of microphase-separated domains. In some cases, the surface morphology of the barrier layer follows the surface morphology of the polymer layer. In some cases, the discontinuities in the barrier layer follow the surface morphology of the polymer layer. Various characteristics of the microphase-separated domains (e.g., their size, geometry, and periodicity) on the surface of the polymer layer will depend upon the specific characteristics of the block copolymer, such as the relative chain lengths, positions, and composition of the blocks. As such, the block copolymer can be selected to achieve the desired surface morphology in the polymer layer, which in turn, will influence the formation of discontinuities and/or the surface morphology of the barrier layer.

Figure 13:
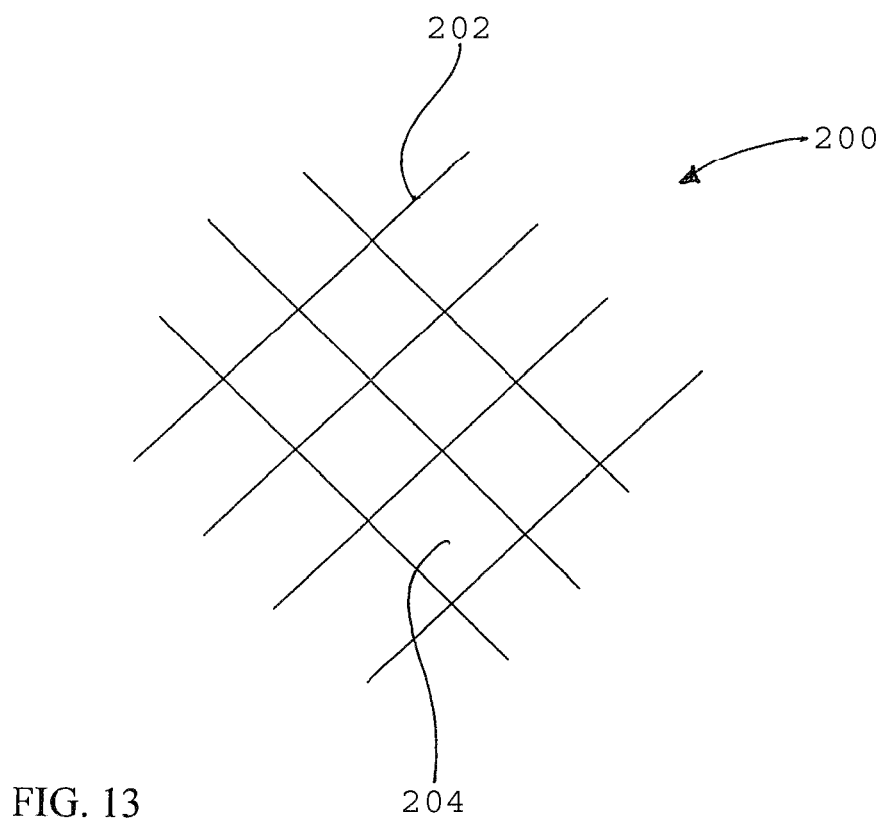
FIG. 13 shows an example of a surface having feature elements (grooves) and feature domains (area enclosed by the grooves).

In certain embodiments, the surface morphology of the barrier layer comprises a plurality of features elements or feature domains having a size that promotes endothelial cell attachment and/or growth. As used herein, the term "feature element" refers to any feature on a surface that causes the surface to be uneven, non-smooth, or discontinuous. For example, the feature elements may be bumps, nodules, ridges, grains, protrusions, pits, holes, openings, cracks, fracture lines, pores, grooves, channels, etc. As used herein, the term "feature domain" refers to a domain that is defined by one or more feature elements. For example, referring to schematic illustration of FIG. 13, a surface 200 comprises multiple grooves 202 which define a series of pattern domains 204. Grooves 202 would be considered feature elements and pattern domains 204 would be considered feature domains. The size of a feature element or feature domain, as used herein, is intended to be measured along its shortest axis. In some cases, the feature elements or feature domains have an average size of less than 200 nm. In some cases, the feature elements or feature domains have an average size in the range of 10 nm to 200 nm; and in some cases, in the range of 30 nm to 90 nm. The pattern of the feature elements or feature domains may be regular or irregular, ordered or random, and have varying densities.

Figure 14A:
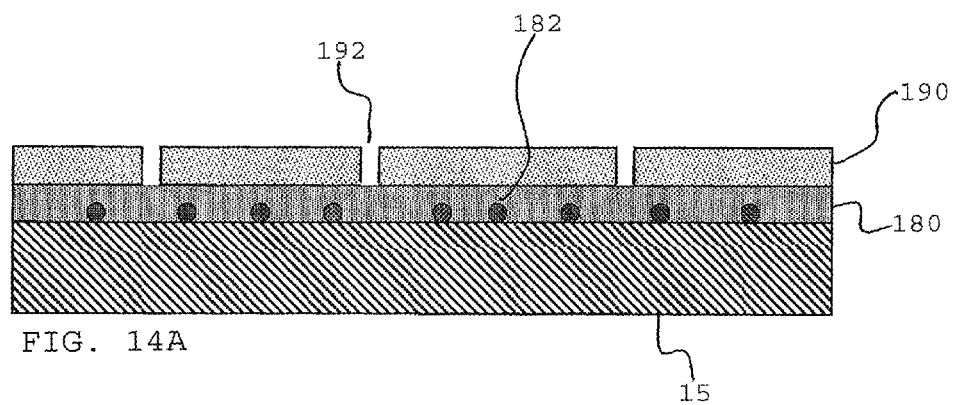
FIGS. 14A and 14B show cross-section views of a strut on a stent according to yet another embodiment.
Figure 14B:
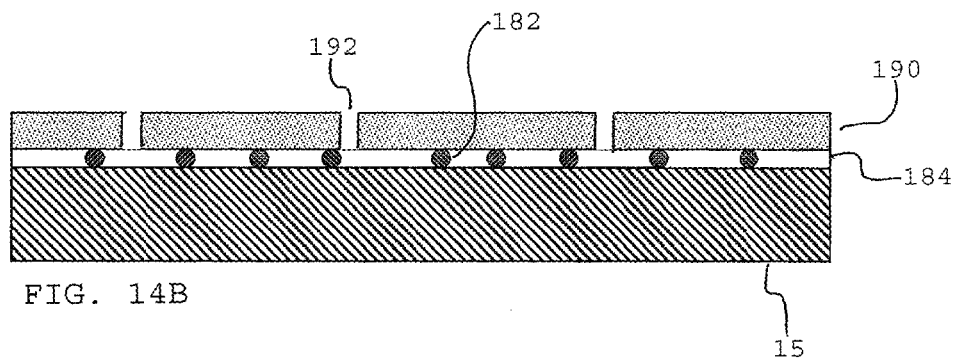

In certain embodiments, the polymer layer is exposed to a solvent which dissolves the polymeric material in the polymer layer, but does not dissolve the therapeutic agent. In some cases, the solvent may access the polymer layer through the discontinuities in the barrier layer. For example, referring to the embodiment shown in FIG. 14A, a medical device 15 is coated with a polymer layer 180 formed of a block copolymer. Polymer layer 180 contains particles 182 of a therapeutic agent. A barrier layer 190 is deposited over polymer layer 180, and cracks 192 form in barrier layer 190 due to the surface morphology of polymer layer 180. Medical device 15 is then exposed to a solvent which penetrates through the cracks 192 of barrier layer 190 and dissolves the polymeric material in polymer layer 180. However, the particles 182 of the therapeutic agent are left intact. As shown in FIG. 14B, this results in a coating in which the therapeutic agent is contained in a polymer-free layer 184 under barrier layer 190. This feature may be useful in reducing exposure of body tissue to polymeric materials which may not be fully biocompatible. In some cases, barrier layer 190 may then be augmented by further depositing additional inorganic material (e.g., a biodegradable metal such as a magnesium alloy, iron, or zinc) onto barrier layer 190. Augmenting barrier layer 190 may be useful in reducing the permeability of barrier layer 190, and thereby, reducing the rate at which the therapeutic agent is released.

Figure 15:
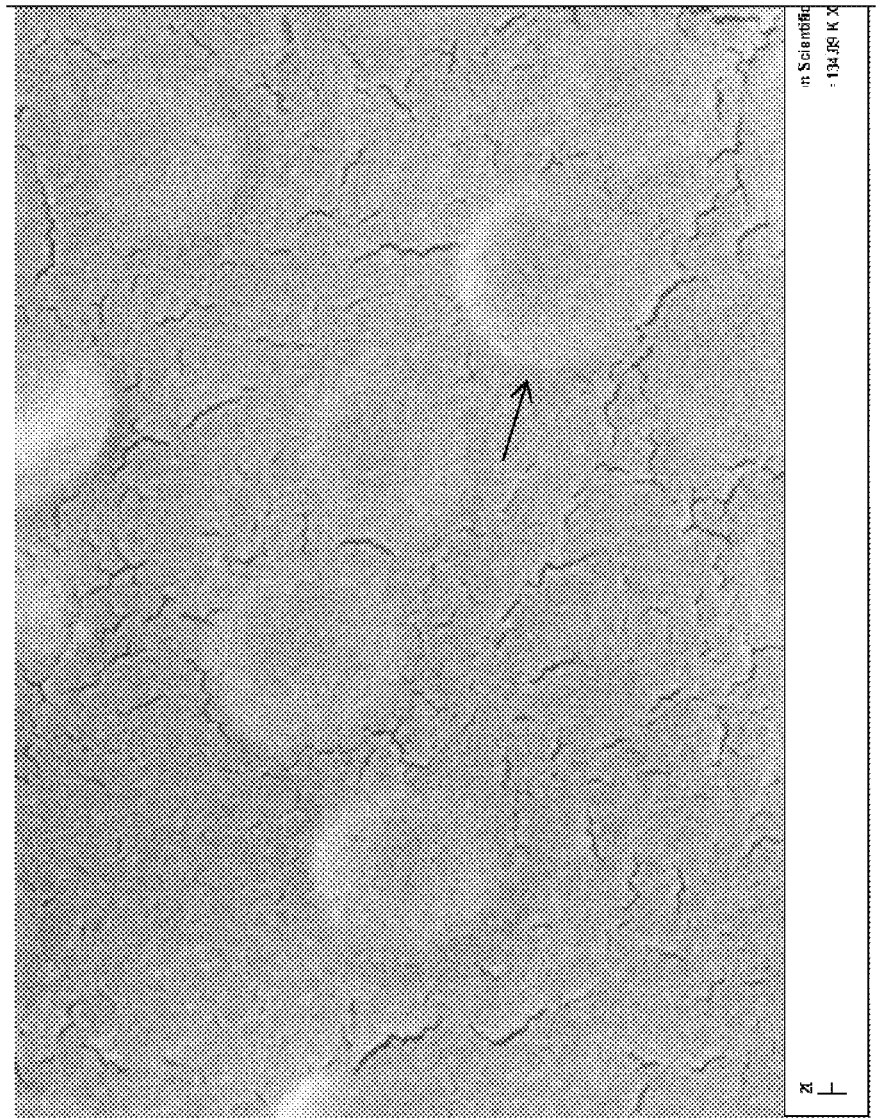
FIG. 15 shows a magnified view of the surface of a layer of sputter-deposited gold with drug particles underneath.
Figure 16:
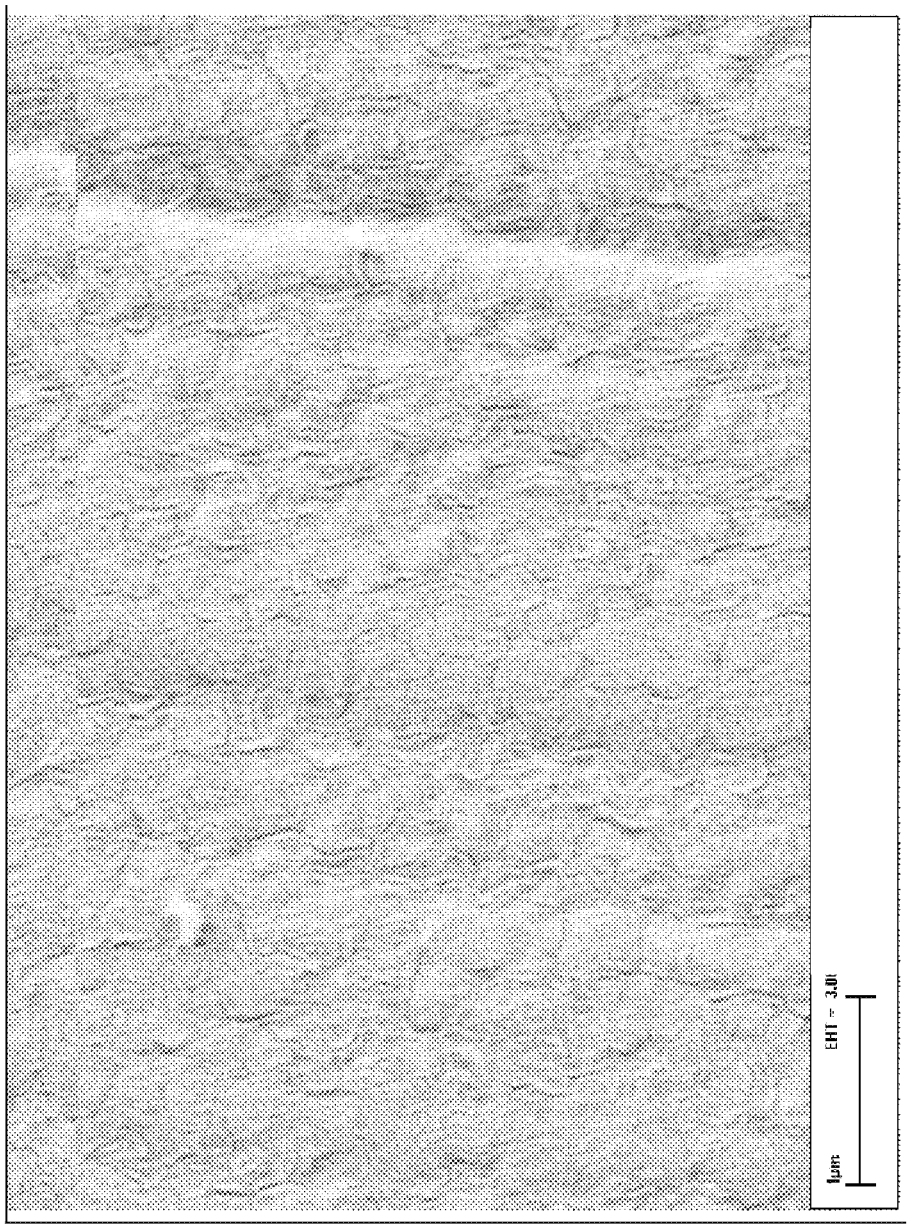
FIG. 16 shows a magnified view of the surface of the gold layer of FIG. 15, after additional sputter-deposition of gold onto the layer.

In an experimental example, a coating was formed by sputter-depositing a layer of gold onto an SIBS block copolymer film stainless steel coupon containing paclitaxel particles. This coating was then exposed to toluene, which penetrated through the cracks in the gold film and dissolved the SIBS polymer. FIG. 15 shows the surface (under 134,00-fold magnification) of the gold layer, in which the preserved paclitaxel particles are evident as bumps (black arrow) in the layer. Additional gold material was then sputtered-deposited onto this coating to form the coating seen in FIG. 16, which shows the surface under 60,000-fold magnification.

Non-limiting examples of medical devices that can be used with the present invention include stents, stent grafts, catheters, guide wires, neurovascular aneurysm coils, balloons, filters (e.g., vena cava filters), vascular grafts, intraluminal paving systems, pacemakers, electrodes, leads, defibrillators, joint and bone implants, spinal implants, access ports, intraaortic balloon pumps, heart valves, sutures, artificial hearts, neurological stimulators, cochlear implants, retinal implants, and other devices that can be used in connection with therapeutic coatings. Such medical devices are implanted or otherwise used in body structures, cavities, or lumens such as the vasculature, gastrointestinal tract, abdomen, peritoneum, airways, esophagus, trachea, colon, rectum, biliary tract, urinary tract, prostate, brain, spine, lung, liver, heart, skeletal muscle, kidney, bladder, intestines, stomach, pancreas, ovary, uterus, cartilage, eye, bone, joints, and the like.

The therapeutic agent used in the present invention may be any pharmaceutically acceptable agent such as a non-genetic therapeutic agent, a biomolecule, a small molecule, or cells.

Exemplary non-genetic therapeutic agents include antithrombogenic agents such heparin, heparin derivatives, prostaglandin (including micellar prostaglandin E1), urokinase, and PPack (dextrophenylalanine proline arginine chloromethylketone); anti-proliferative agents such as enoxaparin, angiopeptin, sirolimus (rapamycin), tacrolimus, everolimus, zotarolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estrodiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis(2-aminoethyl) ethyleneglycol-N,N,N',N'-tetraacetic acid and mixtures thereof, antibiotics such as gentamycin, rifampin, minocyclin, and ciprofloxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promotors such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; inhibitors of heat shock proteins such as geldanamycin; angiotensin converting enzyme (ACE) inhibitors; beta-blockers; βAR kinase (βARK) inhibitors; phospholamban inhibitors; protein-bound particle drugs such as ABRAXANE™; structural protein (e.g., collagen) cross-link breakers such as alagebrium (ALT-711); any combinations and pro-drugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include serca-2 protein, monocyte chemoattractant proteins (MCP-1) and bone morphogenic proteins ("BMP's"), such as, for example, BMP-2, BMP-3, BMP-4, BMP-5, BMP-6 (VGR-1), BMP-7 (OP-1), BMP-8, BMP-9, BMP-10, BMP-11, BMP-12, BMP-13, BMP-14, BMP-15. Preferred BMP's are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedghog" proteins, or the DNA's encoding them. Non-limiting examples of genes include survival genes that protect against cell death, such as anti-apoptotic Bcl-2 family factors and Akt kinase; serca 2 gene; and combinations thereof. Non-limiting examples of angiogenic factors include acidic and basic fibroblast growth factors, vascular endothelial growth factor, epidermal growth factor, transforming growth factors α and β, platelet-derived endothelial growth factor, platelet-derived growth factor, tumor necrosis factor α, hepatocyte growth factor, and insulin-like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include side population (SP) cells, lineage negative (Lin$^-$) cells including Lin$^-$CD34$^-$, Lin$^-$CD34$^+$, Lin$^-$cKit$^+$, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts+5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells. Any of the therapeutic agents may be combined to the extent such combination is biologically compatible.

The polymeric materials used in the present invention may comprise polymers that are biodegradable or non-biodegradable. Non-limiting examples of suitable non-biodegradable polymers include polystyrene; polystyrene maleic anhydride; block copolymers such as styrene-isobutylene-styrene block copolymers (SIBS) and styrene-ethylene/butylene-styrene (SEBS) block copolymers; polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides including poly(methylmethacrylate-butylacetate-methylmethacrylate) block copolymers; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHYDROL®); squalene emulsions; and mixtures and copolymers of any of the foregoing.

Non-limiting examples of suitable biodegradable polymers include polycarboxylic acid, polyanhydries including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L-lactide), poly(lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butyl acrylate; polyhydroxybutyrate valerate and blends; polycarbonates such as tyrosine-derived polycarbonates and acrylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropyl methyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc calcium phosphate.

The foregoing description and examples have been set forth merely to illustrate the invention and are not intended to be limiting. Each of the disclosed aspects and embodiments of the present invention may be considered individually or in combination with other aspects, embodiments, and variations of the invention. Modifications of the disclosed embodiments incorporating the spirit and substance of the invention may occur to persons skilled in the art and such modifications are within the scope of the present invention.

We claim:

1. A medical device comprising:
a reservoir on a surface of a medical device, the reservoir containing a therapeutic agent;
a barrier layer disposed over the reservoir, wherein the barrier layer comprises an inorganic material; and
a swellable material disposed between the barrier layer and the surface of the medical device, wherein the swellable material is a material that swells upon exposure to an aqueous environment,
wherein the barrier layer has a first permeability to the therapeutic agent prior to swelling of the swellable material and a second permeability to the therapeutic agent after swelling of the swellable material, and wherein the second permeability is greater than the first permeability, wherein the first permeability is provided by one or more discontinuities in the barrier layer.

2. A medical device comprising:
a reservoir on a surface of a medical device, the reservoir containing a therapeutic agent;
a barrier layer disposed over the reservoir, wherein the barrier layer comprises an inorganic material; and
a swellable material disposed between the barrier layer and the surface of the medical device, wherein the swellable material is a material that swells upon exposure to an aqueous environment,
wherein the barrier layer has a first permeability to the therapeutic agent prior to swelling of the swellable material, the first permeability being provided by one or more discontinuities in the barrier layer, and a second permeability to the therapeutic agent after swelling of the swellable material, wherein the second permeability is greater than the first permeability, and the swelling of the swellable material causes the formation of further discontinuities in the barrier layer.

3. The medical device of claim 2, wherein the medical device further comprises an intermediate layer disposed between the medical device and the barrier layer, wherein the intermediate layer comprises a polymeric material.

4. The medical device of claim 3, wherein the intermediate layer contains the reservoir containing the therapeutic agent.

5. The medical device of claim 4, wherein the medical device further comprises a swellable layer disposed between the medical device and the barrier layer, and wherein the swellable layer contains the swellable material.

6. The medical device of claim 4, wherein the intermediate layer further comprises the swellable material.

7. The medical device of claim 6, wherein the swellable material is contained in capsules.

8. The medical device of claim 2, wherein the barrier layer has a plurality of regions of structural weakness.

9. The medical device of claim 2, wherein the swellable material is a water-swellable polymer.

10. The medical device of claim 2, wherein the swellable material is an oxidizable metal that swells upon oxidation.

11. The medical device of claim 2, wherein the one or more discontinuities are created by cooling the barrier layer.

12. The medical device of claim 11, wherein the barrier layer is cooled by exposure to a cryogenic liquid.

13. The medical device of claim 2, wherein the one or more discontinuities are created by at least one cycle of heating and then cooling the barrier layer, or at least one cycle of cooling and then heating the barrier layer.

14. The medical device of claim 2, wherein the medical device is a balloon.

15. A stent comprising:
a reservoir on a surface of a medical device, the reservoir containing a therapeutic agent;
a barrier layer disposed over the reservoir, wherein the barrier layer comprises an inorganic material; and
a swellable material disposed between the barrier layer and the surface of the medical device, wherein the swellable material is a material that swells upon exposure to an aqueous environment,
wherein the barrier layer has a first permeability to the therapeutic agent prior to swelling of the swellable material and a second permeability to the therapeutic agent after swelling of the swellable material, and wherein the second permeability is greater than the first permeability, wherein the first permeability is provided by one or more discontinuities in the barrier layer.

16. The stent of claim 15, wherein the swelling of the swellable material causes the formation of further discontinuities in the barrier layer.

17. The stent of claim 15, wherein the stent further comprises an intermediate layer disposed between the medical device and the barrier layer, wherein the intermediate layer comprises a polymeric material.

18. The stent of claim 17, wherein the intermediate layer contains the reservoir containing the therapeutic agent.

19. The stent of claim 17, wherein the medical device further comprises a swellable layer disposed between the stent and the barrier layer, and wherein the swellable layer contains the swellable material.

20. The stent of claim 17, wherein the intermediate layer further comprises the swellable material.

21. The stent of claim 20 wherein the swellable material is contained in capsules.

22. The stent of claim 15, wherein the barrier layer has a plurality of regions of structural weakness.

23. The stent of claim 15, wherein the swellable material is a water-swellable polymer.

24. The stent of claim 15, wherein the swellable material is an oxidizable metal that swells upon oxidation.

25. The stent of claim 15, wherein the one or more discontinuities are created by cooling the barrier layer.

26. The stent of claim 25, wherein the barrier layer is cooled by exposure to a cryogenic liquid.

27. The stent of claim 15, wherein the one or more discontinuities are created by at least one cycle of heating and then cooling the barrier layer, or at least one cycle of cooling and then heating the barrier layer.

28. A stent comprising:
a reservoir on a surface of a stent, the reservoir containing a therapeutic agent;
a barrier layer disposed over the reservoir, wherein the barrier layer comprises an inorganic material; and
a swellable material disposed between the barrier layer and the surface of the stent, wherein the swellable material is a material that swells upon exposure to an aqueous environment,
wherein the barrier layer has a first permeability to the therapeutic agent prior to swelling of the swellable material, the first permeability being provided by one or more discontinuities in the barrier layer, and a second permeability to the therapeutic agent after swelling of the swellable material, wherein the second permeability is greater than the first permeability, and the swelling of the swellable material causes the formation of further discontinuities in the barrier layer.

29. The stent of claim 28, wherein the stent further comprises an intermediate layer disposed between the stent and the barrier layer, wherein the intermediate layer comprises a polymeric material.

30. The stent of claim 29, wherein the intermediate layer contains the reservoir containing the therapeutic agent.

31. The stent of claim 30, wherein the stent further comprises a swellable layer disposed between the stent and the barrier layer, and wherein the swellable layer contains the swellable material.

32. The stent of claim 30, wherein the intermediate layer further comprises the swellable material.

33. The stent of claim 32, wherein the swellable material is contained in capsules.

34. The stent of claim 28, wherein the barrier layer has a plurality of regions of structural weakness.

35. The stent of claim 28, wherein the swellable material is a water-swellable polymer.

36. The stent of claim 28, wherein the swellable material is an oxidizable metal that swells upon oxidation.

37. The medical device of claim 28, wherein the one or more discontinuities are created by cooling the barrier layer.

38. The stent of claim 37, wherein the barrier layer is cooled by exposure to a cryogenic liquid.

39. The stent of claim 28, wherein the one or more discontinuities are created by at least one cycle of heating and then cooling the barrier layer, or at least one cycle of cooling and then heating the barrier layer.

40. The medical device of claim 1, wherein the swelling of the swellable material causes the formation of further discontinuities in the barrier layer.

* * * * *